(12) United States Patent
Duggan

(10) Patent No.: US 10,183,908 B2
(45) Date of Patent: Jan. 22, 2019

(54) COMPOSITIONS FOR THE TREATMENT OF KIDNEY AND/OR LIVER DISEASE

(71) Applicant: VECTUS BIOSYSTEMS LIMITED, Rosebery (AU)

(72) Inventor: Karen Annette Duggan, Clovelly (AU)

(73) Assignee: VECTUS BIOSYSTEMS LIMITED, Rosebery (AU)

( * ) Notice: Subject to any disclaimer, the term of this patent is extended or adjusted under 35 U.S.C. 154(b) by 0 days.

(21) Appl. No.: 15/558,155

(22) PCT Filed: Mar. 18, 2016

(86) PCT No.: PCT/AU2016/000094
§ 371 (c)(1),
(2) Date: Sep. 13, 2017

(87) PCT Pub. No.: WO2016/145478
PCT Pub. Date: Sep. 22, 2016

(65) Prior Publication Data
US 2018/0037539 A1 Feb. 8, 2018

(30) Foreign Application Priority Data

Mar. 18, 2015 (AU) ................................ 2015900978

(51) Int. Cl.
| | | |
|---|---|---|
| C07H 15/203 | (2006.01) |
| C07C 235/34 | (2006.01) |
| C07D 231/12 | (2006.01) |
| C07D 333/24 | (2006.01) |
| C07D 239/26 | (2006.01) |
| C07D 261/08 | (2006.01) |
| C07C 237/20 | (2006.01) |
| C07D 207/327 | (2006.01) |
| C07D 277/30 | (2006.01) |
| C07D 213/56 | (2006.01) |
| C07D 307/54 | (2006.01) |

(52) U.S. Cl.
CPC .......... *C07C 235/34* (2013.01); *C07C 237/20* (2013.01); *C07D 207/327* (2013.01); *C07D 213/56* (2013.01); *C07D 231/12* (2013.01); *C07D 239/26* (2013.01); *C07D 261/08* (2013.01); *C07D 277/30* (2013.01); *C07D 307/54* (2013.01); *C07D 333/24* (2013.01); *C07H 15/203* (2013.01)

(58) Field of Classification Search
None
See application file for complete search history.

(56) References Cited

U.S. PATENT DOCUMENTS

2011/0082109 A1 * 4/2011 Miyanaga ............. C07C 279/22
514/64

FOREIGN PATENT DOCUMENTS

| WO | 2010/042997 A1 | 4/2010 |
| WO | 2015/039172 A1 | 3/2015 |
| WO | 2015/039173 A1 | 3/2015 |

OTHER PUBLICATIONS

Peters, M., et al; A Modular Synthesis of Teraryl-Based α-Helix Mimetics, Part 1: Synthesis of Core Fragments with Two Electronically Differentiated Leaving Groups; Chemistry—A European Journal; 2013; vol. 19, pp. 2442-2449.
Australian Patent Office; International Search Report of PCT/AU2016/000094; dated Apr. 8, 2016; 4 pages.
J.A. Whitworth; Emerging drugs in the management of hypertension; Expert Opinion Emerging Drugs; (2003) 8(2):377-388.
European Patent Office; Supplementary European Search Report dated Sep. 24, 2018; EP Application No. 16764054 (10 pgs.).

* cited by examiner

*Primary Examiner* — Traviss C McIntosh, III
(74) *Attorney, Agent, or Firm* — Kilpatrick Townsend & Stockton LLP

(57) ABSTRACT

The present invention relates to novel compounds and their use in the prophylactic and/or therapeutic treatment of kidney and/or liver disease.

17 Claims, 13 Drawing Sheets

COMPOSITIONS FOR THE TREATMENT OF KIDNEY AND/OR LIVER DISEASE

CROSS-REFERENCE TO RELATED APPLICATIONS

This application is a National Phase application under 35 USC § 371 of Application No. PCT/AU2016/000094, filed Mar. 18, 2016, which application claims priority to Australian Application No. 2015900978, filed Mar. 18, 2015, the teachings of which are hereby incorporated by reference in their entireties for all purposes.

FIELD OF THE INVENTION

The present invention relates to novel compounds and their use in the prophylactic and/or therapeutic treatment of kidney and/or liver disease.

The invention has been developed primarily for the prophylactic and/or therapeutic treatment of kidney and/or liver disease and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Kidney disease consists of a diverse range of etiologies, including immunological, mechanical, metabolic and toxic insults amongst others (Hewitson, Fibrogenesis & Tissue Repair 2012, 5(Suppl 1):S14). Regardless of etiology, all patients with chronic kidney disease show a decline in renal function with time, inevitably leading to end-stage renal failure—a condition that requires life-long dialysis or renal transplantation (Hakim & Lazarus, Am J Kidney Dis 1989, 14:396-401). Progressive loss of renal function is associated not only with development of glomerulosclerosis, but also with that of interstitial fibrosis. Interstitial fibrosis is characterized by the destruction of renal tubules and interstitial capillaries, as well as by the accumulation of extracellular matrix proteins (Fukagawa et al., Nephrol Dial Transplant 1999, 14:2793-2795). Kidney fibrosis can lead to hypertension due to increased systemic vascular resistance, with hypertension reported to occur in 85-95% of patients with chronic kidney disease. (Rao et al., Am J Kidney Dis. 2008, 51(suppl 2):S30-S37).

While treatment with angiotensin-converting-enzyme (ACE) inhibitors alone or in combination with angiotensin receptor blockers (ARBs) have been shown to slow the rate of progression of kidney failure, they do not cure kidney disease, i.e., they do not reverse existing fibrosis and restore normal tissue architecture. Additionally, ACE inhibitors and ARBs may cause side effects such as low blood pressure, angioneurotic oedema, hyperkalaemia and persistent dry cough.

Liver disease can be inherited or caused by a variety of factors that damage the liver, such as obesity, diabetes, infections and alcohol abuse. Examples of liver disease include hepatitis, fatty liver disease and cirrhosis.

In fatty liver disease, large vacuoles of triglyceride fat may accumulate in liver cells via steatosis (i.e., abnormal retention of lipids within a cell). This accumulation of fat can cause inflammation, cell death, and scarring.

Left untreated, the damage from fatty liver disease and other liver diseases results in the accumulation of fibrosis, resulting in cirrhosis, liver failure and portal hypertension; often requiring liver transplantation.

There is no standard treatment for liver fibrosis. Although experimental studies have revealed targets to prevent fibrosis progression in rodents, the efficacy of most treatments has not been proven in humans (Bataller & Brenner, J Clin Invest. 2005, 115(2):209-18). At present, treatment usually focuses on treating the cause of liver fibrosis and hoping that the liver regenerates. Treatments aimed at reversing the fibrosis are usually too toxic for long-term use (e.g., corticosteroids, penicillamine) or have no proven efficacy (e.g., colchicine).

Currently there is no pharmacological therapy for hepatic fat accumulation.

There is a need for agents that prevent or treat kidney disease and/or liver disease. In particular, there is a need for agents that prevent, reduce or slow progression of kidney and/or liver fibrosis, reduce established kidney and/or liver fibrosis, prevent, reduce or slow renal tubular cell death, restore normal tissue architecture in the kidney and/or liver, and/or prevent, reduce or slow hepatic fat accumulation.

It is an object of the present invention to overcome or ameliorate at least one of the disadvantages of the prior art, or to provide a useful alternative.

SUMMARY OF THE INVENTION

According to one aspect, the present invention relates to a compound of the formula:

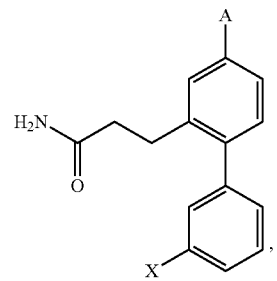

wherein:

A is:

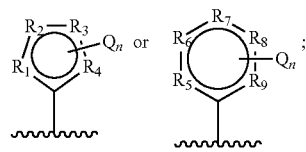

$R_1$ to $R_9$ are independently C, N, O or S;

Q is independently selected from $C_{1-6}$alkyl, halo, $C_{0-6}$alkyl carboxylic acid, amino, hydroxy and $C_{1-6}$alkoxy;

n is 0, 1, 2, 3 or 4; and

X is —OH or

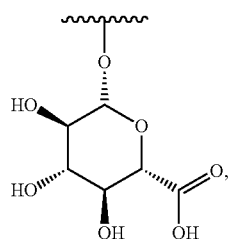

or a pharmacologically acceptable salt, stereoisomer, diastereomer, enantiomar, racemate, hydrate and/or solvate thereof, wherein when X is —OH, A cannot be unsubstituted phenyl.

In one embodiment, G is independently selected from —CH$_3$, —C(O)OH, —F, —NH$_2$, —OH and —OCH$_3$.

In one embodiment, R$_5$ to R$_9$ are independently C or N.

In one embodiment, n is 0, 1 or 2.

In one embodiment, the C$_{0-6}$alkyl carboxylic acid is carboxylic acid.

In one embodiment, X is —OH.

In one embodiment, X is

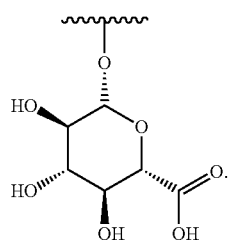

In one embodiment, the compound is selected from:

(P5)

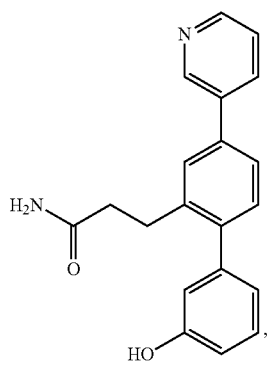

(P8)

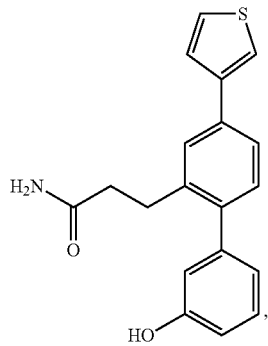

(P9)

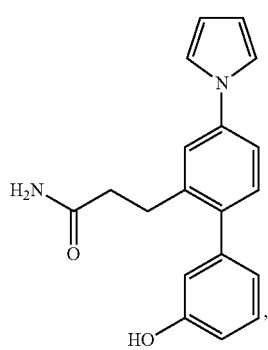

(P11)

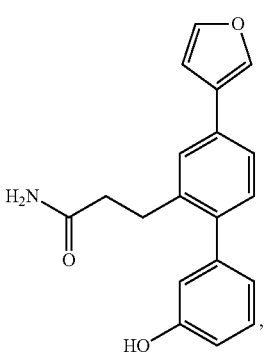

(P22)

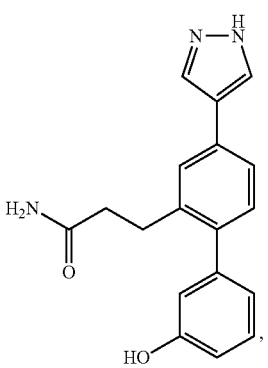

(P26)
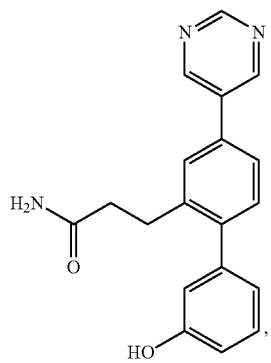
(P40)
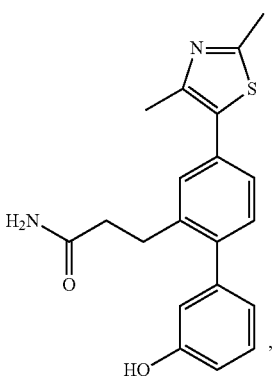
(P41)
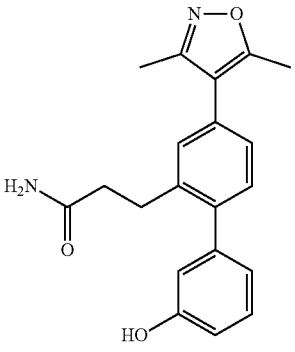
(P47)
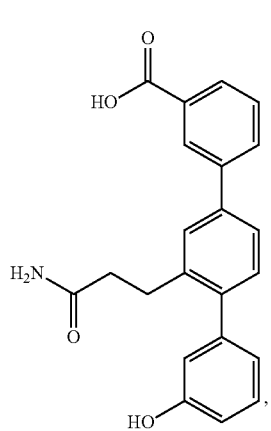
(P3)
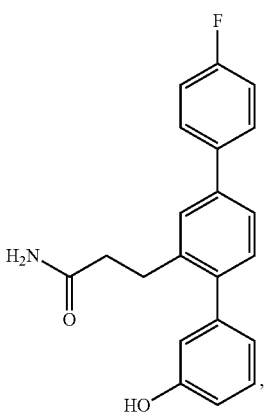
(P49)
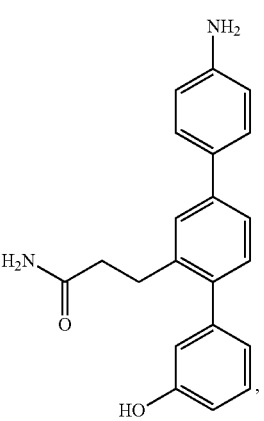
(P46)
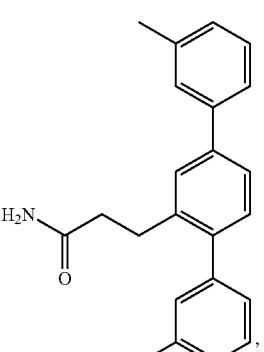
(P48)
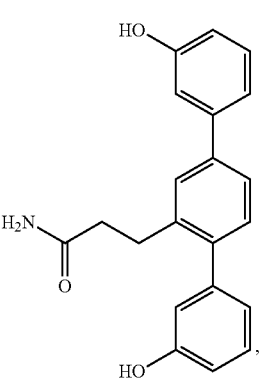

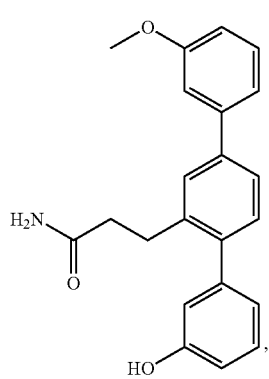
(P50)
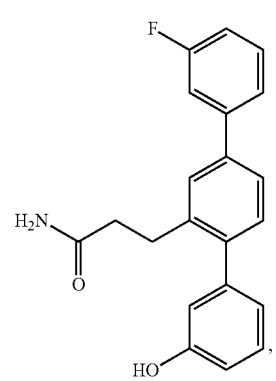
(P1)
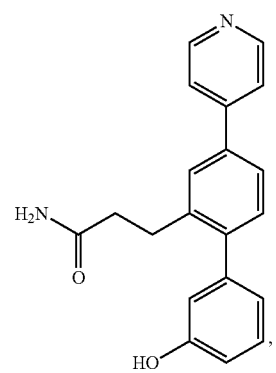
(P6)
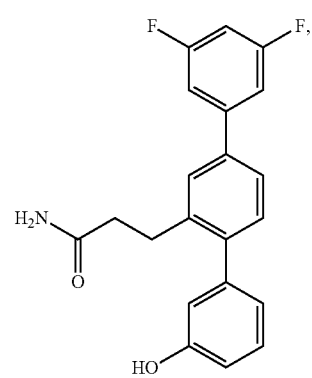
(P33)
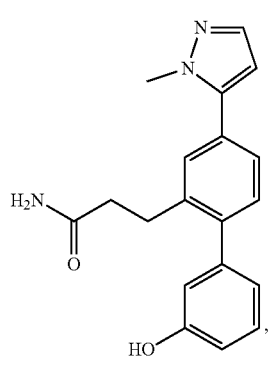
(P38)
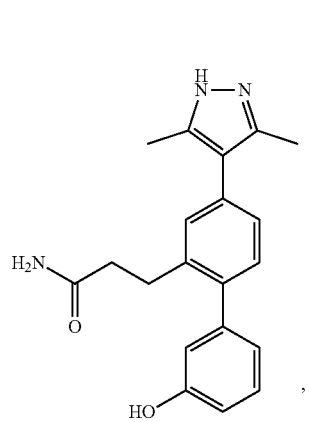
(P42)
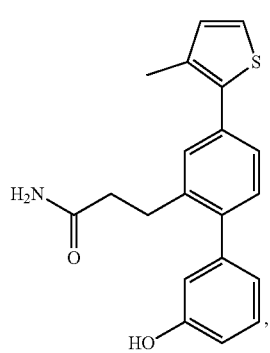
(P43)
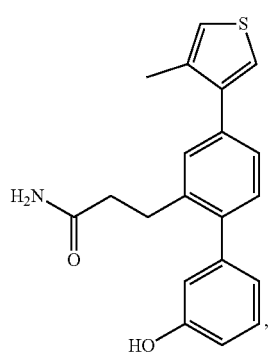
(P44)

-continued

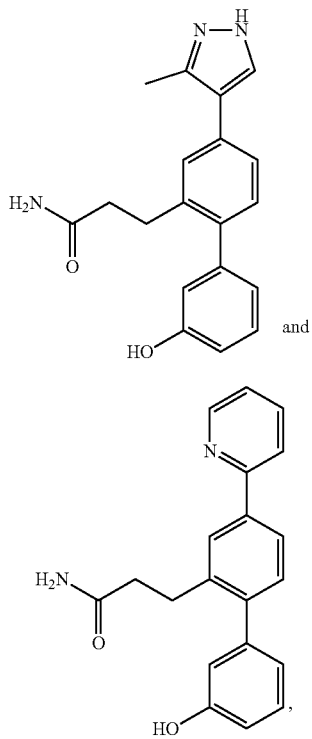

(P45)

and (P4)

or a pharmacologically acceptable salt, glucuronide, stereoisomer, diastereomer, enantiomer, racemate, hydrate and/or solvate thereof.

In one embodiment, the compound is:

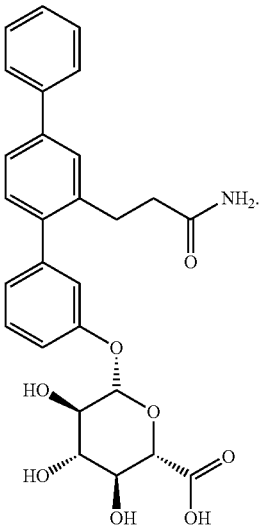

(P104)

or a pharmacologically acceptable salt, stereoisomer, diastereomer, enantiomer, racemate, hydrate and/or solvate thereof.

According to another aspect, the present invention relates to a pharmaceutical composition comprising a compound of the present invention and a pharmaceutical acceptable excipient.

According to another aspect, the present invention relates to a method for the therapeutic treatment of kidney and/or liver disease in a subject comprising administering to the subject a compound or a pharmaceutical composition according to the present invention.

According to another aspect, the present invention relates to a method for the prophylactic treatment of kidney and/or liver disease in a subject comprising administering to the subject a compound or a pharmaceutical composition according to the present invention.

According to another aspect, the present invention relates to a compound or a pharmaceutical composition of the present invention for use in a method for the therapeutic treatment of kidney and/or liver disease.

According to another aspect, the present invention relates to a compound or a pharmaceutical composition of the present invention for use in a method for the prophylactic treatment of kidney and/or liver disease.

According to another aspect, the present invention relates to use of a compound of the present invention for the manufacture of a medicament for the therapeutic treatment of kidney and/or liver disease.

According to another aspect, the present invention relates to use of a compound of the present invention for the manufacture of a medicament for the prophylactic treatment of kidney and/or liver disease.

In one embodiment, the compound, pharmaceutical composition or medicament of the invention prevents, reduces or slows the progression of kidney and/or liver fibrosis.

In one embodiment, the compound, pharmaceutical composition or medicament of the invention reduces established kidney and/or liver fibrosis.

In one embodiment, the compound, pharmaceutical composition or medicament of the invention prevents, reduces or slows renal tubular cell death.

In one embodiment, the compound, pharmaceutical composition or medicament of the invention prevents, reduces or slows fat accumulation in the liver.

In one embodiment, the compound, pharmaceutical composition or medicament of the invention restores normal tissue architecture in the kidney and/or liver.

According to another aspect, the present invention relates a compound of the formula:

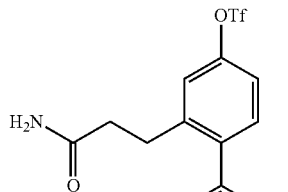

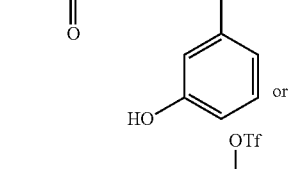

or

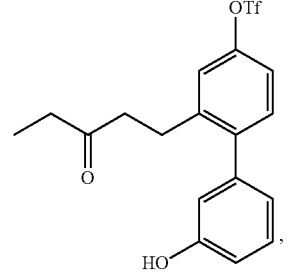

, or a pharmacologically acceptable salt, glucuronide, stereoisomer, diastereomer, enantiomer, racemate, hydrate and/or solvate thereof.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DETAILED DESCRIPTION OF THE INVENTION

Figure 1:
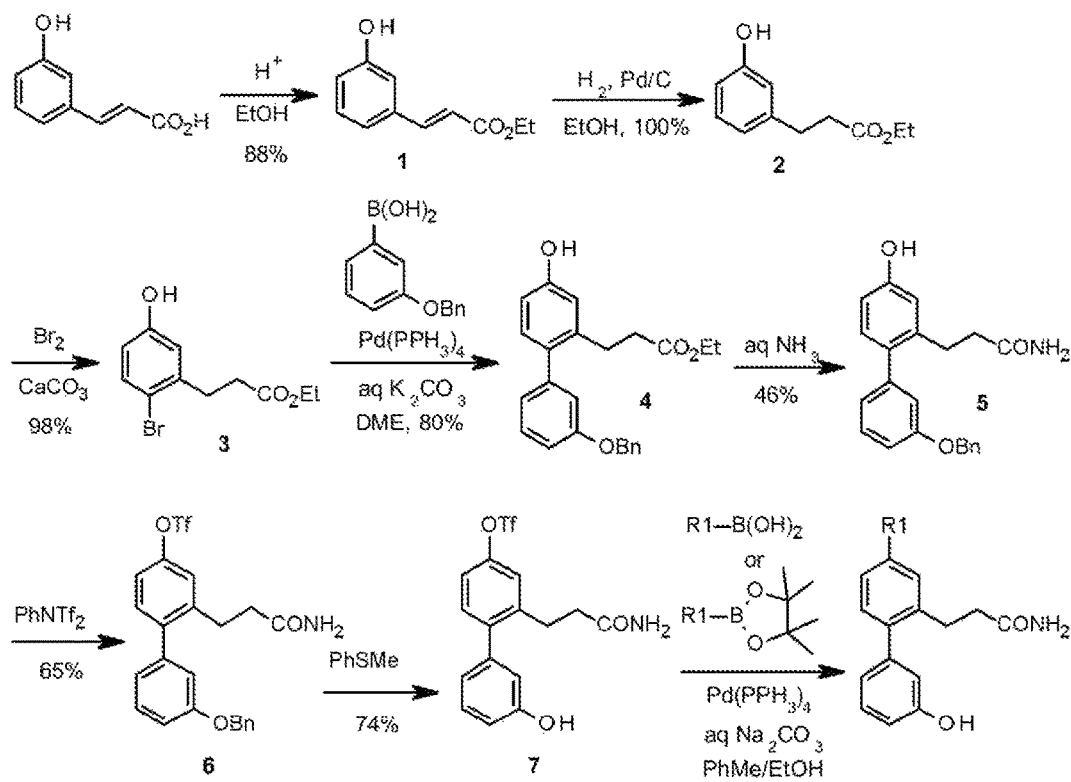
FIG. 1: Synthesis scheme for P5, P8, P11, P22, P28, P40 and P41.

The present invention relates to compounds that are effective in the treatment of kidney and/or liver diseases.

The invention also relates to compounds that are effective in preventing, reducing or slowing progression of kidney and/or liver fibrosis, reducing established kidney and/or liver fibrosis, preventing, reducing or slowing renal tubular cell death, restoring normal tissue architecture in the kidney and/or liver, and/or preventing, reducing or slowing hepatic fat accumulation.

The compounds of the present invention are represented by the formula:

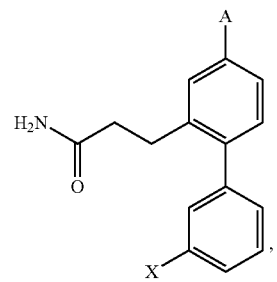

wherein:
A is:

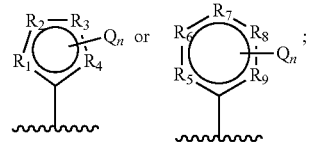

$R_1$ to $R_9$ are independently C, N, O or S;
Q is independently selected from $C_{1-6}$alkyl, halo, $C_{0-6}$alkyl carboxylic acid, amino, hydroxy and $C_{1-6}$alkoxy;
n is 0, 1, 2, 3 or 4; and
X is —OH or

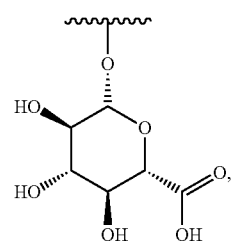

or a pharmacologically acceptable salt, stereoisomer, diastereomer, enantiomer, racemate, hydrate and/or solvate thereof,
wherein when X is —OH, A cannot be unsubstituted phenyl.

The following compounds are specific, but non-limiting, examples of the compounds of the present invention:

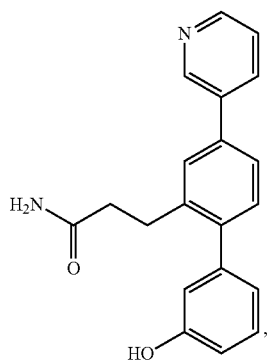 (P5)
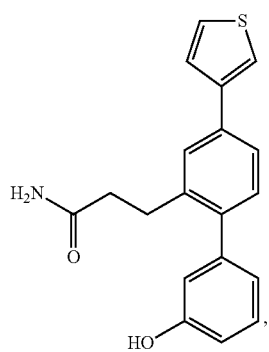 (P8)
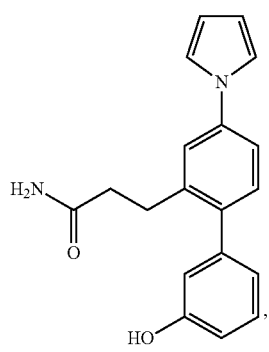 (P9)
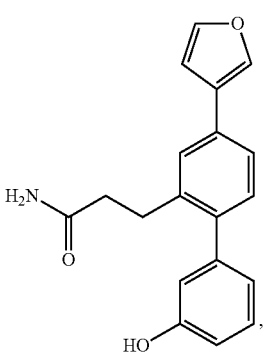 (P11)
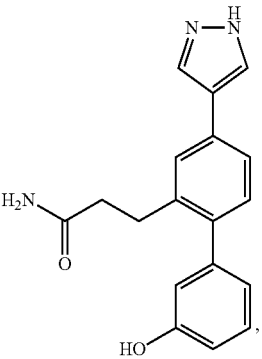 (P22)
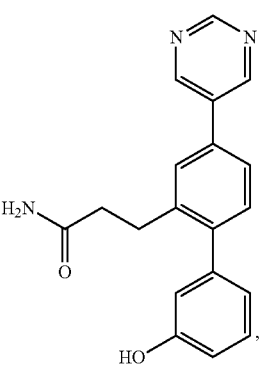 (P26)
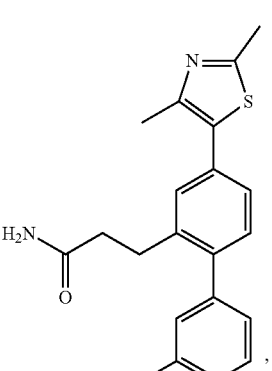 (P40)
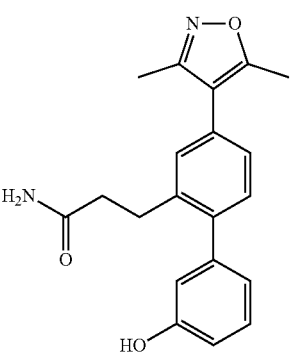 (P41)

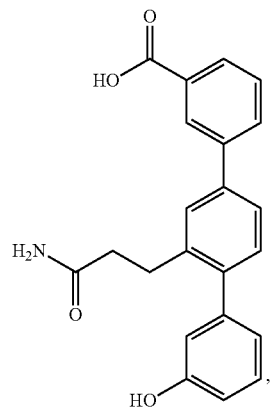
(P47)
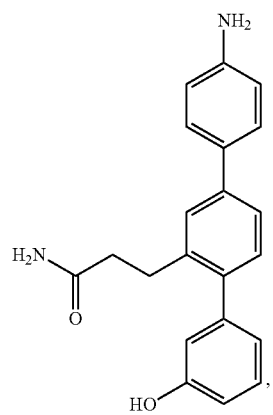
(P3)
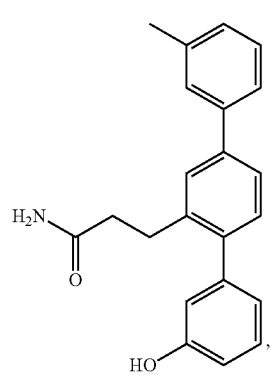
(P49)
(P46)
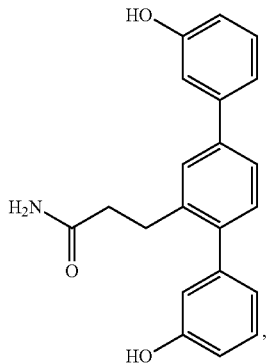
(P48)
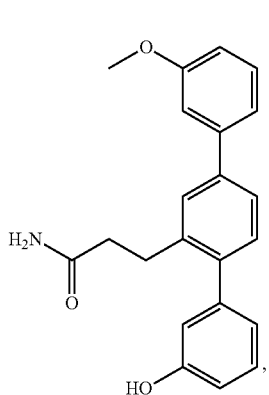
(P50)
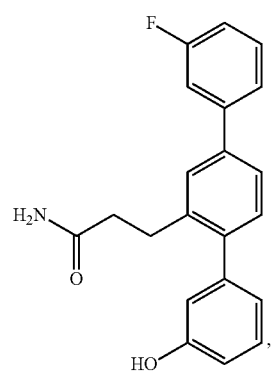
(P1)
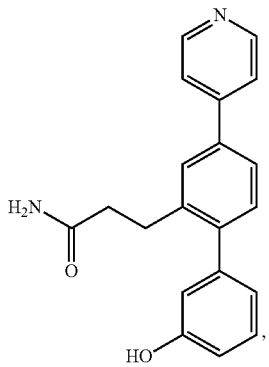
(P6)

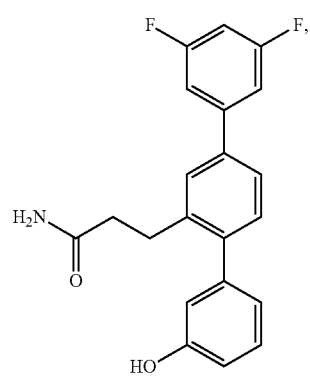
(P33)
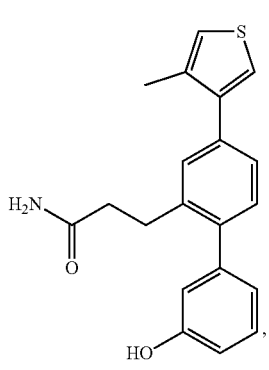
(P44)
(P38)
(P45)
(P42)
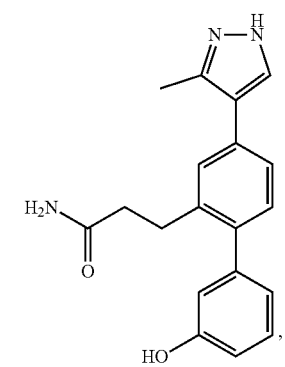
(P4)
(P43)
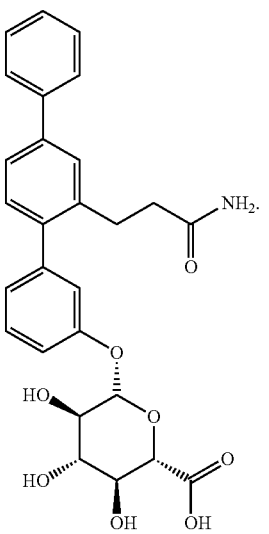
(P104)

As used herein, the term "alkyl", alone or in combination, means a straight-chain or branched-chain alkyl radical of the formula —$C_nH_{(2n+1)}$. Examples of alkyls include methyl, ethyl, n-propyl, n-butyl, isobutyl, sec-butyl, tert-butyl, pentyl, isoamyl, hexyl, octyl and the like.

As used herein, the term "alkoxy", alone or in combination, means an alkyl bonded to an oxygen, wherein the term alkyl is as defined above. Examples of alkoxys include methoxy, ethoxy, n-propoxy, isopropoxy, n-butoxy, iso-butoxy, sec-butoxy, tert-butoxy and the like.

As used herein, the term "halo" designates —F, —Cl, —Br or —I.

As used herein, the term "hydroxy" designates —OH.

As used herein, the term "amino" or "amine" designates —$NH_2$.

As used herein, the term "carboxylic acid" designates —C(O)OH.

As used herein, the term "glucuronide" includes compounds wherein glucuronic acid is linked to the compound via a glycosidic bond.

As used herein, the abbreviations Me, Et, Ph, Ms represent methyl, ethyl, phenyl, and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Compounds of the present invention may exist in particular geometric or stereoisomeric forms. The present invention contemplates all such compounds, including cis- and trans-isomers, (R)- and (S)-enantiomers, diastereomers, (d)-isomers, (l)-isomers, the racemic mixtures thereof, and other mixtures thereof, as falling within the scope of the invention. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, diastereomeric salts may be formed with an appropriate optically active acid or base, followed by resolution of the diastereomers thus formed by fractional crystallization or chromatographic means well known in the art, and subsequent recovery of the pure enantiomers.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

Other than where noted, compound synthesis methods are based on well established methods described in, for example, March's Advanced Organic Chemistry: Reactions, Mechanisms, and Structure (2013) by Michael B. Smith; Advanced Organic Chemistry, Part A: Structure and Mechanisms (2008) and Advanced Organic Chemistry: Part B: Reaction and Synthesis (2010) by Francis A. Carey and Richard J. Sunberg; and Greene's Protective Groups in Organic Synthesis (2014) by Peter G. M. Wuts.

The present invention also contemplates pharmaceutically acceptable salts of the compounds. The term "pharmaceutically acceptable salt" includes both acid and base addition salts and refers to salts which retain the biological effectiveness and properties of the free bases or acids, and which are not biologically or otherwise undesirable. The pharmaceutically acceptable salts are formed with inorganic or organic acids or bases, and can be prepared in situ during the final isolation and purification of the compounds, or by separately reacting a purified compound in its free base or acid form with a suitable organic or inorganic acid or base, and isolating the salt thus formed.

In addition to treatment of established kidney and/or liver disease, the compounds of the present invention may be used prophylactically in subjects at risk of developing kidney and/or liver disease. Examples of subjects in the risk category for developing kidney fibrosis include those with kidney injury or chronic kidney disease, having diabetes, or receiving drugs used in cancer chemotherapy (such as daunorubicin, cisplatin), malignancies (such as myeloma and lymphoma) genetic predisposition (Alport syndrome, Polycystic kidney disease, reflux nephropathy), infections (Hep B Hep C), drugs for treatment of hypomania (lithium), transplant rejection (cyclosporine, tacrolimus), arthritic conditions (NSAIDs, penicillamine, gold) And those exposed to heavy metals such as lead and cadmium. Examples of subjects in the risk category for developing liver fibrosis include those with Hepatitis A, Hepatitis B, Hepatitis C, chronic alcohol abuse, autoimmune hepatitis, primary biliary cirrhosis, primary sclerosing cholangitis hemochromatosis, fatty liver disease, hepatic encephalopathy, hepatic fat accumulation, gallstones, cancer or acute liver injury.

The term "prophylactic" as used in the context of the present invention is intended inter alia to encompass treatments used to prevent or slow down the development of kidney and/or liver disease in the at risk group. Subjects who may be given prophylactic treatment may already have signs of early kidney and/or liver failure.

As used herein, the term "fibrosis" refers to the formation of excess fibrous connective tissue in an organ or tissue.

All organs rely on specific, but different, arrangement of tissues (architecture) for normal function. Disease and/or fibrotic depositions can cause malfunction or poor function of the organ. Thus, restoring normal tissue architecture enables organs to regain their normal function.

The present invention also contemplates pharmaceutical compositions which include the compounds of the present invention, in conjunction with acceptable pharmaceutical excipients. The term "pharmaceutically acceptable excipient" as used in the context of the present invention means any pharmaceutically acceptable inactive component of the composition. As is well known in the art, excipients include diluents, buffers, binders, lubricants, disintegrants, colorants, antioxidants/preservatives, pH-adjusters, etc. The excipients are selected based on the desired physical aspects of the final form: e.g. obtaining a tablet with desired hardness and friability being rapidly dispersible and easily swallowed etc. The desired release rate of the active substance from the composition after its ingestion also plays a role in the choice of excipients. Pharmaceutical compositions may include any type of dosage form such as tablets, capsules, powders, liquid formulations, delayed or sustained release, patches, snuffs, nasal sprays and the like. The physical form and content of the pharmaceutical compositions contemplated are conventional preparations that can be formulated by those skilled in the pharmaceutical formulation field and are based on well established principles and compositions described in, for example, Remington: The Science and Practice of Pharmacy, 19th Edition, 1995; British Pharmacopoeia 2000 and similar formulation texts and manuals.

For example, where the compounds or compositions are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent.

When the compound(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The dosage of a compound and frequency of administration that should be used can also be easily determined by the practicing physician in order to produce the desired response.

Although the dosage will vary depending on the symptoms, age and body weight of the patient, the nature and severity of the disorder to be treated or prevented, the route of administration and the form of the drug, in general, a daily dosage of from 0.0001 mg to 200 mg of the compound of the present invention may be a suitable effective amount for an adult human patient, and this may be administered in a single dose or in divided doses.

A "patient" or "subject" to be treated by the subject method can mean either a human or non-human subject.

An "effective amount" of a subject compound, with respect to a method of treatment, refers to an amount of the therapeutic in a preparation which, when applied as part of a desired dosage regimen provides a benefit according to clinically acceptable standards for the treatment or prophylaxis of a particular disorder.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

EXAMPLES

Example 1: Synthesis of P5, P8, P11, P22, P26, P40 and P41

The synthetic route used to prepare P5, P8, P11, P22, P26, P40 and P41 is shown in FIG. 1. Firstly, 3-hydroxycinnamic acid was esterified to yield ester (1), which was and then hydrogenated to give ethyl propionate (2), and treated with bromine to furnish aryl bromide (3). A Suzuki cross-coupling reaction between aryl bromide (3) and 3-benzyfoxyphenylboronic acid yielded biphenyl (4), which subsequently underwent an aminolysis reaction with ammonia to afford amide (5). Reaction of compound 5 with N-phenyltriflamide afforded aryl triflate (8), which was subsequently treated with thioanisole/TFA to yield aryl triflate (7).

A series of Suzuki cross-coupling reactions between aryl triflate (7) and appropriate arylboronic acids/esters afforded P5, P8, P11, P22, P26, P40 and P41. The results of the Suzuki cross-coupling reactions between aryl triflate (7) and appropriate boronic acids/esters are summarised in Table 1.

TABLE 1

Suzuki cross-coupling reactions of aryl triflate (7) with appropriate boronic acids/esters to produce P5, P8, P11, P22, P26, P40 and P41.

| Compound # | $R^1$ | Isolated yield (%) |
|---|---|---|
| P5 | pyridine | 21 |
| P8 | thiophene (S) | 50 |
| P11 | furan (O) | 58 |
| P22 | 1H-pyrazole (HN—N) | 26 |
| P26 | pyrimidine (N⌒N) | 20 |
| P40 | 2,4-dimethylthiazole | 26 |
| P41 | 3,5-dimethylisoxazole (N—O) | 33 |

Figure 2:
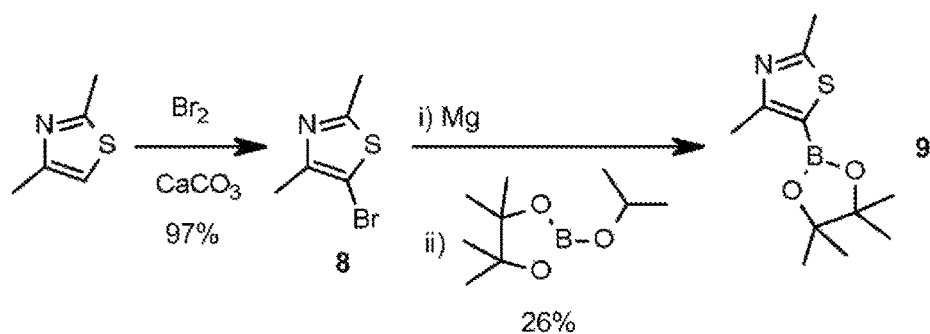
FIG. 2: Synthesis scheme for thiazole pinacol boronic ester.

To synthesise P40, the requisite thiazole pinacol boronic ester (9) needed to be prepared. Thus, 2,4-dimethylthiazole was brominated to yield 5-bromo-2,4-dimethylthiazole (8), which in turn was metallated and treated with pinacol isopropoxy boronic ester to form thiazole pinacol boronic ester 9 (FIG. 2).

Production of (E)-Ethyl 3-(3-hydroxyphenyl)acrylate (1)

To a stirred solution of (E)-3-(3-hydroxyphenyl)acrylic acid (60.70 g, 370.0 mmol) in ethanol (600 mL) was added concentrated sulfuric acid (6 ml) and the reaction mixture heated at reflux for 3 hours, and then at ambient temperature for 18 hours. The ethanol was removed by rotary evaporation and the residue partitioned between water and ethyl acetate. The layers were separated and the organic phase washed with saturated sodium bicarbonate solution and brine and concentrated to dryness. The hot oil was then triturated with dichloromethane and heptane. The resultant solid was collected by filtration to give (E)-ethyl 3-(3-hydroxyphenyl)acrylate (1) (62.77 g, 88%) as beige solid, mp 63.8-65.2° C.; $^1$H NMR (400 MHz, CDCl$_3$) δ 7.74 (d, 1H, $^3J_{trans}$ 16 Hz), 7.35 (m, 1H), 7.19 (d, 1H, J 7.6 Hz), 7.14 (m, 1H), 6.99 (m, 1H), 6.51 (d, 1H, $^3J_{trans}$ 16 Hz), 5.97 (br s, 1H), 4.38 (q, 2H, J 7.1 Hz), 1.44 (t, 3H, J 7.1 Hz).

Production of Ethyl 3-(3-hydroxyphenyl)propanoate (2)

(E)-Ethyl 3-(3-hydroxyphenyl)acrylate (1) (62.62 g, 326.0 mmol) and 10% palladium on carbon (50% wt water) in ethanol (260 mL) was stirred in an autoclave at 140 psi of hydrogen for 1 hour, in 3 batches. The 3 batches were combined, filtered through Celite, washing thoroughly with ethanol. The filtrate was concentrated to give ethyl 3-(3-hydroxyphenyl)propanoate (2) as a pale tan oil (63.23 g, 100%). $^1$H NMR (400 MHz, CDCl$_3$) δ 7.23 (m, 1H), 6.92 (br s, 1H), 6.85-6.80 (m, 3H), 4.24 (q, 2H, J 7.1 Hz), 3.00 (t, 2H, J 7.5 Hz), 2.72 (t, 2H, J 7.5 Hz), 1.34 (t, 3H, J 7.1 Hz).

Production of Ethyl 3-(2-bromo-5-hydroxyphenyl)propanoate (3)

To a vigorously stirred mixture of 3-(3-hydroxyphenyl)propanoate (2) (50.0 g, 0.258 mol) and calcium carbonate (33.5 g, 0.335 mol) in dry DCM (500 ml) was slowly added bromine (13.25 mL, 0.258 mol) over a period of 2 hours. Sodium metabisulfite (12.5 g, 65.79 mmol) in water (60 mL) was added. The reaction mixture was then dried, filtered and concentrated to give ethyl 3-(2-bromo-5-hydroxyphenyl)propanoate (3) as pale tan oil (69.27 g, 98%). $^1$H NMR (400 MHz, CDCl$_3$) δ 7.32 (d, 1H, J 8.6 Hz), 6.75 (d, 1H, J 3.0 Hz), 6.58 (dd, 1H, J 8.6, 3.0 Hz), 6.28 (s, 1H), 4.12 (q, 2H, J 7.2 Hz), 2.96 (t, 2H, J 7.5 Hz), 2.62 (t, 3H, J 7.5 Hz), 1.22 (q, 3H, J 7.2 Hz). $^{13}$C NMR (100 MHz, CDCl$_3$) δ 174.2, 155.6, 140.6, 133.6, 117.5, 115.6, 114.3, 61.3, 34.3, 31.5, 14.2. EIMS: m/z Found: M$^{+-}$ 272.0028, C$_{11}$H$_{13}$BrO$_3$ requires 272.0043. EIMS: m/z 272 (M$^{+-}$, 5%), 193 (86), 165 (100).

Production of Ethyl 3-(3'-benzyloxy-4-hydroxy-[1,1'-biphenyl]-2-yl)propanoate (4)

A solution of ethyl 3-(2-bromo-5-hydroxyphenyl)propanoate (3) (35.0 g, 128.0 mmol) in dimethoxyethane (650 mL) was degassed with nitrogen for 10 minutes. Tetrakis (triphenylphosine)palladium(0) (3.50 g, 3.03 mmol) was added and the reaction mixture stirred for another 15 minutes. An aqueous 2M solution of potassium carbonate (200 mL, 0.40 mmol) was added, followed by 3-benyloxyphenylboronic acid (35.0 g, 154.0 mmol). The reaction mixture was heated at reflux for 2 hours, then cooled to ambient temperature and partitioned between 2M hydrochloric acid and ethyl acetate. The layers were separated and the aqueous layer extracted once more with ethyl acetate. The combined organic extracts were washed with water and brine and concentrated to give the crude product as a tan oil. The crude material was pre-absorbed onto Celite then chromatographed (DCVC) eluting with a gradient of DCM in heptane (50-100% DCM) and then with a gradient of ethyl acetate in DCM (2-6% ethyl acetate) to give, after concentration, the material as a yellow oil (47.6 g, 99%). This was recrystallised from DCM and heptane to give ethyl 3-(3'-(benzyloxy)-4-hydroxy-[1,1'-biphenyl]-2-yl)propanoate (4) as a pale yellow solid (38.47 g, 80%) in 3 crops; mp 85.7-87.2° C. $^1$H NMR (400 MHz, CDCl$_3$) δ 7.43 (m, 2H), 7.37 (m, 2H), 7.33-7.24 (m, 2H), 7.06 (d, 1H, J 8.2 Hz), 6.94 (m, 1H), 6.87 (m, 2H), 6.75 (d, 1H, 2.6 Hz), 6.70 (dd, 1H, 8.2, 2.6 Hz), 5.43 (br s, 1H), 5.07 (s, 2H), 4.06 (q, 2H, J 7.1 Hz), 2.86 (t, 2H, J 8.1 Hz), 2.39 (t, 2H, J 8.1 Hz), 1.18 (t, 3H, J 7.1 Hz). $^{13}$C NMR (100 MHz, CDCl$_3$) δ 173.7, 158.7, 155.4, 142.9, 139.5, 137.2, 134.4, 131.5, 129.4, 128.8, 128.1, 127.7, 122.4, 116.1, 115.9, 113.6, 113.5, 70.2, 60.8, 35.5, 28.6, 14.3. EIMS: m/z Found: M$^{+-}$ 376.1658, C$_{24}$H$_{24}$O$_4$ requires 376.1669. EIMS: m/z 376 (M$^{+-}$, 24%), 91 (100).

Production of 3-(3'-Benzyloxy-4-hydroxy-[1,1'-biphenyl]-2-yl)propanamide (5)

Ethyl 3-(3'-(benzyloxy)-4-hydroxy-[1,1'-biphenyl]-2-yl) propanoate (4) (30.0 g, 79.80 mmol), methanol (150 mL) and 30% aqueous ammonia (450 mL) were stirred at ambient temperature for 1 week. The resultant solid was collected by filtration. The crude material was recrystallised from DCM and heptane to give 3-(3'-(benzyloxy)-4-hydroxy-[1,1'-biphenyl]-2-yl)propanamide (5) as colourless square plates (12.8 g, 46%); mp 119.5-120.5° C. $^1$H NMR (400 MHz, DMSO-d$_6$) δ 9.39 (br s, 1H), 7.46 (m, 2H), 7.39 (t, 2H, J 7.1 Hz), 7.31 (q, 2H, J 7.6 Hz), 7.23 (br s, 1H), 6.96 (m, 2H), 6.87 (m, 1H), 6.83 (d, 1H, J 7.6 Hz), 6.73 (br s, 1H), 6.71 (d, 1H, J 2.4 Hz), 6.64 (dd, 1H, J 8.2, 2.5 Hz), 5.12 (s, 2H), 2.67 (t, 2H, J 7.7 Hz), 2.21 (t, 2H, J 7.7 Hz). $^{13}$C NMR (100 MHz, DMSO-d$_6$) δ 175.4, 158.7, 155.9, 143.0, 139.3, 137.2, 133.9, 131.6, 129.5, 128.8, 128.2, 127.7, 122.3, 116.3, 116.2, 113.8, 113.6, 70.2, 36.8, 29.2. EIMS: m/z Found: M$^{+-}$ 347.1515, C$_{22}$H$_{21}$NO$_3$ requires 347.1516. EIMS: m/z 347 (M$^{+-}$, 19%), 91 (100).

Production of 2-(3-Amino-3-oxopropyl)-3'-(benzyloxy)-[1,1'-biphenyl]-4-yl trifluoromethansulfonate (6)

To a mixture of 3-(3'-(benzyloxy)-4-hydroxy-[1,1'-biphenyl-2-yl)propanamide (5) (8.0 g, 21.0 mmol) in DCM (100 mL) was added N-phenyltriflamide (8.21 g, 23.0 mmol), followed by triethylamine (3.2 mL, 23.0 mmol). The reaction mixture was stirred at ambient temperature for 20 hours, then transferred to a separating funnel, washed with water (2×) and brine, then concentrated to give a tan oil. The crude oil was pre-absorbed onto Celite, then chromatographed (DCVC) eluting with a gradient of ethyl acetate in DCM (0-25% ethyl acetate). Like fractions were combined and recrystallised from DCM and heptane to give 2-(3-amino-3-oxopropyl)-3'-(benzyloxy)-[1,1'-biphenyl]-4-yl trifluoromethanesulfonate (6) as colourless needles (10.73 g, 65%); mp 104.0-106.0° C. $^1$H NMR (400 MHz, CDCl$_3$) δ

7.41-7.27 (m, 6H), 7.23 (d, 1H, J 8.2 Hz), 7.17 (d, 1H, J 2.6 Hz), 7.11 (dd, 1H, J 8.4, 2.6 Hz), 6.98 (m, 1H), 6.82 (m, 2H), 5.57 (brs, 1H), 5.16 (br s, 1H), 5.06 (s, 2H), 2.89 (t, 2H, J 7.9 Hz), 2.21 (t, 2H, J 7.9 Hz). $^{13}$C NMR (100 MHz, CDCl$_3$) δ 173.9, 158.9, 148.9, 142.2, 141.2 (two signals coincident), 136.9, 132.0, 129.8, 128.8, 128.3, 127.7, 122.0, 121.8, 119.2, 118.9 (d, J320.6 Hz) 115.8, 114.4, 70.2, 36.3, 28.8. EIMS: m/z Found: M$^{+-}$ 479.1004, C$_{23}$H$_{20}$F$_3$NO$_5$$^{32}$S requires 479.1009. EIMS: m/z 479 (M$^{+-}$, 7%), 91 (100).

Production of 2-(3-Amino-3-oxopropyl)-3'-hydroxy-[1,1'-biphenyl]-4-yl trifluoromethansulfonate (7)

2-(3-Amino-3-oxopropyl)-3'-(benzyloxy)-[1,1'-biphenyl]-4-yl trifluoromethanesulfonate (6) (10.29 g, 22.0 mmol) and thioanisole (5.05 mL, 43.0 mmol) in trifluoroacetic acid (10 mL) was stirred at ambient temperature in a stoppered flask for 2 days. The reaction mixture was cooled in an ice bath then poured onto iced water and transferred to a separating funnel. The product was extracted with ethyl acetate. The organic phase was washed with water and brine and concentrated to dryness. The crude material was pre-absorbed onto Celite, then chromatographed (DCVC) eluting with a gradient of DCM in heptane (50, 75 and 100% DCM) followed by a gradient of methanol in DCM (1-5% methanol). Fractions containing clean material were combined and concentrated, then recrystallised from methanol and 1,2-dichloroethane to give 2-(3-amino-3-oxopropyl)-3'-hydroxy-[1,1'-biphenyl]-4-yl trifluoromethanesulfonate (7) as colourless needles (6.19 g, 74%); mp 126.2-127.3° C. $^1$H NMR (400 MHz, DMSO-d$_6$) δ 9.60 (s, 1H), 7.42 (s, 1H), 7.38-7.20 (m, 4H), 6.86-6.66 (m, 4H), 2.80 (t, 2H, J 8.1 Hz), 2.28 (t, 2H, J 8.1 Hz). $^{13}$C NMR (100 MHz, DMSO-d$_6$) δ 173.0, 157.3, 148.3, 142.2, 141.9, 140.7, 131.7, 129.5, 121.4, 119.6, 118.8, 116.7, 115.8, 114.6, 35.5, 28.0. EIMS: m/z Found: M$^{+-}$ 389.0533, C$_{16}$H$_{14}$F$_3$NO$_2$$^{32}$S requires 389.0539. EIMS: m/z 389 (M$^{+-}$, 32%), 211 (60), 197 (100).

Production of 3-(3'-Hydroxy-4-(pyridin-3-yl)-[1,1'-biphenyl]-2-yl)propanamide (P5)

A mixture of 2-(3-amino-3-oxopropyl)-3'-hydroxy-[1,1'-biphenyl]-4-yl trifluoromethanesulfonate (7) (0.50 g, 1.29 mmol), pyridine-3-boronic acid (0.20 g, 1.60 mmol) and aqueous sodium carbonate (1M) (3.0 mL, 3.0 mmol) in toluene (10 mL) and ethanol (2 mL) was degassed with nitrogen for 10 minutes. Tetrakis(triphenylphosphine)palladium(0) (0.10 g, 0.09 mmol) was added and the reaction mixture heated in a sealed vessel at 85° C. until all the triflate starting material had been consumed. The reaction mixture was cooled to ambient temperature than partitioned between 2M hydrochloric acid and ethyl acetate. The layers were separated. The organic layer was checked by TLC and found to contain very little desired product and was discarded. The aqueous layer was basified and re-extracted with ethyl acetate (2×). The combined organic layers were washed with water and brine and concentrated to dryness to give a cream solid (260 mg). The crude material was pre-absorbed onto Celite, then chromatographed (DCVC) eluting with a gradient of methanol in DCM (0-10% methanol). The fractions containing clean material were combined and recrystallised from DCM and methanol to give 3-(3'-hydroxy-4-(pyridine-3-yl)-[1,1'-biphenyl]-2-yl)propanamide (P5) as a colourless solid (0.09 g, 21%); mp 196-198° C. $^1$H NMR (400 MHz, DMSO-d$_6$) δ 9.55 (s, 1H), 8.92 (m, 1H), 8.58 (m, 1H), 8.10 (m, 1H), 7.67 (m, 1H), 7.59 (dd, 1H, J 2.0, 7.9 Hz), 7.50 (m, 1H), 7.25 (m, 3H), 6.78 (m, 4H), 2.84 (m, 2H), 2.33 (m, 2H). $^{13}$C NMR (100 MHz, DMSO-d$_6$) δ 173.4, 157.1, 148.4, 147.6, 141.9, 141.3, 139.4, 136.0, 135.4, 134.0, 130.4, 129.3, 127.4, 124.3, 123.8, 119.6, 115.8, 114.1, 36.1, 28.1. EIMS: m/z Found: M$^{+-}$ 318.1358, C$_{20}$H$_{18}$N$_2$O$_2$ requires 318.1363. EIMS: m/z 318 (M$^{+-}$, 92%), 273 (38), 259 (100). HPLC purity (40% ACN/H$_2$O, 264 nm): 98.90%.

Production of 3-(3'-Hydroxy-4-(thiophen-3-yl)-[1,1'biphenyl]-2-yl)propanamide (P8)

Prepared according to the method of P5 from 2-(3-amino-3-oxopropyl)-3'-hydroxy-[1,1'-biphenyl]-4-yl trifluoromethanesulfonate (7) (0.32 g, 0.82 mmol), thiophene-3-boronic acid (0.132 g, 1.03 mmol), tetrakis(triphenylphosphine)palladium(0) (0.056 g, 0.05 mmol) and aqueous sodium carbonate (1M) (2.0 mL, 2.0 mmol) in toluene (10 mL) and ethanol (2 mL). The crude material was purified by chromatography (DCVC) eluting with a gradient of methanol in DCM (0-5% methanol). The fractions containing clean material were combined and recrystallised from DCM and methanol to give 3-(3'-hydroxy-4-(thiophen-3-yl)-[1,1'biphenyl]-2-yl)propanamide (P8) as a beige solid (0.13 g, 50%); mp 211-212° C. $^1$H NMR (400 MHz, DMSO-d$_6$) δ 9.50 (s, 1H), 7.88-7.84 (m, 1H), 7.68-7.63 (m, 2H), 7.59-7.54 (m, 2H), 7.27-7.19 (m, 2H), 7.16 (d, 1H, J 7.9 Hz), 6.80-6.68 (m, 4H), 2.80 (t, 2H, J 7.9 Hz), 2.30 (t, 2H, J 7.9 Hz). $^{13}$C NMR (100 MHz, DMSO-d$_6$) δ 173.4, 157.1, 142.2, 141.3, 140.2, 139.0, 134.2, 130.1, 129.3, 127.0, 126.6, 126.2, 123.7, 120.8, 119.7, 115.8, 113.9, 36.2, 28.2. EIMS: m/z Found: M$^{+-}$ 323.0964, C$_{19}$H$_{17}$NO$_2$$^{32}$S requires 323.0975. EIMS: m/z 323 (M$^{+-}$, 100%), 305 (36), 277 (53), 264 (64). HPLC purity (40% ACN/H$_2$O, 274 nm): 99.78%.

Production of 3-(4-(Furan-3-yl)-3'-hydroxy-[1,1'-biphenyl]-2-yl)propanamide (P11)

Prepared according to the method of P5 from 2-(3-amino-3-oxopropyl)-3'-hydroxy-[1,1'-biphenyl]-4-yl trifluoromethanesulfonate (7) (0.50 g, 1.29 mmol), furan-3-boronic acid (0.18 g, 1.60 mmol), tetrakis(triphenylphosphine) palladium(0) (0.10 g, 0.09 mmol) and aqueous sodium carbonate (1M) (2.5 mL, 2.50 mmol) in toluene (10 mL) and ethanol (2 mL). The crude material was purified by chromatography (DCVC) eluting with a gradient of methanol in DCM (0-10% methanol) and then recrystallised from DCM and methanol to give 3-(4-(furan-3-yl)-3'-hydroxy-[1,1'-biphenyl]-2-yl)propanamide (P11) as beige rods (0.23 g, 58%); mp 191-192° C. $^1$H NMR (400 MHz, DMSO-d$_6$) δ 9.49 (s, 1H), 8.20-8.16 (m, 1H), 7.78-7.73 (m, 1H), 7.58-7.54 (m, 1H), 7.49-7.44 (m, 1H), 7.26-7.18 (m, 2H), 7.14 (d, 1H, J 7.9 Hz), 6.99-6.94 (m, 1H), 6.80-6.67 (m, 4H), 2.79 (t, 2H, J 8.3 Hz), 2.29 (t, 2H, J 8.3 Hz). $^{13}$C NMR (100 MHz, DMSO-d$_6$) δ 173.4, 157.1, 144.3, 142.2, 140.1, 139.2, 139.0, 130.9, 130.0, 129.2, 126.0, 125.6, 123.1, 119.6, 115.8, 113.9, 108.7, 36.1, 28.1. EIMS: m/z Found: M$^{+-}$ 307.1204, C$_{19}$H$_{17}$NO$_3$ requires 307.1203. EIMS: m/z 307 (M$^{+-}$, 100%), 248 (50). HPLC purity (40% ACN/H$_2$O, 265 nm): 99.33%.

Production of 3-(3'-Hydroxy-4-(1H-pyrazol-4-yl)-[1,1'-biphenyl]-2-yl)propanamide (P22)

Prepared according to the method of P5 from 2-(3-amino-3-oxopropyl)-3'-hydroxy-[1,1'-biphenyl]-4-yl trifluoromethanesulfonate (7) (0.50 g, 1.29 mmol), tert-butyl 4-(4,4,5,5-tetramethyl-1,3,2-dioxaborolan-2-yl)-1H-pyrazole-1-carboxylate (0.47 g, 1.61 mmol), tetrakis (triphenylphosphine)palladium(0) (0.10 g, 0.09 mmol) and aqueous sodium carbonate (1M) (3.0 mL, 3.00 mmol) in toluene (10 mL) and ethanol (2 mL). The crude material was purified by chromatography (DCVC) eluting with a gradient of methanol in DCM (0-20% methanol). The material was further purified by radial chromatography eluting with a gradient of ethyl acetate in DCM (50-100% ethyl acetate) and then a gradient of methanol in ethyl acetate (1-5% methanol) to give 3-(3'-hydroxy-4-(1H-pyrazol-4-yl)-[1,1'-biphenyl]-2-yl)propanamide (P22) as beige crystals (0.10 g, 26%); mp 161.5-163.2° C. $^1$H NMR (400 MHz, DMSO-d$_6$) δ 12.95 (s, 1H), 9.44 (s, 1H), 8.13 (br s, 1H), 7.99 (br s, 1H), 7.58-7.54 (m, 1H), 7.49-7.42 (m, 1H), 7.28-7.19 (m, 2H), 7.10 (d, 1H, J 7.9 Hz), 6.79-6.67 (m, 4H), 2.78 (t, 2H, J 7.9 Hz), 2.29 (t, 2H, J 7.9 Hz), $^{13}$C NMR (100 MHz, DMSO-d$_6$) δ 173.6, 157.1, 142.4, 139.0, 138.9, 136.3, 131.9, 130.1, 129.2, 125.5 (two signals coincident), 122.8, 121.0, 119.7, 115.9, 113.8, 36.2, 28.2. EIMS: m/z Found: M$^{+-}$ 307.1314 C$_{18}$H$_{17}$N$_3$O$_2$ requires 307.1315, EIMS: m/z 307 (M$^{+-}$, 100%), 248 (57). HPLC purity (35% ACN/0.1% TFA, 270 nm): 99.08%.

Production of 3-(3'-Hydroxy-4-(pyrimidin-5-yl)-[1,1-biphenyl]-2-yl)propanamide (P26)

Prepared according to the method of P5 from 2-(3-amino-3-oxopropyl)-3'-hydroxy-[1,1'-biphenyl]-4-yl trifluoromethanesulfonate (7) (1.00 g, 2.58 mmol), pyrimidine-5-boronic acid (0.40 g, 3.20 mmol), tetrakis(triphenylphosine)palladium(0) (0.20 g, 0.18 mmol) and aqueous sodium carbonate (1M) (6.0 mL, 6.00 mmol) in toluene (20 mL) and ethanol (4 mL). The crude material was purified by chromatography (DCVC) (×2) eluting with a gradient of methanol in DCM (0-7.5% methanol) and then recrystallised from methanol to give 3-(3'-hydroxy-4-pyrimidin-5-yl)-[1,1-biphenyl]-2-yl)propanamide (P26) as a pale lemon solid (0.17 g, 20%); mp 191.9-193.5° C. $^1$H NMR (400 MHz, DMSO-d$_6$) δ 9.56 (s, 1H), 9.20 (s, 1H), 9.17 (s, 2H), 7.77-7.75 (m, 1H), 7.69-7.66 (m, 1H), 7.32-7.22 (m, 2H), 7.25 (br s, 1H), 6.81-6.71 (m, 4H), 2.87-2.80 (m, 2H), 2.37-2.13 (m, 2H). $^{13}$C NMR (100 MHz, DMSO-d$_6$) δ 173.4, 157.24, 157.18, 154.7 (two signals coincident), 142.1, 141.7, 139.6, 133.1, 132.7, 130.5, 129.3, 127.4, 124.4, 119.6, 115.8, 114.2, 36.0, 28.1. EIMS: m/z Found: M$^{+-}$ 319.1310, C$_{19}$H$_{17}$N$_3$O$_2$ requires 319.1315. EIMS: m/z 319 (M$^{+-}$, 70%), 274 (48), 260 (100). HPLC purity (40% ACN/H$_2$O, 265 nm): 99.87%.

Production of 5-Bromo-2,4-dimethylthiazole (8)

To a vigorously stirred mixture of 2,4-dimethylthiazole (23.37 g, 0.207 mol) and calcium carbonate (26.90 g 270 mmol) in DCM (200 mL) was added slowly a solution of bromine (11.10 mL, 217 mmol) in DCM (100 mL). The reaction was checked after 3 hours by TLC (DCM) and was not complete. A further two portions of bromine (2×3.00 ml, 117.10 mmol) in DCM (2×20 mL) was required for the reaction to go to completion. Sodium metabisulphite (16.0 g, 84.17 mmol) in water (60 mL) was added slowly to the reaction mixture. More water was added and the reaction mixture was transferred to a separating funnel. The layers were separated and the aqueous extracted once more with DCM. The combined organic layers were washed with 1M sodium carbonate solution (2×) and water and concentrated to give 5-bromo-2,4-dimethylthiazole (8) as a pale tan oil (38.40 g, 97%). $^1$H NMR (400 MHz, CDCl$_3$) δ 2.51 (s, 3H), 2.24 (s, 3H).

Production of 2,4-Dimethyl-5-(4,4,5,5-tetramethyl-1,3,2-dioxaborolan-2-yl)thiazole (9)

A solution of 5-bromo-2,4-dimethylthiazole (8) (5.00 g, 26.0 mmol) and 1,2-dibromoethane (0.24 g, 1.3 mmol) in THF (20 mL) was added dropwise to a flask containing magnesium turnings (0.65 g, 26.8 mmol) over a one hour period. The reaction mixture was heated to 75° C. for 4 hours, cooled to ambient temperature then transferred to a dropping funnel via a cannula on a second reaction flask. The Grignard reagent was then added dropwise to a solution of isopropylpinacolborate (5.30 mL, 26.00 mmol) in THF (10 mL) at 0° C. After addition was complete, the reaction mixture was warmed up to ambient temperature and was stirred for 20 hours. The reaction was cooled to −10° C., and then slowly acetic acid (1.03 mL, 25.50 mmol) was added so that the reaction mixture was at pH 7. Solvent was removed by rotary evaporation then ethyl acetate was added and also removed by rotary evaporation. The crude oil was preabsorbed onto Celite then chromatographed (DCVC) eluting with a gradient of ethyl acetate in heptane (0-30% ethyl acetate). Fractions containing the desired material were combined and concentrated to give 2,4-dimethyl-5-(4,4,5,5-tetramethyl-1,3,2-dioxaborolan-2-yl)thiazole (9) as a pale yellow oil which solidified (1.65 g, 26%). $^1$H NMR (400 MHz, DMSO-d$_6$) δ 2.63 (s, 3H), 2.53 (s, 3H), 1.26 (s, 12H), $^{13}$C NMR (50 MHz, DMSO-d$_6$) δ 170.4, 163.2, 84.1, 24.9, 19.1, 17.6 (one signal not observed). EIMS: m/z Found: M$^{+-}$ 239.1143, C$_{11}$H$_{18}$NO$_2$$^{11}$B$^{32}$S requires 239.1146. EIMS: m/z 239 (M$^{+-}$, 66%), 224 (45), 182 (37), 139 (53), 71 (100).

Production of 3-(4-(2,4-Dimethylthiazol-5-yl)-3'-hydroxy-[1,1'biphenyl]-2-yl)propanamide (P40)

Prepared according to the method of P5 from 2-(3-amino-3-oxopropyl)-3'-hydroxy-[1,1'-biphenyl]-4-yl trifluoromethanesulfonate (7) (1.00 g, 2.58 mmol), 2,4-dimethyl-5-(4,4,5,5-tetramethyl-1,3,2-dioxaborolan-2-yl)thiazole (0.76 g, 3.20 mmol), tetrakis(triphenylphosphine)palladium(0) (0.24 g, 0.21 mmol) and aqueous sodium carbonate (1M) (6.0 ml, 6.00 mmol) in toluene (20 mL) and ethanol (4 ml). The crude material was purified by chromatography (DCVC) eluting with a gradient of methanol in dichloromethane (0-5% methanol) and then recrystallised from methanol to give 3-(4-(2,4-dimethylthiazol-5-yl)-3'-hydroxy-[1,1-biphenyl]-2-yl)propanamide (P40) as yellow crystals (0.23 g, 26%); mp 196.6-199.4° C. $^1$H NMR (400 MHz, DMSO-d$_6$) δ 9.54 (s, 1H), 7.38 (s, 1H), 7.32-7.19 (m, 4H), 6.81-6.69 (m, 4H), 2.80 (t, 2H, J 7.8 Hz), 2.63 (s, 3H), 2.42 (s, 3H), 2.27 (t, 2H, J 7.8 Hz). $^{13}$C NMR (100 MHz, DMSO-d$_6$) δ 173.3, 162.5, 157.2, 146.7, 141.8, 140.8, 139.2, 130.7, 130.4, 130.1, 129.3, 129.1, 126.2, 119.6, 115.8, 114.1, 35.9, 27.9, 18.7, 16.0. EIMS: m/z Found: M$^{+-}$ 352.1230, C$_{20}$H$_{20}$N$_2$O$_2$$^{32}$S requires 352.1240. EIMS: m/z 352 (M$^{+-}$, 100%), 334 (41), 293 (35), HPLC purity (35% ACN/0.1% TFA, 256 nm): 98.64%.

Production of 3-(4-(3,5-Dimethylisoxazol-4-yl)-3'-hydroxy-[1,1'-biphenyl]-2-yl)propanamide (P41)

Prepared according to the method of P5 from 2-(3-amino-3-oxopropyl)-3'-hydroxy-[1,1'-biphenyl]-4-yl trifluoromethanesulfonate (7) (0.50 g, 1.29 mmol), 3,5-dimethylisoxazole-4-boronic acid (0.23 g, 1.60 mmol), tetrakis(triphenylphosine)palladium(0) (0.10 g, 0.09 mmol) and aqueous sodium carbonate (1M) (2.5 mL, 2.50 mmol) in toluene (10 mL) and ethanol (2 mL). The crude material was purified by chromatography (DCVC) eluting with a gradient of methanol in DCM (0-5% methanol) and then recrystallised from DCM and methanol to give 3-(4-(3,5-dimethyl-isoxazol-4-yl)-3'-hydroxy-[1,1'-biphenyl]-2-yl)propanamide (P41) as a pale lemon solid (0.15 g, 33%); mp 203-204° C. $^{1}$H NMR (400 MHz, DMSO-d$_{6}$) δ 9.52 (s, 1H), 7.32-7.30 (m, 1H), 7.28-7.20 (m, 4H), 6.81-6.70 (m, 4H), 2.52-2.49 (m, 2H), 2.44 (s, 3H), 2.32-2.25 (m, 2H), 2.27 (s, 3H), $^{13}$C NMR (50 MHz, DMSO-d$_{6}$) δ 173.3, 165.1, 158.2, 157.1, 142.0, 140.5, 139.0, 130.0, 129.3, 129.2, 128.8, 126.2, 119.6, 115.8, 115.7, 114.0, 35.9, 27.9, 11.4, 10.6, EIMS: m/z Found: M$^{+-}$ 336.1459, C$_{19}$H$_{17}$N$_{3}$O$_{2}$ requires 336.1468. EIMS: m/z Found: M$^{+-}$ 336.1459, C$_{20}$H$_{2}$N$_{2}$O$_{3}$ requires 336.1468. EIMS: m/z 336 (M$^{+-}$, 86%), 292 (100). HPLC purity (40% ACM/H$_{2}$O, 275 nm): 97.36%.

Example 2: Synthesis of P9

Figure 3:
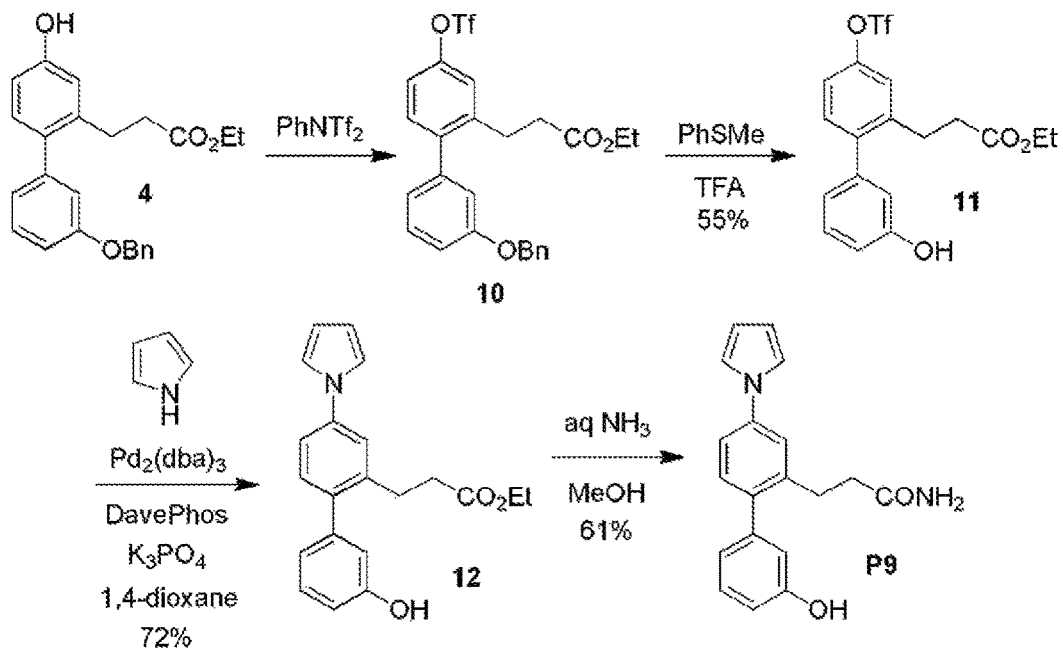
FIG. 3: Synthesis scheme for P9.

The synthetic route used to prepare P5, P8, P11, P22, P26, P40 and P41 is shown in FIG. 3. Briefly, aryl triflate ester (11), was prepared from biphenyl ester (4) by reaction with N-phenyltriflamide to generate protected aryl triflate (10), followed by treatment with thioanisole/TFA. A palladium-catalysed cross-coupling reaction between aryl triflate ester (11) and pyrrole then afforded the desired teraryl compound (12), which underwent aminolysis to produce P9.

Production of Ethyl 3-(3'-(benzyloxy)-4-(((trifluoromethyl)sulfonyl)oxy)-[1,1'-biphenyl]-2-yl)propanoate (10)

Prepared according to the method used to generate compound 6; from ethyl 3-(3'-(benzyloxy)-4-hydroxy-[1,1-biphenyl]-2-yl)propanoate (4) (8.0 g, 21.00 mmol), N-phenyltriflamide (8.21 g, 23.00 mmol) and triethylamine (3.2 ml, 23.00 mmol) in (100 mL). The crude material was purified by passing it through a plug of silica gel, eluting with to give ethyl 3-(3'-(benzyloxy)-4-(((trifluoromethyl)sulfonyl)oxy)-[1,1'-biphenyl]-2-yl)propanoate (10) as a yellow oil (quantitative yield) with sufficient purity to be used in the next step. $^{1}$H NMR (400 MHz, DMSO-d$_{6}$) δ 7.46-7.23 (m, 7H), 7.20-7.11 (m, 2H), 7.02-6.97 (m, 1H), 6.88-6.83 (m, 2H), 5.08 (s, 2H), 4.06 (q, 2H, J 7.2 Hz), 2.90 (t, 2H, J 7.9 Hz), 2.39 (t, 2H, J 7.9 Hz), 1.18 (t, 3H, J 7.2 Hz), $^{13}$C NMR (100 MHz, DMSO-d$_{6}$) δ 172.6, 158.9, 148.9, 142.4, 141.2, 141.1, 137.0, 132.0, 129.8, 128.8, 128.3, 127.7, 123.7, 121.9, 121.8, 119.1, 115.8, 114.4, 70.3, 60.8, 34.9, 28.4, 14.3. EIMS: m/z Found: M$^{+-}$ 508.1160, C$_{25}$H$_{23}$F$_{3}$O$_{6}$$^{32}$S requires 508.1162, EIMS: m/z 508 (M+10%), 91 (100).

Production of Ethyl 3-(3'-hydroxy-4-(((trifluoromethyl)sulfonyl)oxy)-[1,1'-biphenyl]-2-yl)propanoate (11)

Prepared according to the method used to generate compound 7; from ethyl 3-(3'-(benzyloxy)-4-(((trifluoromethyl)sulfonyl)oxy)-[1,1'-biphenyl]-2-yl) propionate (10) (10.67 g, 21.0 mmol) and thioanisole (5 mL, 42.62 mmol) in TFA (10 mL). The crude material was pre-absorbed onto Celite, then chromatographed (DCVC) eluting with a gradient of DCM in heptane (50-100% DCM), followed by recrystallisation from DCM and heptane to give ethyl 3-(3'-hydroxy-4-(((trifluoromethyl)sulfonyl)oxy)-[1,1'-biphenyl]-2-yl)propanoate (11) as colourless prisms (4.84 g, 55%); mp 90.8-91.9° C., $^{1}$H NMR (400 MHz, DMSO-d$_{6}$) δ 7.30-7.23 (m, 2H), 7.19-7.11 (m, 2H), 6.87-6.78 (m, 2H), 6.78-6.73 (m, 1H), 5.73 (s, 1H), 4.07 (q, 2H, J 7.2 Hz), 2.95 (t, 2H, J 7.9 Hz), 2.44 (t, 2H, J 7.9 Hz), 1.19 (t, 3H, J 7.2 Hz). $^{13}$C NMR (100 MHz, DMSO-d$_{6}$) δ 173.0, 155.9, 148.9, 142.2, 141.3, 140.9, 132.0, 130.0, 121.8, 121.6, 119.0 (q, J=321.2 Hz) 119.2, 116.2, 115.0, 61.1, 35.1, 28.5, 14.3. EIMS: m/z Found: M$^{+-}$ 418.0690, C$_{18}$H$_{17}$F$_{3}$O$_{6}$$^{32}$S requires 418.0692. EIMS: m/z 418 (M$^{+-}$, 100%), 373 (38), 211 (61), 197 (82).

Production of Ethyl 3-(3'-hydroxy-4-(1H-pyrrol-1-yl)-[1,1'-biphenyl]-2-yl)propanoate (12)

An oven-dried μW vial (2-5 mL) containing 1,4-dioxane (4.5 mL) was degassed for 10 min, after which Pd$_{2}$(dba)$_{3}$ (0.07 mmol, 66 mg), 2-dicyclohexylphosphino-2'-(N,N-dimethylamino)biphenyl (DavePhos) (0.07 mmol, 28 mg) and K$_{3}$PO$_{4}$ (1.1 mmol, 228 mg) was added and allowed to stir for 20 minutes. Ethyl 3-(3'-hydroxy-4-(((trifluoromethyl)sulfonyl)oxy-[1,1'-biphenyl]-2-yl)propanoate (11) (300 mg, 0.72 mmol) and pyrrole (4.30 mmol, 298 μL) was then added, the vial sealed, and the reaction mixture heated at 100° C. for 16 h. The solvent was evaporated and the residue was filtered through a small column of silica, eluting with 3:7 ethyl acetate:PE. Following evaporation of the solvent, the residue was purified by DCVC eluting with 5:95 ethyl acetate: PE→1:4 ethyl acetate:PE to afford ethyl 3-(3'-hydroxy-4-(1H-pyrrol-1-yl)-[1,1'-biphenyl]-2-yl)propanoate (12) as a yellow oil (159 mg, 72%). $^{1}$H NMR (400 MHz, MeOH-d$_{4}$) δ 7.39 (m, 1H), 7.36 (dd, 1H, J 8.4, 2.4 Hz), 7.30-7.18 (m, 4H), 6.84-6.72 (m, 3H), 6.28 (m, 2H), 4.02 (q, 2H, J 7.1 Hz), 2.97 (m, 2H), 2.45 (m, 2H), 1.14 (t, 3H, J 7.1 Hz). $^{13}$C NMR (100 MHz, MeOH-d$_{4}$) δ 174.7, 158.6, 143.7, 141.4, 140.9, 140.8, 132.4, 130.6, 121.8, 121.6, 120.1, 118.9, 117.3, 117.1, 111.5, 61.7, 36.2, 29.8, 14.6. EIMS: m/z Found: M$^{+-}$ 335.1510, C$_{21}$H$_{21}$NO$_{3}$ requires 335.1516. EIMS: m/z 335 (M$^{+-}$, 100%).

Production of 3-(3'-Hydroxy-4-(1H-pyrrol-1-yl)-[1,1'-biphenyl]-2-yl)propanamide (P9)

Ethyl 3-(3'-hydroxy-4-(1H-pyrrol-1-yl)-[1,1'-biphenyl]-2-yl)propanoate (12) (145 mg, 0.43 mmol) was dissolved in methanol (4 mL), to which 30% aqueous ammonia (2.5 mL) was added and the reaction mixture allowed to stir at rt for 16 h. Additional ammonia (1 mL) was then added, followed by a further addition (1 mL) after 24 h. Continued stirring for an additional 16 h was followed by the addition of ethyl acetate (20 mL) and water (20 mL). The mixture was partitioned, and the organic phase dried and the solvent evaporated. The residue was dissolve in hot methanol, decolourising charcoal added, and the reaction filtered through a warm filter paper to afford a clear solution. After a time a solid formed which was collected and washed with cold methanol to afford 3-(3'-hydroxy-4-(1H-pyrrol-1-yl)-[1,1'-biphenyl]-2-yl)propanamide (P9) as white crystals (81 mg, 61%); mp 221-224° C. $^{1}$H NMR (400 MHz, DMSO-d$_{6}$) δ 9.52 (br s, 1H); 7.50 (m, 1H), 7.42 (dd, 1H, J 2.4, 8.4 Hz), 7.36 (m, 2H), 7.25-7.19 (m, 3H), 6.79-6.69 (m, 4H), 6.28 (m, 2H), 2.80 (m, 2H), 2.31 (m, 2H). $^{13}$C NMR (100 MHz, DMSO-d$_{6}$) δ 173.3, 157.1, 141.7, 140.1, 139.0, 138.5, 130.7, 129.3, 119.7 (two signals coincident), 118.9, 116.9, 115.9, 114.0, 110.4, 35.9, 28.2. EIMS: m/z Found: M$^{+-}$ 306.1355, C$_{19}$H$_{18}$N$_{2}$O$_{2}$ requires 306.1363. EIMS: m/z 306 (M$^{+-}$, 28%), 288 (100). HPLC purity (35% ACN/0.1% TFA, 270 nm): 99.33%.

Figure 4:
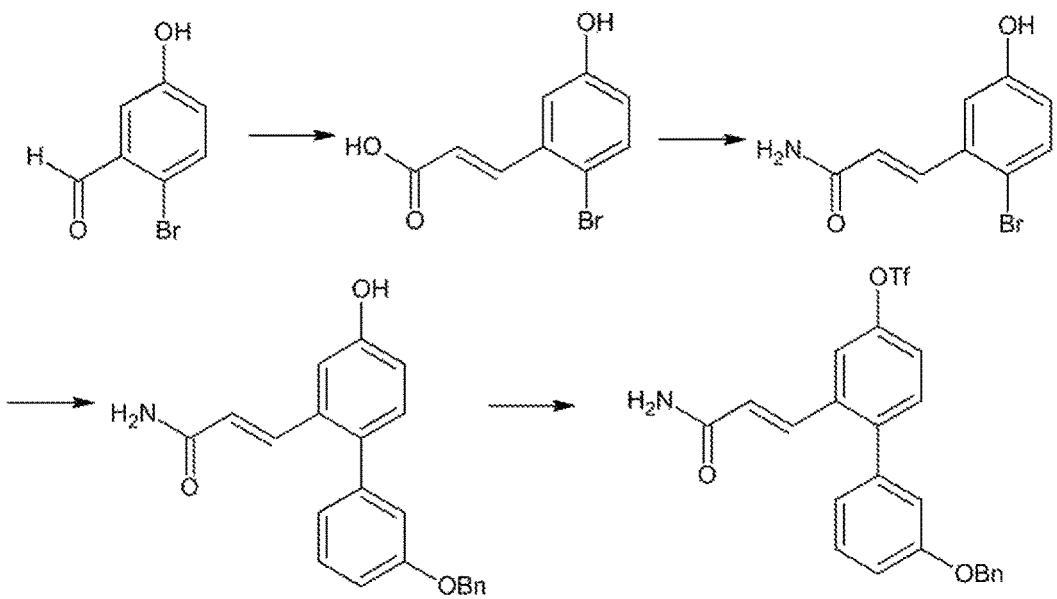
FIG. 4: Synthesis scheme for (2E)-3-[3'-(Benzyloxy)-4-trifluoromethane sulfonate-biphenyl-2-yl]prop-2-enamide.

Example 3: Synthesis of Intermediate (2E)-3-[3'-(Benzyloxy)-4-trifluoromethane sulfonate-biphenyl-2-yl]prop-2-enamide The synthetic route used to prepare intermediate (2E)-3-[3'-(Benzyloxy)-4-trifluoromethanesulfonate-biphenyl-2-yl]prop-2-enamide is shown in FIG. 4.

Preparation of (2E)-3-(2-Bromo-5-hydroxyphenyl)prop-2-enoic Acid

Piperidine (1.47 mL) was added to a mixture of 4-bromo-3-formyl-phenol (25.0 g, 0.124 mol) and malonic acid (15.53 g, 0.149 mol) in pyridine (150 mL) and heated to reflux for 4 h. The reaction mixture was cooled briefly before adding hydrochloric acid (2 M, 500 mL) and acidified to pH 1-2 with concentrated hydrochloric acid (33%, ca. 50-100 mL). The suspension was cooled to approximately 10° C. and the solid collected by vacuum filtration washing with hydrochloric acid (2 M, 60 mL) and dried under vacuum for 18 h. This crude material contained water and pyridine hydrochloride as indicated by $^1$H NMR, and was taken up in ethyl acetate (1.3 L) and washed with hydrochloric acid (2 M, 2×750 mL), dried over magnesium sulfate and filtered. The filtrate was concentrated to dryness to give the title compound as a grey powder (23.63 g, 0.0972 mol, 78%). $^1$H NMR (400 MHz, DMSO-d$_6$) d ppm 12.62 (br. s, 1H) 9.91 (s, 1H) 7.76 (d, J=16.0 Hz, 1H) 7.48 (d, J=8.6 Hz, 1H) 7.19 (d, J=2.3 Hz, 1H) 6.80 (dd, J=8.8, 2.5 Hz, 1H) 6.41 (d, J=16.0 Hz, 1H); HPLC (water/ACN+0.1% TFA gradient) 98.9% at 220 nm; LCMS [M+H]$^+$=242.9, [M−H]$^−$=242.0. Ca 2-5 mol % of unknown impurities as indicated by $^1$H NMR analysis.

Preparation of (2E)-3-(2-Bromo-5-hydroxyphenyl)prop-2-enamide

Oxalyl chloride (16 mL, 0.19 mol) was added over 10 min to a suspension of (2E)-3-(2-bromo-5-hydroxyphenyl)prop-2-enoic acid (23.50 g, 0.0967 mol) in dichloromethane (200 mL) and dimethylformamide (0.5 mL) at 0° C. The reaction mixture was slowly warmed to room temperature and stirred for 1 h. Additional oxalyl chloride (16 mL, 0.19 mol) was added and heated to reflux for 5 h and then stirred for 16 h at room temperature. The reaction mixture was concentrated to dryness to give the crude acid chloride intermediate.

The crude acid chloride was dissolved in 1,4-dioxane (100 mL) and poured into a solution of aqueous ammonia (28%, 68 mL, 1.12 mol) in 1,4-dioxane (200 mL). This mixture was stirred for 30 min before diluting the reaction mixture with water (500 mL). The reaction mixture was concentrated to dryness to give a grey solid. The grey solid was suspended in hydrochloric acid (1 M, 200 mL) and collected by vacuum filtration, washing with hydrochloric acid (1 M, 60 mL) and water (60 mL) then dried on the rotary evaporator (70° C.) for 45 min and then under high vacuum for 4 h to give the crude title compound (30.51 g) as a grey powder containing an unknown impurity as indicated by $^1$H NMR analysis. A portion of this material (29.6 g) was stirred in ethyl acetate (500 mL) and filtered, washing the filter cake with ethyl acetate (200 mL). The filtrates were concentrated to dryness to give the title compound as a light brown powder (21.73 g, 98%). $^1$H NMR (400 MHz, DMSO-d$_6$) d 9.89 (s, 1H) 7.63 (br. s, 1H) 7.59 (d, J=15.7 Hz, 1H) 7.45 (d, J=9.0 Hz, 1H) 7.23 (br. s, 1H) 7.06 (d, J=2.7 Hz, 1H) 6.76 (dd, J=8.6, 2.7 Hz, 1H) 6.53 (d, J=15.7 Hz, 1H); HPLC (water/ACN+0.1% TFA gradient) 95.3% at 220 nm; LCMS [M+H]$^+$=244.1, [M+Na]$^+$=264.0.

Preparation of (2E)-3-[3'-(Benzyloxy)-4-hydroxybiphenyl-2-yl]prop-2-enamide Nitrogen was bubbled through a mixture of (2E)-3-(2-bromo-5-hydroxyphenyl)prop-2-enamide (10.00 g, 41.31 mmol), 3-benzyloxy phenylboronic acid (12.22 g, 53.58 mmol) and potassium carbonate (17.34 g, 0.125 mol) in a mixture of water (60 mL), toluene (160 mL) and ethanol (100 mL) for 10 min before adding tetrakis(triphenylphosphine)palladium(0) (1.21 g, 10.5 mmol) and heating the mixture to reflux for 2.5 h. The mixture was cooled briefly, diluted with water (200 mL) and acidified by addition of hydrochloric acid (2 M, ca. 400 mL, pH: 0-1) and extracted with ethyl acetate (3×300 mL). The combined organic extracts were dried over magnesium sulfate and filtered. The filtrate was concentrated to dryness and the residue purified by flash chromotography (silica, 10-100% ethyl acetate/hexanes gradient) to give the title compound as a brown solid foam (14.37 g, 101%). $^1$H NMR (400 MHz, DMSO-d$_6$) d 9.71 (s, 1H) 7.39-7.48 (m, 4H) 7.29-7.38 (m, 4H) 7.17 (d, J=8.2 Hz, 1H) 7.09 (s, 1H) 7.06 (d, J=2.4 Hz, 1H) 7.01 (dd, J=8.2, 2.4 Hz, 1H) 6.83-6.90 (m, 2H) 6.81 (d, J=7.4 Hz, 1H) 6.49 (d, J=15.6 Hz, 1H) 5.12 (s, 2H); HPLC (water/ACN+0.1% TFA gradient) 88.2% at 220 nm; LCMS [M+H]$^+$=346.2, [M−H]$^−$=344.1. Ca 11 wt % ethyl acetate and 14 mol % of an unknown impurity as indicated by $^1$H NMR analysis.

Preparation of (2E)-3-[3'-(Benzyloxy)-4-trifluoromethanesulfonate-biphenyl-2-yl]prop-2-enamide N-Phenyl bis(trifluoro-methanesulfonamide) (16.35 g, 45.77 mmol) was added portion wise over 1 min to a solution of (2E)-3-[3'-(benzyloxy)-4-hydroxybiphenyl-2-yl]prop-2-enamide (14.27 g, 41.33 mmol) and potassium carbonate (11.63 g, 84.15 mmol) in acetonitrile (200 mL) cooled in an icebath. The reaction mix ture was warmed to room temperature and stirred vigorously for 1 h. Silica gel was added, and the mixture was concentrated and purified by flash chromatography (silica, 10-100% ethyl acetate/hexanes gradient) to give the title compound as a light brown solid foam (15.95 g, 81%). $^1$H NMR (400 MHz, DMSO-d$_6$) d 7.78 (d, J=2.4 Hz, 1H) 7.52-7.61 (m, 3H) 7.43-7.50 (m, 2H) 7.37-7.43 (m, 3H) 7.29-7.37 (m, 2H) 7.21 (br. s, 1H) 7.11 (dd, J=8.2, 2.4 Hz, 1H) 6.96-7.03 (m, 1H) 6.90 (d, J=7.4 Hz, 1H) 6.69 (d, J=15.6 Hz, 1H) 5.15 (s, 2H); HPLC (water/ACN+0.1% TFA gradient) 95.0% at 220 nm; LCMS [M+H]$^+$=478.1. Minor impurities as indicated by $^1$H NMR analysis.

Example 4: Synthesis of Intermediates of P3, P46, P47, P48, P49 and P50

Figure 5:
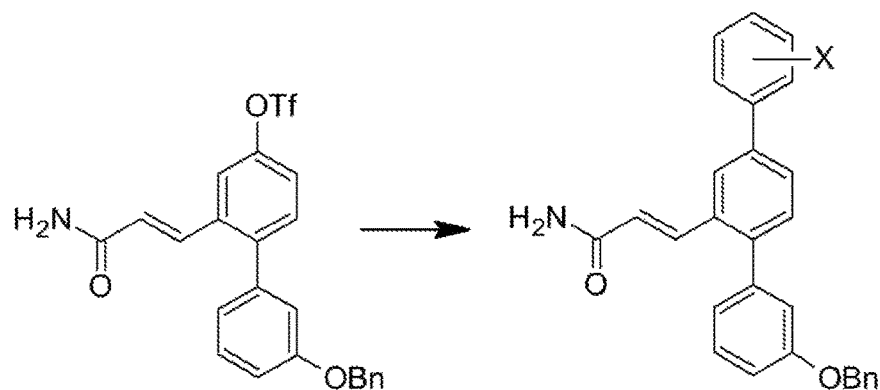
FIG. 5: Synthesis scheme for intermediates of P3, P46, P47, P48, P49 and P50.

The synthetic route used to prepare intermediates of P3, P46, P47, P48, P49 and P50 is shown in FIG. 5.

Nitrogen was bubbled through a mixture of (2E)-3-[3'-(benzyloxy)-4-trifluoromethanesulfonate-biphenyl-2-yl]prop-2-enamide (1 equiv.), a phenylboronic acid (1.3 equiv.) and potassium carbonate (3 equiv.) in a mixture of water (3 mL), toluene (8 mL) and ethanol (5 mL) for 5 min before adding tetrakis(triphenylphosphine) palladium(0) (0.1 equiv.) and heating at 80° C.-90° C. in a sealed vial or at reflux with a condenser under a nitrogen atmosphere until no (2E)-3-[3'-(benzyloxy)-4-trifluoromethanesulfonate-biphenyl-2-yl]prop-2-enamide remained by TLC, LCMS and/or HPLC. The reaction mixtures were cooled and adsorbed onto silica before purifying by flash chromatography (silica, 10-100% ethyl acetate/hexanes gradient) to give the crude desired compounds. Additional purification was required for some compounds and is described below.

The following compounds were prepared by this procedure:

3'-[(1E)-3-Amino-3-oxoprop-1-en-1-yl]-3"-benzyloxy-1,1':4',1"-terphenyl-3-carboxylic acid

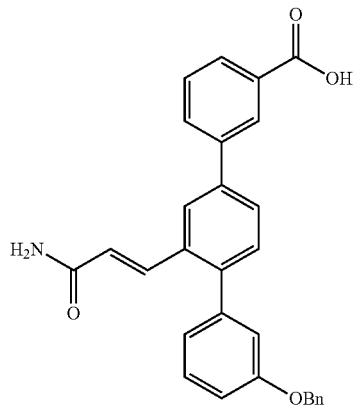 [SMILES: NC(=O)/C=C/c1cc(-c2cccc(C(=O)O)c2)ccc1-c1cccc(OCc2ccccc2)c1]

The crude title compound (243 mg) contained triphenylphosphine oxide by HPLC and LCMS analysis. The material was purified further by flash chromatography (silica, 50-100% ethyl acetate/dichloromethane gradient, followed by a 0-20% methanol/dichloromethane gradient) to give the title compound as a white powder (112 mg, 16%). $^1$H NMR (400 MHz, DMSO-$d_6$) d 13.18 (br. s, 1H) 8.26 (t, J=1.56 Hz, 1H) 7.95-8.05 (m, 3H) 7.79 (dd, J=8.22, 1.96 Hz, 1H) 7.65 (t, J=7.83 Hz, 1H) 7.53 (br. s, 1H) 7.38-7.51 (m, 7H) 7.29-7.37 (m, 1H) 7.14 (br. s, 1H) 7.06-7.12 (m, 1H) 6.97-7.03 (m, 1H) 6.90-6.96 (m, 1H) 6.77 (d, J=15.65 Hz, 1H) 5.16 (s, 2H); HPLC (water/ACN+0.1% TFA gradient) 94.5% at 220 nm; LCMS [M+H]$^+$=450.1, [M+Na]$^+$=472.1. Ca 2 wt % ethyl acetate and other minor impurities by 1H NMR analysis.

(2E)-3-(3-Benzyloxy-4"-fluoro-1,1':4',1"-terphenyl-2'-yl)prop-2-enamide

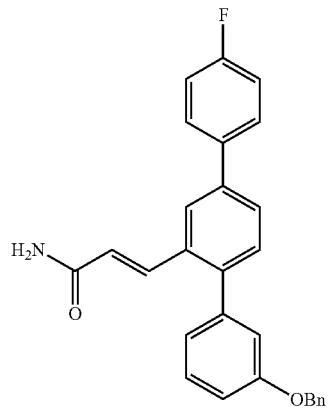 [SMILES: NC(=O)/C=C/c1cc(-c2ccc(F)cc2)ccc1-c1cccc(OCc2ccccc2)c1]

Off-white solid foam (215 mg, 32%). $^1$H NMR (400 MHz, DMSO-$d_6$) d 7.93 (d, J=1.2 Hz, 1H) 7.80 (dd, J=8.6, 5.5 Hz, 2H) 7.72 (dd, J=7.8, 657 Hz, 1H) 7.28-7.53 (m, 11H) 7.13 (br. s, 1H) 7.09 (dd, J=8.2, 2.0 Hz, 1H) 6.98 (s, 1H) 6.92 (d, J=7.4 Hz, 1H) 6.75 (d, J=16.0 Hz, 1H) 5.12-5.20 (m, 2H); HPLC (water/ACN+0.1% TFA gradient) 83.7% at 220 nm; LCMS [M+H]$^+$=424.2, [M+Na]$^+$=446.2. Ca 3% ethyl acetate and 10 mol % of other unknown impurities by $^1$H NMR analysis.

(2E)-3-(3-Benzyloxy-4"-nitro-1,1':4',1"-terphenyl-2'-yl)prop-2-enamide

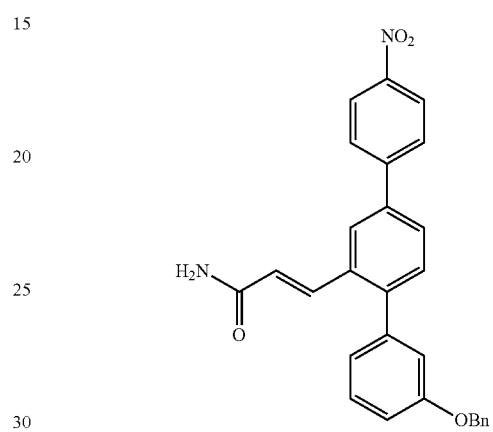

The crude title compound contained triphenylphosphine oxide and (2E)-3-[3'-(benzyloxy)biphenyl-2-yl]prop-2-enamide by HPLC and LCMS analysis. Further purification by two flash chromatographic separations (silica, 50-100% ethyl acetate/dichloromethane gradient) gave the title compound as a yellow powder (158 mg, 22%). $^1$H NMR (400 MHz, DMSO-$d_6$) d 8.36 (d, J=8.6 Hz, 2H) 8.07 (m, J=8.6 Hz, 3H) 7.87 (dd, J=8.0, 1.4 Hz, 1H) 7.53 (d, J=8.2 Hz, 1H) 7.44-7.51 (m, 4H) 7.41 (s, 3H) 7.34 (s, 1H) 7.15 (br. s, 1H) 7.11 (dd, J=8.2, 1.96 Hz, 1H) 7.00 (s, 1H) 6.94 (d, J=7.4 Hz, 1H) 6.77 (d, J=15.6 Hz, 1H) 5.18 (s, 2H); HPLC (water/ACN+ 0.1% TFA gradient) 95.9% at 220 nm; LCMS [M+H]$^+$=452.3, [M+Na]$^+$473.2.

(2E)-3-(3-Benzyloxy-3"-methyl-1,1':4',1"-terphenyl-2'-yl)prop-2-enamide

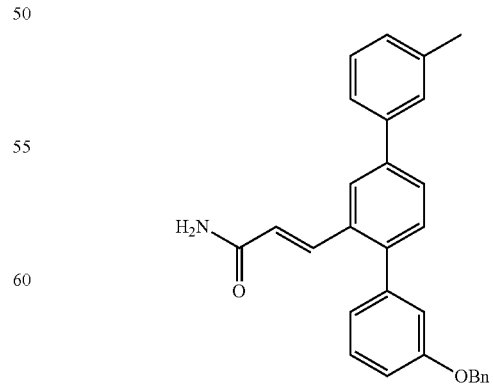

White solid foam (272 mg, 62%). $^1$H NMR (400 MHz, DMSO-$d_6$) d 7.94 (d, J=1.6 Hz, 1H) 7.73 (dd, J=8.2, 1.6 Hz, 1H) 7.58 (s, 1H) 7.54 (d, J=7.8 Hz, 1H) 7.45-7.51 (m, 4H) 7.37-7.44 (m, 5H) 7.33 (m, J=7.0 Hz, 1H) 7.23 (d, J=7.4 Hz, 1H) 7.13 (br. s, 1H) 7.09 (dd, J=8.4, 2.2 Hz, 1H) 6.99 (s, 1H) 6.92 (d, J=7.4 Hz, 1H) 6.75 (d, J=15.7 Hz, 1H) 5.16 (s, 2H) 2.41 (s, 3H); HPLC (water/ACN+0.1% TFA gradient) 97.7% at 220 nm; LCMS [M+H]$^+$=420.3, [M+Na]$^+$=442.3. Ca 4 wt % ethyl acetate and minor impurities by $^1$H NMR analysis.

(2E)-3-(3-Benzyloxy-3"-hydroxy-1,1':4',1"-terphenyl-2'-yl)prop-2-enamide

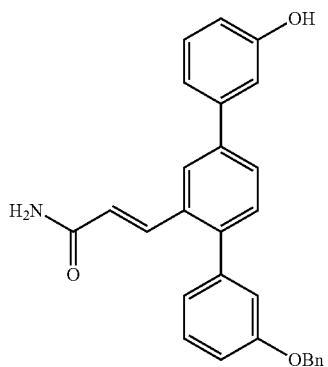 [SMILES: NC(=O)/C=C/c1cc(-c2cccc(O)c2)ccc1-c1cccc(OCc2ccccc2)c1]

Off-white solid foam (485 mg, 66%). $^1$H NMR (400 MHz, DMSO-d$_6$) d 9.58 (br. s, 1H) 7.91 (s, 1H) 7.69 (d, J=8.2 Hz, 1H) 7.46-7.54 (m, 4H) 7.39-7.46 (m, 4H) 7.26-7.39 (m, 2H) 7.06-7.22 (m, 4H) 6.91-7.04 (m, 2H) 6.84 (d, J=7.8 Hz, 1H) 6.76 (d, J=15.7 Hz, 1H) 5.17 (s, 2H); HPLC (water/ACN+0.1% TFA gradient) 89.3% at 220 nm; LCMS 444.2=[M+Na]$^+$. Ca 7 wt % ethyl acetate and 16 mol % of an unknown impurity by $^1$H NMR analysis.

(2E)-3-(3-Benzyloxy-3"-methoxy-1,1':4',1"-terphenyl-2'-yl)prop-2-enamide

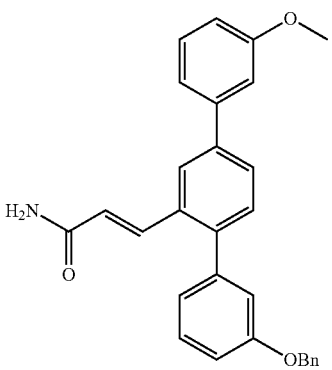 [SMILES: COc1cccc(-c2ccc(-c3cccc(OCc4ccccc4)c3)c(/C=C/C(N)=O)c2)c1]

The crude title compound (456 mg, 68%) contained (2E)-3-[3'-(benzyloxy)biphenyl-2-yl]prop-2-enamide and triphenylphosphine oxide. Purified further by flash chromatography (silica, 20-100% ethyl acetate/dichloromethane gradient) to give the crude title compound (361 mg) containing (2E)-3-[3'-(benzyloxy)biphenyl-2-yl]prop-2-enamide. Purified further by preparative HPLC (C$_{18}$, 30-90% acetonitrile in water (+0.1% TFA)) to give the title compound as a colourless glassy solid (218 mg, 32%). $^1$H NMR (400 MHz, DMSO-d$_6$) d 7.94 (s, 1H) 7.74 (dd, J=7.8, 1.2 Hz, 1H) 7.44-7.54 (m, 4H) 7.37-7.44 (m, 5H) 7.29-7.37 (m, 2H) 7.27 (s, 1H) 7.12 (br. s, 1H) 7.09 (dd, J=8.4, 1.8 Hz, 1H) 6.95-7.03 (m, 2H) 6.92 (d, J=7.4 Hz, 1H) 6.75 (d, J=15.7 Hz, 1H) 5.16 (s, 2H) 3.85 (s, 3H); HPLC (water/ACN+0.1% TFA gradient) 98.4% at 220 nm; LCMS [M+H]$^+$=436.3, [M+Na]$^+$=458.3.

Example 5: Synthesis of P3, P46, P47, P48, P49 and P50

Figure 6:
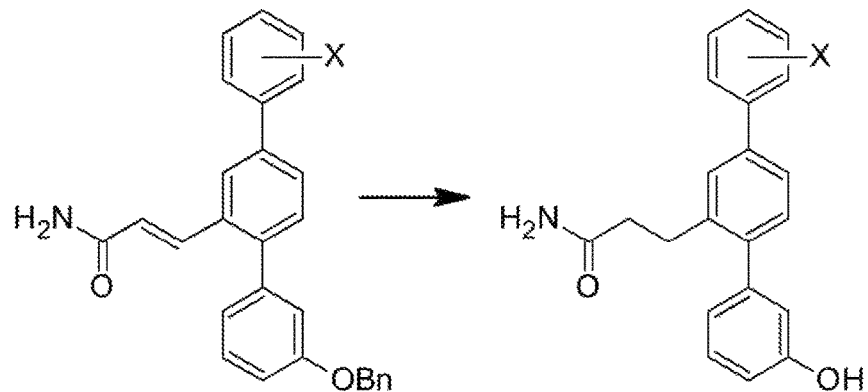
FIG. 6: Synthesis scheme for P3, P46, P47, P48, P49 and P50.

The synthetic route used to prepare P3, P46, P47, P48, P49 and P50 is shown in FIG. 6.

Palladium on activated carbon (10% wt/wt, 10 mg per 100 mg of benzyloxy-terphenyl derivative) was added to a solution of the benzyloxy-terphenyl derivative (1 equiv.) in ethyl acetate or methanol (5-15 mL) and triethylamine (100 µL per 1 mL of ethyl acetate or methanol) and placed under a balloon of hydrogen and heated to reflux until the reaction was complete by TLC, HPLC and/or LCMS. The work-up and purification procedures differed for each compound and are described below.

The following compounds were produced by this method.

3'-(3-Amino-3-oxopropyl)-3"-hydroxy-1,1':4',1"-terphenyl-3-carboxylic Acid (P47)

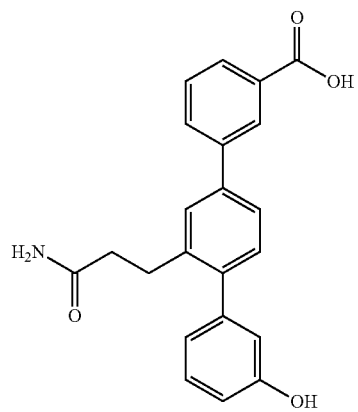 [SMILES: NC(=O)CCc1cc(-c2cccc(C(=O)O)c2)ccc1-c1cccc(O)c1]

The reaction mixture was cooled, diluted with hydrochloric acid (2 M, 10 mL), and ethyl acetate (20 mL) and filtered through celite, washing the celite pad with ethyl acetate (2×20 mL). Hydrochloric acid (2 M, 20 mL) was added to the filtrates, and the organic layer collected. The aqueous layer was extracted with ethyl acetate (2×30 mL). The combined organic extracts were concentrated to give the title compound in crude form. This material was washed with methanol:dichloromethane (1:3, 3×0.5 mL) and dried under vacuum to give the title compound as an off-white powder after drying under vacuum at 40° C. (41 mg, 47%). $^1$H NMR (400 MHz, DMSO-d$_6$) δ 9.52 (s, 1H) 8.22 (s, 1H) 7.95 (d, J=7.8 Hz, 2H) 7.65 (br. s, 1H) 7.62 (t, J=7.8 Hz, 1H) 7.56 (dd, J=7.8, 1.2 Hz, 1H) 7.19-7.29 (m, 3H) 6.77 (t, J=8.6 Hz, 2H) 6.72 (br. s, 2H) 2.84 (t, J=8.0 Hz, 2H) 2.31 (t, J=8.6 Hz, 2H); HPLC (water/ACN+0.1% TFA gradient) 97.4% at 220 nm; LCMS [M+H]$^+$=362.2 [M+Na]$^+$=384.2.

3-(4"-Fluoro-3-hydroxy-1,1':4',1"-terphenyl-2'-yl)propanamide (P3)

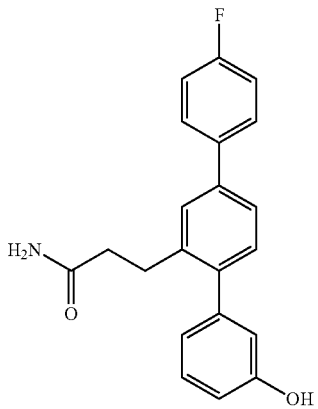 [SMILES: NC(=O)CCc1cc(-c2ccc(F)cc2)ccc1-c1cccc(O)c1]

The reaction mixture was cooled to room temperature and the ensuing mixture diluted with hydrochloric acid (2M, 15 mL) and ethyl acetate (15 mL) and filtered through celite, washing the celite pad with ethyl acetate (2×20 mL). Additional hydrochloric acid (2 M, 20 mL) was added to the filtrates, and the organic layer collected. The aqueous layer was extracted with ethyl acetate (2×20 mL). The combined organic extracts were concentrated, and the residue crystalised by the addition of dichloromethane (2 mL). The mixture was concentrated to give crude title compound (75 mg) as an off-white powder which was washed with ethanol (3×0.5 mL) and dried under vacuum to give the title compound as an off-white powder (30 mg, 37%) after drying under vacuum. $^1$H NMR (400 MHz, DMSO-$d_6$) δ 9.51 (s, 1H) 7.73 (dd, J=8.4, 5.7 Hz, 2H) 7.58 (s, 1H) 7.50 (dd, J=8.2, 1.6 Hz, 1H) 7.31 (t, J=8.8 Hz, 2H) 7.15-7.27 (m, 3H) 6.65-6.83 (m, 4H) 2.82 (t, J=7.8 Hz, 2H) 2.30 (t, J=8.0 Hz, 2H); HPLC (water/ACN+0.1% TFA gradient) 97.6% at 220 nm; LCMS [M+H]$^+$=336.2, [M+Na]$^+$=358.1.

3-(4"-Amino-3-hydroxy-1,1':4',1"-terphenyl-2'-yl)propanamide (P49)

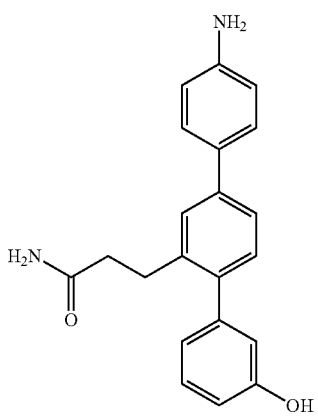 [SMILES: NC(=O)CCc1cc(-c2ccc(N)cc2)ccc1-c1cccc(O)c1]

The reaction mixture was cooled to room temperature and the ensuing mixture was diluted with ammonium chloride (sat., 30 mL) and ethyl acetate (30 mL) and filtered through celite, washing the celite pad with ethyl acetate (2×20 mL). The organic layer of the filtrate was separated and the aqueous layer extracted with ethyl acetate (2×30 mL). The combined organic extracts were dried over magnesium sulfate and concentrated, to give an off-white powder (67 mg). The crude product was purified by flash chromatography (silica, 30-100% ethyl acetate/hexanes gradient) to give the title compound as a white powder after drying under vacuum (41 mg, 37%). $^1$H NMR (400 MHz, DMSO-$d_6$) δ 9.48 (s, 1H) 7.47 (s, 1H) 7.38 (d, J=8.6 Hz, 3H) 7.18-7.27 (m, 2H) 7.12 (d, J=7.8 Hz, 1H) 6.68-6.79 (m, 4H) 6.65 (d, J=8.2 Hz, 2H) 5.22 (s, 2H) 2.79 (t, J=7.8 Hz, 2H) 2.28 (t, J=7.8 Hz, 2H); HPLC (water/ACN+0.1% TFA gradient) 100.0% at 220 nm; LCMS [M+H]$^+$=333.2, [M+Na]$^+$=355.2.

3-(3-Hydroxy-3"-methyl-1,1':4',1"-terphenyl-2'-yl)propanamide (P46)

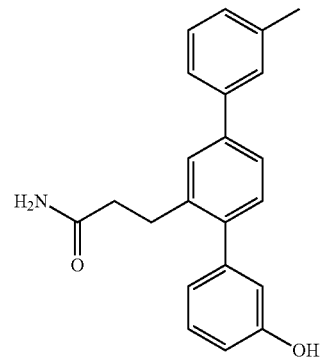 [SMILES: Cc1cccc(-c2ccc(-c3cccc(O)c3)c(CCC(N)=O)c2)c1]

The reaction mixture was cooled, acidified with hydrochloric acid-diethyl ether (to pH 4-6), silica added and the mixture concentrated. Purification by flash chromatography (silica, 10-100% ethyl acetate/hexanes gradient), gave the desired compound. This material was ground to a fine powder and dried under vacuum for 2 days to give the title compound as a white solid foam (109 mg, 55%).

$^1$H NMR (400 MHz, DMSO-$d_6$) δ 9.51 (s, 1H) 7.59 (s, 1H) 7.43-7.55 (m, 3H) 7.36 (t, J=7.6 Hz, 1H) 7.14-7.29 (m, 4H) 6.64-6.84 (m, 4H) 2.83 (t, J=7.8 Hz, 2H) 2.39 (s, 3H) 2.30 (t, J=7.8 Hz, 2H); HPLC (water/ACN+0.1% TFA gradient) 98.9% at 220 nm; LCMS [M+H]$^+$=332.3 [M+H]$^+$, [M+Na]$^+$=354.2

3-(3,3"-Dihydroxy-1,1':4',1"-terphenyl-2'-yl)propanamide (P48)

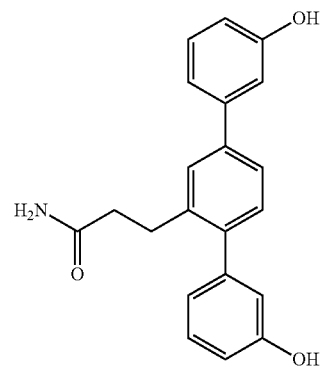 [SMILES: NC(=O)CCc1cc(-c2cccc(O)c2)ccc1-c1cccc(O)c1]

The reaction mixture was diluted with hydrochloric acid (2 M, 5 mL) and ethyl acetate (30 mL) and filtered through celite, washing the celite pad with ethyl acetate (2×20 mL). The filtrate was diluted with hydrochloric acid (2 M, 20 mL) and the organic layer was separated and the aqueous layer extracted with ethyl acetate (2×30 mL). The combined organic extracts were dried over magnesium sulfate, concentrated, and purified by preparative HPLC (C18, 20-70% acetonitrile in water (+0.1% TFA)) to give the title compound as a white powder (24 mg, 15%) after drying under vacuum. $^1$H NMR (400 MHz, DMSO-$d_6$) δ 9.52 (br. s, 2H) 7.53 (s, 1H) 7.44 (d, J=7.8 Hz, 1H) 7.14-7.30 (m, 4H) 7.09 (d, J=7.8 Hz, 1H) 7.05 (s, 1H) 8.65-6.81 (m, 5H) 2.81 (t, J=7.8 Hz, 2H) 2.29 (t, J=7.8 Hz, 2H); HPLC (water/ACN+ 0.1% TFA gradient) 96.8% at 220 nm; LCMS [M+H]$^+$=334.2, [M+Na]$^+$=356.1.

3-(3-Hydroxy-3''-methoxy-1,1':4',1''-terphenyl-2'-yl) propanamide (P50)

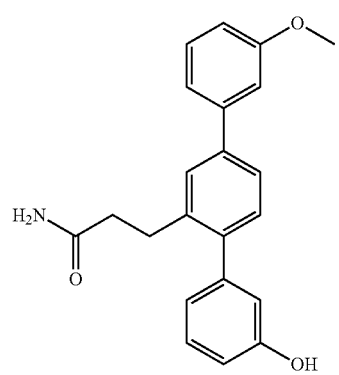 [SMILES: COc1cccc(-c2ccc(-c3cccc(O)c3)c(CCC(N)=O)c2)c1]

The reaction mixture was cooled to room temperature and diluted with hydrochloric acid (2 M, 10 mL) and ethyl acetate (20 mL) and filtered through celite, washing the celite pad with ethyl acetate (2×30 mL). The filtrate was diluted with hydrochloric acid (2 M, 25 mL) and the organic layer was separated and the aqueous layer extracted with ethyl acetate (2×30 mL). The combined organic extracts were dried over magnesium sulfate, concentrated, to give a white powder which was further crushed and dried under vacuum to give the title compound as a white powder (90 mg, 54%). $^1$H NMR (400 MHz, DMSO-$d_6$) δ 9.51 (br. s, 1H) 7.60 (s, 1H) 7.52 (dd, J=7.8, 1.2 Hz, 1H) 7.39 (t, J=7.8 Hz, 1H) 7.16-7.30 (m, 5H) 6.95 (dd, J=8.0, 1.8 Hz, 1H) 6.67-6.84 (m, 4H) 3.84 (s, 3H) 2.83 (t, J=7.8 Hz, 2H) 2.31 (t, J=8.0 Hz, 2H); HPLC (water/ACN+0.1% TFA gradient) 98.4% at 220 nm; LCMS [M+H]$^+$=348.2, [M+Na]$^+$=370.2.

Example 6: Synthesis of P1, P6 and P33

The synthetic route used to prepare P1, P6 and P33 is described below.

Coupling Procedure A

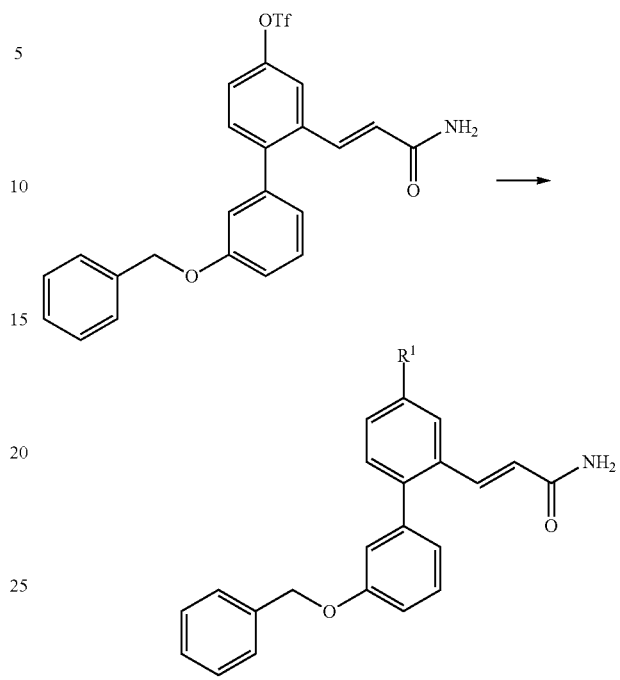

A 20 mL microwave vial was charged with a mixture of 2-[(1E)-3-amino-3-oxoprop-1-en-1-yl]-3'-benzyloxybiphenyl-4-yl trifluoromethanesulfonate (1.0 eq), boronic acid (1.3 eq) and potassium carbonate (3.0 eq) in a solution of water/ethanol/toluene (1:2:3 0.05M). Nitrogen was bubbled through the solution for 5 min, before tetrakis(triphenylphosphine)palladium(0) (10 mol %) was added and the reaction mixture was sealed and placed: in a microwave reactor for 3 h at 110° C. Upon consumption of the starting material as indicated by TLC and/or LCMS, the mixture was cooled, absorbed on silica gel and purified by flash chromatography (ethyl acetate/hexanes) to give the following compounds.

(2E)-3-(3''-Fluoro-3-benzyloxy-1,1':4'1''-terphenyl-2'-yl)prop-2-enamide

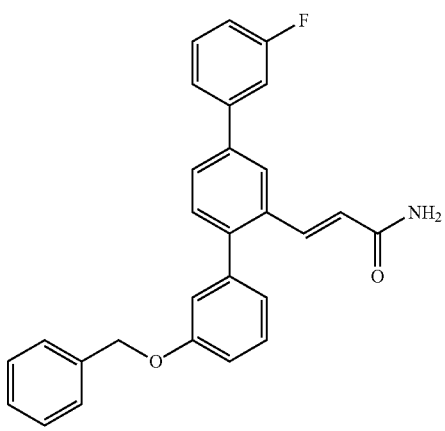 [SMILES: NC(=O)/C=C/c1cc(-c2cccc(F)c2)ccc1-c1cccc(OCc2ccccc2)c1]

(2E)-3-(3''-Fluoro-3-benzyloxy-1,1':4',1''-terphenyl-2'-yl) prop-2-enamide was obtained as an off-white solid (0.300 g, 68%). $^1$H NMR (400 MHz, CDCl$_3$) δ 7.83 (d, J=1.9 Hz, 1H), 7.70 (d, J=15.8 Hz, 1H), 7.62 (dd, 1.9, 8.0 Hz, 1H), 7.47-7.44 (m, 3H), 7.44-7.40 (m, 3H), 7.40-7.37 (m, 2H), 7.36-7.32 (m, 3H), 7.04-7.00 (m, 1H), 6.99-6.97 (m, 1H), 6.96-6.93 (m, 1H), 6.45 (d, 15.7 Hz, 1H), 5.42 (br. s, 2H), 5.10 (s, 2H); LCMS[M+H]⁺=424.2, [M+Na]⁺=446.1. Minor impurities detected by ¹H NMR.

(2E)-3-[3'-Benzyloxy-4-(pyridin-4-yl)biphenyl-2-yl]prop-2-enamide

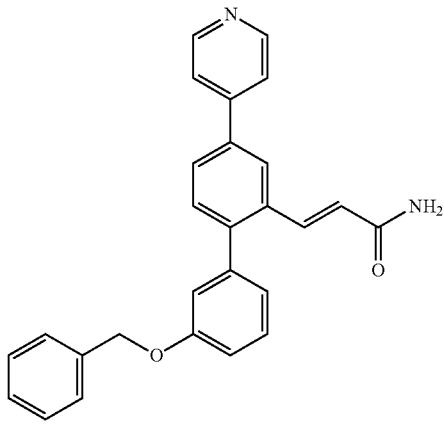 [SMILES: NC(=O)/C=C/c1cc(-c2ccncc2)ccc1-c1cccc(OCc2ccccc2)c1]

(2E)-3-[3'-Benzyloxy-4-(pyridin-4-yl)biphenyl-2-yl]prop-2-enamide was obtained as an off-white solid (0.150 g, 70%). ¹H NMR (400 MHz, CDCl₃) δ 8.90 (d, 1.8 Hz, 1H), 8.64 (dd, J=1.5, 4.8 Hz, 1H), 7.95-7.91 (m, 1H), 7.83 (d, J=1.8 Hz, 1H), 7.70 (d, J=15.8 Hz, 1H), 7.63 (dd, J=1.9, 8.0 Hz, 1H), 7.50-7.43 (m, 3H), 7.43-7.30 (m, 5H), 7.04-7.00 (m, 1H), 6.99-6.96 (m, 1H), 6.96-6.92 (m, 1H), 6.45 (d, J=15.7 Hz, 1H), 5.50 (br. s, 2H), 5.10 (s, 2H); LCMS[M+H]⁺=407.15, [M+Na]⁺=429.2. Minor impurities detected by ¹H NMR.

(2E)-3-(3",5"-Difluoro-3-benzyloxy-1,1':4',1"-terphenyl-2'-yl)prop-2-enamide

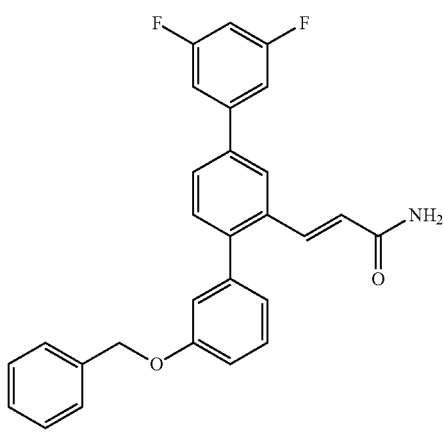 [SMILES: NC(=O)/C=C/c1cc(-c2cc(F)cc(F)c2)ccc1-c1cccc(OCc2ccccc2)c1]

(2E)-3-(3",5"-Difluoro-3-benzyloxy-1,1':4',1"-terphenyl-2'-yl)prop-2-enamide was obtained as an off-white solid (0.090, 39%), ¹H NMR (400 MHz, CDCl₃) δ 7.80 (d, J=1.9 Hz, 1H), 7.69 (d, J=15.8 Hz, 1H), 7.59 (dd, J=2.0, 8.0 Hz, 1H), 7.48-7.43 (m, 3H), 7.42-7.32 (m, 4H), 7.18-7.13 (m, 2H), 7.02 (ddd, J=0.9, 2.6, 8.3 Hz, 1H), 6.98-6.95 (m, 1H), 6.95-6.90 (m, 1H), 6.83 (d, J=8.8 Hz, 1H), 6.45 (d, J=15.7 Hz, 1H), 5.45 (br. s, 2H), 5.10 (s, 2H); LCMS[M+H]⁺=442.1, [M+Na]⁺=464.2. Minor impurities detected by ¹H NMR.

Hydrogenation Procedure A

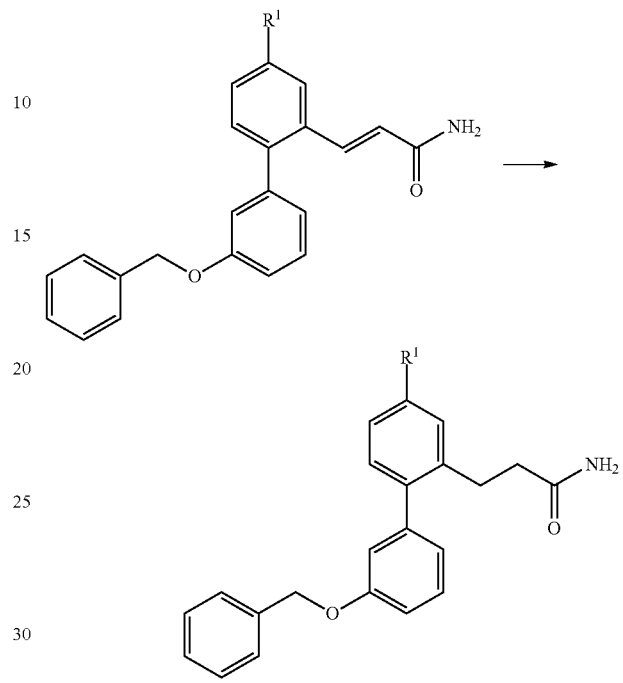

Palladium on activated carbon (10% wt/wt, 10 mg per 100 mg of (benzyloxy)-1,1':4',1"-terphenyl-2'-yl)prop-2-enamide derivative) was added to a solution of the (benzyloxy)-1,1':4',1"-terphenyl-2'-yl)prop-2-enamide derivative (1 equiv.) in ethyl acetate or methanol (5-15 mL) and triethylamine (100 µL per 1 mL of ethyl acetate or methanol), and placed under a balloon of hydrogen. The mixture was heated to reflux until the reaction was complete (24-48 h) as indicated by TLC, HPLC and/or LCMS. Upon consumption of the starting material, the reaction mixture was filtered through an HPLC nylon syringe filter, concentrated and purified by flash chromatography (methanol/dichloromethane) to give the following compounds.

3-(3"-Fluoro-3-hydroxy-1,1':4',1'-terphenyl-2'-yl)propanamide (P1)

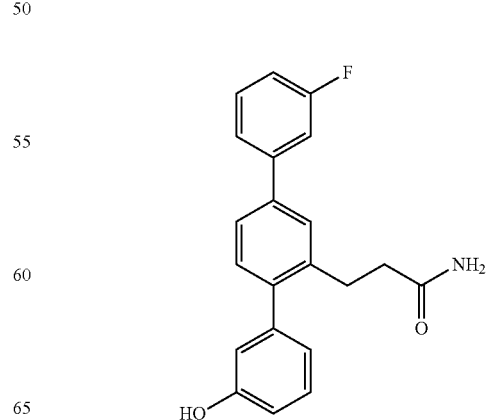

P1 was obtained as a white powder (0.105 g, 58%). ¹H NMR (400 MHz, CDCl₃) δ 9.51 (s, 1H), 7.64 (d, J=1.8 Hz, 1H), 7.58-7.50 (m, 4H), 7.27-7.17 (m, 4H), 6.80-6.70 (m, 4H), 2.86-2.79 (m, 2H), 2.33-2.29 (m, 2H); HPLC (water/ACN+0.1% TFA gradient) 98.28% at 220 nm; LCMS [M+H]⁺=336.1, [M+Na]⁺=358.1.

3-[3'-Hydroxy-4-(pyridin-4-yl)biphenyl-2-yl]propanamide (P6)

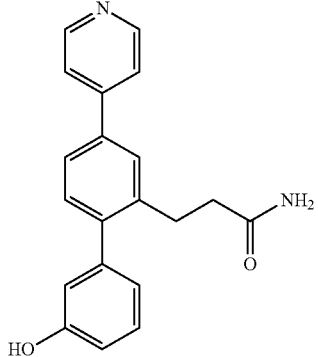 [SMILES: NC(=O)CCc1cc(-c2ccncc2)ccc1-c1cccc(O)c1]

P6 was obtained as a pale yellow powder (0.080 g, 64%). ¹H NMR (400 MHz, DMSO) δ 9.52 (s, 1H), 8.92 (d, J=1.8 Hz, 1H), 8.58 (dd, J=1.6, 4.8 Hz, 1H), 8.12-8.06 (m, 1H), 7.67 (d, J=1.9 Hz, 1H), 7.59 (dd, J=2.0, 7.9 Hz, 1H), 7.50 (ddd, J=0.8, 4.8, 7.9 Hz, 1H), 7.28-7.21 (m, 3H), 6.79 (ddd, J=1.0, 2.4, 8.1 Hz, 1H), 6.77-6.71 (m, 3H), 2.84 (dd, J=6.9, 8.9 Hz, 2H), 2.32 (dd, J=7.0, 8.9 Hz, 2H); HPLC (water/ACN+0.1% TFA gradient) >99% at 220 nm; LCMS [M+H]⁺=319.2.

3-(3",5"-Difluoro-3-hydroxy-1,1':4',1"-terphenyl-2'-yl)propanamide (P33)

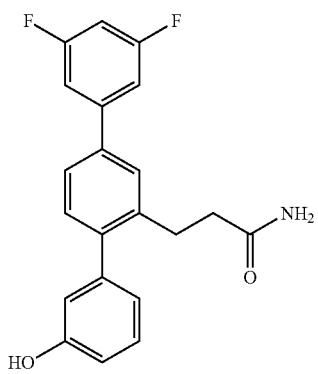 [SMILES: NC(=O)CCc1cc(-c2cc(F)cc(F)c2)ccc1-c1cccc(O)c1]

P33 was obtained as a white powder (0.090 g, 75%), ¹H NMR (400 MHz, DMSO) δ 9.52 (s, 1H), 7.89 (d, J=1.9 Hz, 1H), 7.60 (dd, J=2.0, 8.0 Hz, 1H), 7.51-7.44 (m, 2H), 7.27-7.19 (m, 4H), 6.79 (ddd, J=1.0, 2.4, 8.1 Hz, 1H), 6.77-6.72 (m, 2H), 6.72-6.69 (m, 1H), 2.82 (dd, J=7.0, 8.9 Hz, 2H), 2.33 (dd, J=7.1, 8.9 Hz, 2H); HPLC (water/ACN+ 0.1% TFA gradient) 98.83% at 220 nm; LCMS[M+H]⁺=354.1, [M+Na]⁺=376.1.

Example 7: Synthesis of P38, P42, P43, P44 and P45

The synthetic route used to prepare P38, P42, P43, P44 and P45 is described below.

2-(3-Amino-3-oxopropyl)-3'-hydroxybiphenyl-4-yl trifluoromethanesulfonate

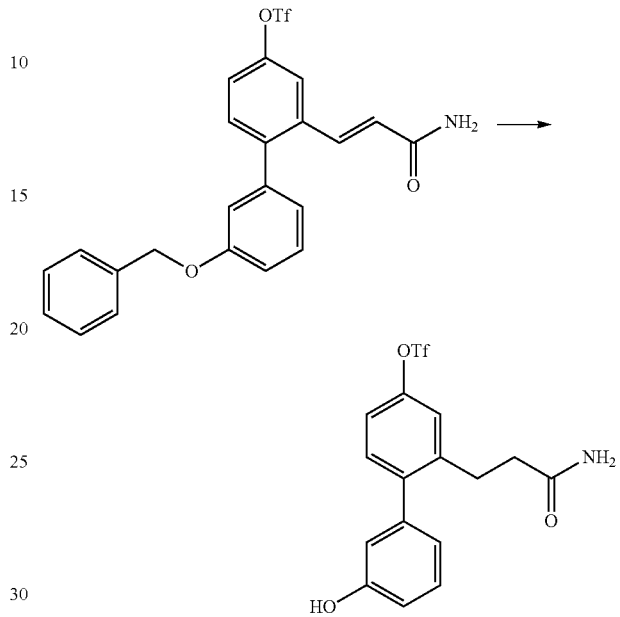

Platinum oxide (10 wt/wt %, 10 mg per 100 mg of substrate) was added to a solution of 2-[(1E)-3-amino-3-oxoprop-1-en-1-yl]-3'-benzyloxybiphenyl-4-yl trifluoromethanesulfonate (5.0 g, 10.4 mmol) in ethanol (250 mL), placed under a balloon of hydrogen and heated to reflux until the reaction was complete (24 h) as indicated by LCMS. On cooling, the reaction mixture was filtered through an HPLC nylon syringe filter, concentrated and the crude material purified by flash chromatography (ethyl acetate/hexanes) to give 2-(3-Amino-3-oxopropyl)-3'-hydroxybiphenyl-4-yl tri-floromethanesulfonate (2.6 g, 64%) as a pale pink powder. ¹H NMR (400 MHz, DMSO-d₆) δ 9.57 (s, 1H), 7.42 (d, J=2.5 Hz, 1H), 7.38-733 (m, 1H), 7.33-7.30 (m, 1H), 7.27-7.22 (m, 2H), 6.80 (ddd, J=0.8, 2.4, 8.1 Hz, 1H), 6.76 (br. s, 1H), 6.74-6.71 (m, 1H), 6.69-6.67 (m, 1H), 2.82-2.75 (m, 2H), 2.30-2.23 (m, 2H).

3-[3'-Hydroxy-4-(1-methyl-1H-pyrazol-5-yl)biphenyl-2-yl]propanamide (P38)

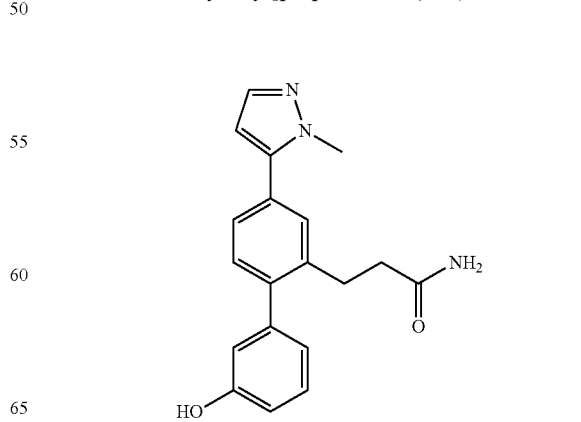

A 20 mL microwave vial was charged with 2-(3-amino-3-oxopropyl)-3'-hydroxybiphenyl-4-yl trifluoromethanesulfonate (0.35 g, 0.899 mmol), 1-methyl-1H-pyrazol-5-yl-5-boronic acid (0.17 g, 1.35 mmol) and potassium carbonate (0.37 g, 2.69 mmol) in a solution of toluene (8 mL), ethanol (5 mL) and water (1 mL). Nitrogen was bubbled through the mixture for 5 min, before tetrakis(triphenylphosphine)palladium(0) (10 mol %, 0.103 g, 0.089 mmol) was added, the reaction vial sealed and placed in a microwave reactor for 4 h at 120° C. On cooling, water (10 mL), 2M hydrochloric acid (10 mL) and ethyl acetate (10 mL) were added, the organic phase separated and the aqueous phase back extracted with ethyl acetate (2×10 mL). Combined organic phases were dried over anhydrous magnesium sulphate, filtered, concentrated and the crude material purified by flash chromatography (ethyl acetate/dichloromethane/methanol) to give P38 (0.045 g, 16%) as a white solid. $^1$H NMR (400 MHz, DMSO-$d_6$) δ 9.53 (s, 1H), 7.48 (d, J=2.0 Hz, 1H), 7.46 (d, J=1.6 Hz, 1H), 7.39 (dd, J=2.0, 7.8 Hz, 1H), 7.27-7.21 (m, 3H), 6.81-6.67 (m, 2H), 6.76-6.71 (m, 2H), 6.41 (d, J=1.8 Hz, 1H), 3.89 (s, 3H), 2.82 (t, J=7.8 Hz, 2H), 2.33-2.25 (m, 2H); HPLC (water/ACN+0.1% TFA gradient) 96.07% at 220 nm; LCMS [M+H]$^+$=322.20.

3-[4-(3,5-Dimethyl-1H-pyrazol-4-yl)-3'-hydroxybiphenyl-2-yl]propanamide (P42)

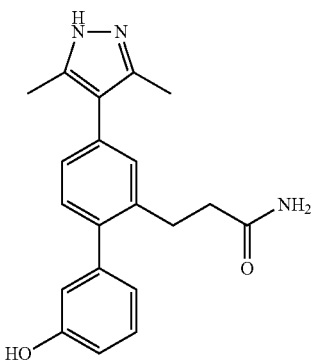 [SMILES: Cc1n[nH]c(C)c1-c1ccc(-c2cccc(O)c2)c(CCC(N)=O)c1]

A 20 ml microwave vial was charged with 2-(3-amino-3-oxopropyl)-3'-hydroxybiphenyl-4-yl trifluoromethanesulfonate (4-boronic acid pinacol ester)-3,5-dimethyl-1H-pyrazole-1-carboxylate (0.50 g, 1.54 mmol) and caesium carbonate (0.83 g, 2.56 mmol) in a solution of water (10 mL) and 1,4-dioxane (1 mL). Nitrogen was bubbled through the mixture for 5 min, before [1,1'-bis(diphenylphino)ferrocene]dichloropalladium(II), complex with dichloromethane(0) (10 mol %, 0.105 g, 0.128 mmol) was added, the reaction vial sealed and placed in a microwave reactor for 96 h at 80° C. On cooling, water (50 ml) was added, and the mixture washed with ethyl acetate (50 mL). The organic phase was separated and washed With 2M hydrochloric acid (20 ml). Aqueous phases were combined, further acidified to pH 1 and washed with ethyl acetate (3×50 ml). Combined organic phases were dried over anhydrous magnesium sulphate, filtered, concentrated and the crude residue purified by flash chromatography (methanol/dichloromethane) to give an off-white solid. This material was further purified by trituration from dichloromethane/chloroform to give P42 (0.030 g, 7%) as an off-white solid. $^1$H NMR (400 MHz, DMSO-$d_6$) δ 9.47 (s, 1H), 8.19 s, 1H), 7.25-7.19 (m, 3H), 7.15 (d, J=1.2 Hz, 2H), 6.78-6.73 (m, 2H), 6.73-6.70 (m, 2H), 2.78 (t, J=7.8 Hz, 2H), 2.30-2.25 (m, 2H), 2.23 (s, 6H); HPLC (water/ACN+0.1% TFA gradient) 96.21% at 220 nm; LCMS[M+H]$^+$=336.20.

3-[3'-Hydroxy-4-(3-methylthiophen-2-yl)biphenyl-2-yl]propanamide (P43)

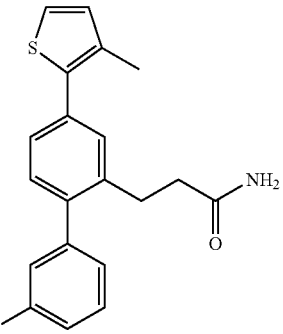

A 20 mL microwave vial was charged with 2-(3-amino-3-oxopropyl)-3'-hydroxybiphenyl-4-yl trifluoromethanesulfonate (0.50 g, 1.28 mmol), 4,4,5,5-tetramethyl-2-[3-(methyl)thiophen-2-yl]-1,3,2-dioxaborolane (0.35 g, 1.54 mmol) and caesium carbonate (1.25 g, 3.84 mmol) in a solution of water (1 mL) and 1,4-dioxane (10 mL). Nitrogen was bubbled through the mixture for 5 min, before [1,1'-bis(diphenylphosphino)ferrocene]dichloropalladium(II), complex with dichloromethane(0) (10 mol %, 0.105 g, 0.128 mmol) was added and the reaction vial sealed and placed in a microwave reactor for 9 h at 130° C. On cooling, the mixture was absorbed onto silica gel and purified by flash chromatography (ethyl acetate/dichlormethane/methanol) to give a yellow solid (0.260 mg) as an 85:15 mixture of desired product and starting material. This material (0.2 g) was dissolved in tetrahydrofuran (2 mL) and the solution cooled to 0° C. in an ice bath. Tetra-n-butylammonium fluoride (5.93 mL, 1M solution in THF, 5.93 mmol) was added, the reaction mixture allowed to come to room temperature and stirred for 60 h. Ethyl acetate (20 mL) was added, the organic phase was washed sequentially with 1M hydrochloric acid (10 mL), water (10 mL), dried over anhydrous magnesium sulphate, filtered, concentrated and the crude residue purified by flash chromatography (dichloromethane/ethyl acetate/methanol) to give a pale yellow solid. This material was further crystalised from dichloromethane/methanol to give P43 (0.055 g, 28%) as a pale yellow solid. $^1$H NMR (400 MHz, DMSO-$d_6$), δ 9.51 (s, 1H), 7.46 (d, J=5.1 Hz, 1H), 7.40 (d, J=1.8 Hz, 1H), 7.32 (dd, J=1.9, 7.9 Hz, 1H), 7.27-7.18 (m, 3H), 7.01 (d, J=5.1 Hz, 1H), 6.80-6.69 (m, 4H), 2.83-2.76 (m, 2H), 2.33 (s, 3H), 2.27 (dd, J=7.0, 8.8 Hz, 2H); HPLC (water/ACN+0.1% TFA gradient) 97.08% at 220 nm; LCMS [M+H]$^+$=338.2, [M+Na]$^+$=360.1.

3-[3'-Hydroxy-4-(4-methylthiophen-3-yl)biphenyl-2-yl]propanamide (P44)

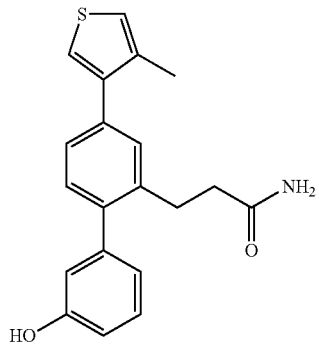 [SMILES: Cc1cscc1-c1ccc(-c2cccc(O)c2)c(CCC(N)=O)c1]

A 20 mL microwave vial was charged with 2-(3-amino-3-oxopropyl)-3'-hydroxybiphenyl-4-yl trifluoromethanesulfonate (0.50 g, 1.28 mmol), 4,4,5,5-tetramethyl-2-[4-(methyl)thiophen-3-yl][1,3,2]dioxaborolane (0.35 g, 1.54 mmol) and caesium carbonate (1.25 g, 3.84 mmol) in a solution of water (1 mL) and 1,4-dioxane (10 mL). Nitrogen was bubbled through the mixture for 5 min before [1,1'-bis(diphenylphosphino) ferrocene] dichloropalladium(II), complex with dichloromethane(0) (10 mol %, 0.105 g, 0.128 mmol) was added and the reaction vial was sealed and placed in a microwave reactor for 7.5 h at 130° C. On cooling, the mixture was absorbed onto silica gel and purified by flash chromatography (methanol/dichloromethane) to give a yellow solid. This material was further purified by trituration from dichloromethane to give P44 (0.110 g, 25%) as a white solid. $^1$H NMR (400 MHz, DMSO-$d_6$) δ 9.49 (s, 1H), 7.48 (d, J=3.1 Hz, 1H), 7.37 (d, J=1.8 Hz, 1H), 7.31-7.27 (m, 2H), 7.26-7.20 (m, 2H), 7.17 (d, J=7.8 Hz, 1H), 6.80-6.70 (m, 4H), 2.83-2.78 (m, 2H), 2.31-2.24 (m, 5H); HPLC (water/ACN+0.1% TFA gradient) 98.31% at 220 nm; LCMS [M+H]$^+$=338.15, [M+Na]+=360.10.

3-[3'-Hydroxy-4-(3-methyl-1H-pyrazol-4-yl)biphenyl-2-yl]propanamide (P45)

A 20 mL microwave vial was charged with 2-(3-amino-3-oxopropyl)-3'-hydroxybiphenyl-4-yl trifluoromethanesulfonate (0.25 g, 0.642 mmol), tert-butyl 3-methyl-4-(boronic acid pinacol ester)-1H-pyrazole-1-carboxylate (0.30 g, 0.96 mmol) and caesium carbonate (0.42 g, 1.28 mmol) in a solution of water (1 mL) and 1,4-dioxane (10 mL). Nitrogen was bubbled through the mixture for 5 min before [1,1-bis(diphenylphosphino)ferrocene] dichloropalladium(II), complex with dichloromethane(0) (10 mol %, 0.052 g, 0.064 mmol) was added and the reaction vial sealed and placed in a microwave reactor for 12 h at 80° C. On cooling, water (10 mL) was added and the mixture extracted with ethyl acetate (3×10 mL). The combined organic phases were dried over anhydrous magnesium sulphate, filtered and concentrated. The crude residue was taken up in ethyl acetate and washed with 2M hydrochloric add (20 mL). The aqueous acidic layer was set aside and a precipitate formed which, was isolated by filtration to give the title compound (0.080 g, 29%) as fine pale yellow crystals. $^1$H NMR (400 MHz, DMSO-$d_6$) δ 7.88 (s, 1H), 7.39 (d, J=1.7 Hz, 1H), 7.31 (dd, J=1.9, 7.9 Hz, 1H), 7.28-7.19 (m, 2H), 7.14 (d, J=7.9 Hz, 1H), 6.79-8.89 (m, 4H), 2.82-2.75 (m, 2H), 2.41 (s, 3H), 2.28 (dd, J=7.1, 8.9 Hz, 2H), NH and OH not seen; HPLC (water/ACN+0.1% TFA gradient) 97.39% at 220 nm; LCMS [M+H]$^+$=322.20.

Example 8: Synthesis of P4

The synthetic route used to prepare P4 is described below.

(2E)-3-[4-(4,4,5,5-Tetramethyl-1,3,2-dioxaborolan-1-yl)-3'-benzyloxybiphen-2-yl]prop-2-enamide

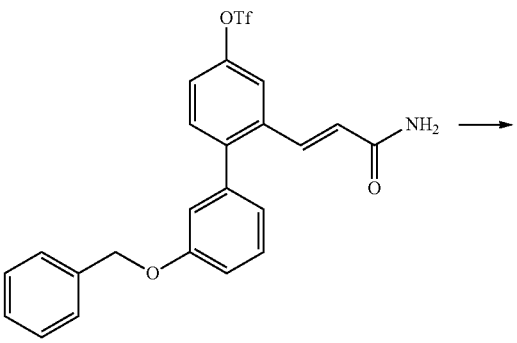

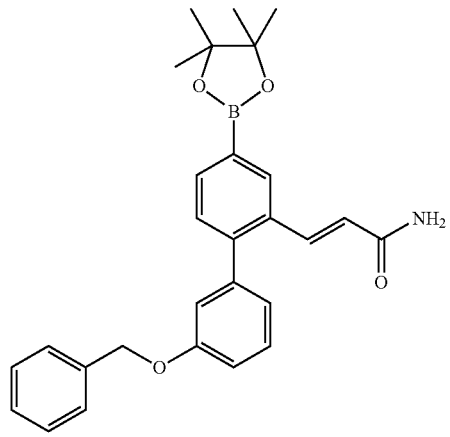

A 20 mL microwave vial was charged with 2-(3-amino-3-oxopropyl)-3'-benzyloxybiphenyl-4-yl trifluoromethanesulfonate (1.00 g, 2.10 mmol), bis(pinacolato) diboron (0.69 g, 2.73 mmol) and potassium acetate (0.62 g, 6.30 mmol) in 1,4-dioxane (15 mL). Nitrogen was bubbled through the mixture for 5 min, before [1,1-bis(diphenyl phosphino)ferrocene]dichloropalladium(II), complex with dichloromethane(0) (20 mol %, 0.343 g, 0.42 mmol) was added and the reaction vial sealed and placed in a microwave reactor for 5 h at 130° C. On cooling, the mixture was absorbed onto silica gel and purified by flash chromatography (ethyl acetate/dichloromethane) to give a yellow gum. This material was further purified by trituration from dichloromethane to give (2E)-3-[4-(4,4,5,5-Tetramethyl-1,3,2-dioxaborolan-1-yl)-3'-benzyloxybiphen-2-yl]prop-2-enamide (0.650 g, 68%) as a yellow solid. $^1$H NMR (400 MHz, CDCl$_3$) δ 8.13-8.08 (m, 1H), 7.84 (dd, J=1.2, 7.6 Hz, 1H), 7.88 (d, J=15.8 Hz, 1H), 7.46-7.44 (m, 1H), 7.44-7.42 (m, 1H), 7.40-7.30 (m, 5H), 6.99 (ddd, J=0.9, 2.6, 8.3 Hz, 1H), 6.94-6.92 (m, 1H), 6.92-6.88 (m, 1H), 6.48 (d, J=15.7 Hz, 1H), 5.61 (br, s, 2H), 5.08 (s, 2H), 1.37 (s, 12H); LCMS [M+H]$^+$=458.2, [M+Na]$^+$=478.2.

3-[4-(4,4,5,5-Tetramethyl-1,3,2-dioxaborolan-1-yl)-3'-hydroxybiphen-2-yl]propanamide 3-[3'-Hydroxy-4-(pyridin-2-yl)biphenyl-2-yl]propanamide (P4)

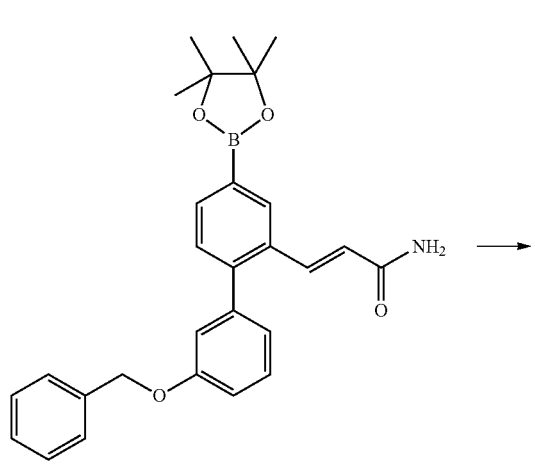

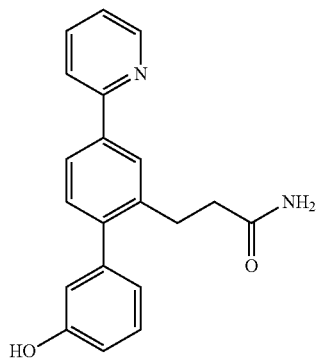 [SMILES: NC(=O)CCc1cc(-c2ccccn2)ccc1-c1cccc(O)c1]

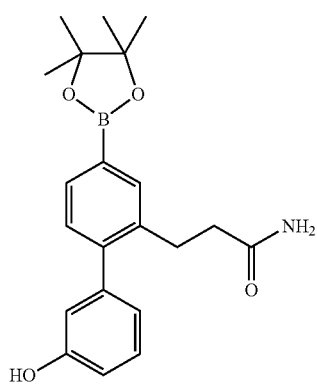

A 20 mL microwave vial was charged with crude 3-[4-(4,4,5,5-tetramethyl-1,3,2-dioxaborolan-1-yl)-3'-hydroxybiphen-2-yl]propanamide (0.15 g), 2-bromopyridine (0.14 g, 0.86 mmol) and potassium carbonate (0.11 g, 0.82 mmol) in a solution of wafer (0.5 mL) and dimethoxyethane (5.0 mL). Nitrogen was bubbled through the mixture for 5 min, before tetrakis(triphenylphosphine)palladium(0) (10 mol %, 0.047 g, 0.041 mmol) was added, the reaction vial sealed and placed in a microwave reactor for 4 h at 110° C. On cooling, the mixture was absorbed on silica gel and purified by flash chromatography (dichloromethane/ethyl acetate/methanol) to give (0.090 g) of a pale yellow solid. This material was crystalised from acetone to give P4 (0.07 g, 54%) as a fine off-white powder. $^1$H NMR (400 MHz, DMSO-$d_6$) δ 9.51 (s, 1H), 8.70-8.65 (m, 1H), 8.04 (d, J=1.8 Hz, 1H), 7.99-7.95 (m, 1H), 7.95-7.86 (m, 2H), 7.36 (ddd, J=1.1, 4.8, 7.4 Hz, 1H), 7.25 (td, J=3.9, 7.9 Hz, 3H), 6.81-6.70 (m, 4H), 2.88-2.81 (m, 2H), 2.34-2.27 (m, 2H); HPLC (water/ACN+0.1% TFA gradient) >99% at 220 nm; LCMS [M+H]$^+$ =319.15.

Example 9: Synthesis of P104

Figure 7:
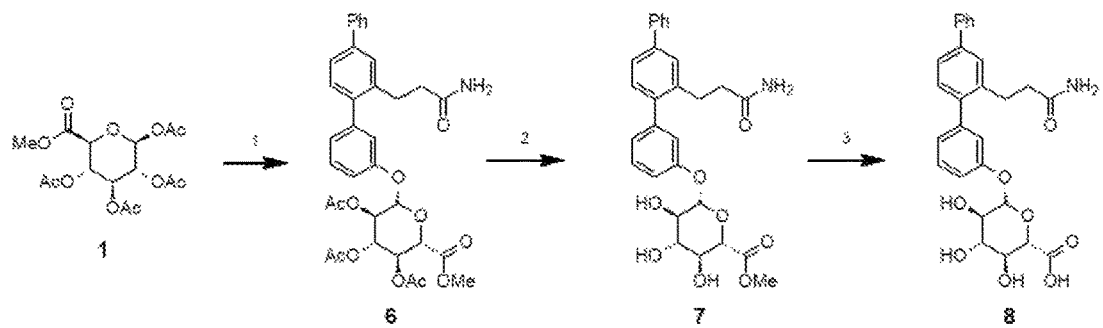
FIG. 7: Synthesis scheme for P104.

The synthetic route used to prepare P104 is shown in FIG. 7.

Step 1—a) pTSA, ZnCl$_2$ or SnCl$_4$ for X=OAc; b) TMSOTf or DEAD/PPh$_3$ for X=OH; or c) BF$_3$.OEt$_2$ for X=OC(NH)CCl$_3$.
Steps 2 and 3 LiOH(aq), EtOH.
Steps 1-3 are described in a) Atzrodt et al, ARKIVOC 2012 (iii) 257-278; b) Jacquinet, J-C, Carbohydrate Research, 199 (1990) 153-181; c) Stachulski and Jenkins, Natural Product Reports, 1998, p 173-186 and d) Engstrom et al, J. Org. Chem., 2006, 8378-8383.

Example 10: In Vitro Screening of Compounds

The xCELLigence SP system (Roche) was used to measure changes in cellular impedance (cell index) following the treatment of A10 embryonic vascular smooth muscle cells (ATCC, CRL-1476) with test compound. In this in vitro cell based experimental system a negative impedance profile correlates with blood pressure reduction in rats—a decrease in impedance is associated with vasodilatation and an increase in impedance is associated with vasoconstriction (Stallaert W, Dorn J F, van der Westhuizen E, Audet M & Bouvier M. Impedance responses reveal β-adrenergic sig- Platinum oxide (10 wt/wt %, 10 mg per 100 mg of substrate) was added to a solution of (2E)-3-[4-(4,4,5,5-tetramethyl-1,3,2-dioxaborolan-1-yl)-3'-benzyloxybiphen-2-yl]prop-2-enamide (0.30 g, 0.66 mmol) in ethanol (15 mL), the reaction mixture placed under a balloon of hydrogen and heated to reflux for 24 h. On cooling, the mixture was filtered through an HPLC nylon syringe filter, concentrated and the crude residue purified by flash chromatography (hexanes/ethyl acetate/methanol) to give (0.160 g) of a white powder as a 65:35 mixture by HPLC of 3-[4-(4,4,5,5-Tetramethyl-1,3,2-dioxaborolan-1-yl)-3'-hydroxybiphen-2-yl]propanamide and the corresponding boronic acid. LCMS [M+H]$^+$=368.2 (3-[4-(4,4,5,5-Tetramethyl-1,3,2-dioxaborolan-1-yl)-3'-hydroxybiphen-2-yl]propanamide) and [M+H]$^+$=286.1 (boronic acid). 3-[4-(4,4,5,5-Tetramethyl-1,3,2-dioxaborolan-1-yl)-3'-hydroxybiphen-2-yl]propanamide $^1$H NMR (400 MHz, MeOD) δ7.71 (s, 1H), 7.59 (dd, J=1.2, 7.6 Hz, 1H), 7.23 (t, J=7.8 Hz, 1H), 7.16 (d, J=7.6 Hz, 1H), 6.80-6.76 (m, 2H), 6.76-6.71 (m, 1H), 2.94-2.88 (m, 2H), 2.37-2.32 (m, 2H), 1.36 (s, 12H), NHH and OH not seen.

naling pluridensitometry and allow classification of ligands with distinct signalling profiles PLoS ONE 2012; 7(1): e29420, doi:10.1371/journal.pone.0029420).

Briefly, 50 µl of cell culture medium (DMEM low glucose supplemented with 10% fetal bovine serum at 37° C.) was added to each well of an E-Plate 96 (Roche), and the background impedance in each well was measured. 50 µl of A-10 cell suspension (10,000 cells/well) was then added to the appropriate wells of the E-Plate 96. Cell index was monitored for each well of the E-Plate 96 in RTCA SP Station within the cell culture incubator. After overnight incubation for 16-20 hours at 5% $CO_2$ and 95% humidity, 100 µl of test compound solution (test compounds were prepared in DMSO and diluted with cell culture medium to a final DMSO concentration of 0.25%) was added to the appropriate wells of the E-Plate 96 and cell index values were measured immediately following compound treatment every 20 seconds for 3 hours. Cell index value is baseline-corrected by subtracting the cell index of vehicle-treated cells and normalized by dividing by the cell index at the time point immediately before compound addition. Baseline normalized cell index as a function of time is plotted using Roche RTCA software.

Compounds may achieve reductions in blood pressure by interaction with vascular smooth muscle cells causing these cells to relax resulting in vasodilatation and a reduction in blood pressure. These are termed direct vasodilators. A negative impedance response for A10 vascular smooth muscle cells indicates that a test compound is a direct vasodilator.

The xCELLigence SP system was also used to measure changes in cellular impedance following the treatment of bovine aortic endothelial cells (European Collection of Cell Cultures) with test compound. The method employed is the same for the A10 embryonic vascular smooth muscle cells described above but with the cell culture medium supplemented with 15% fetal bovine serum instead of 10%.

Compounds may interact with vascular endothelial cells causing the release of substances such as nitric oxide and endothelium-derived hyperpolarising factor, which in turn act on the vascular smooth muscle cells causing vasodilatation and lowering blood pressure. Such compounds are termed indirect vasodilators. A negative impedance response for bovine aortic endothelial cells indicates that a test compound is an indirect vasodilator.

Figure 8:
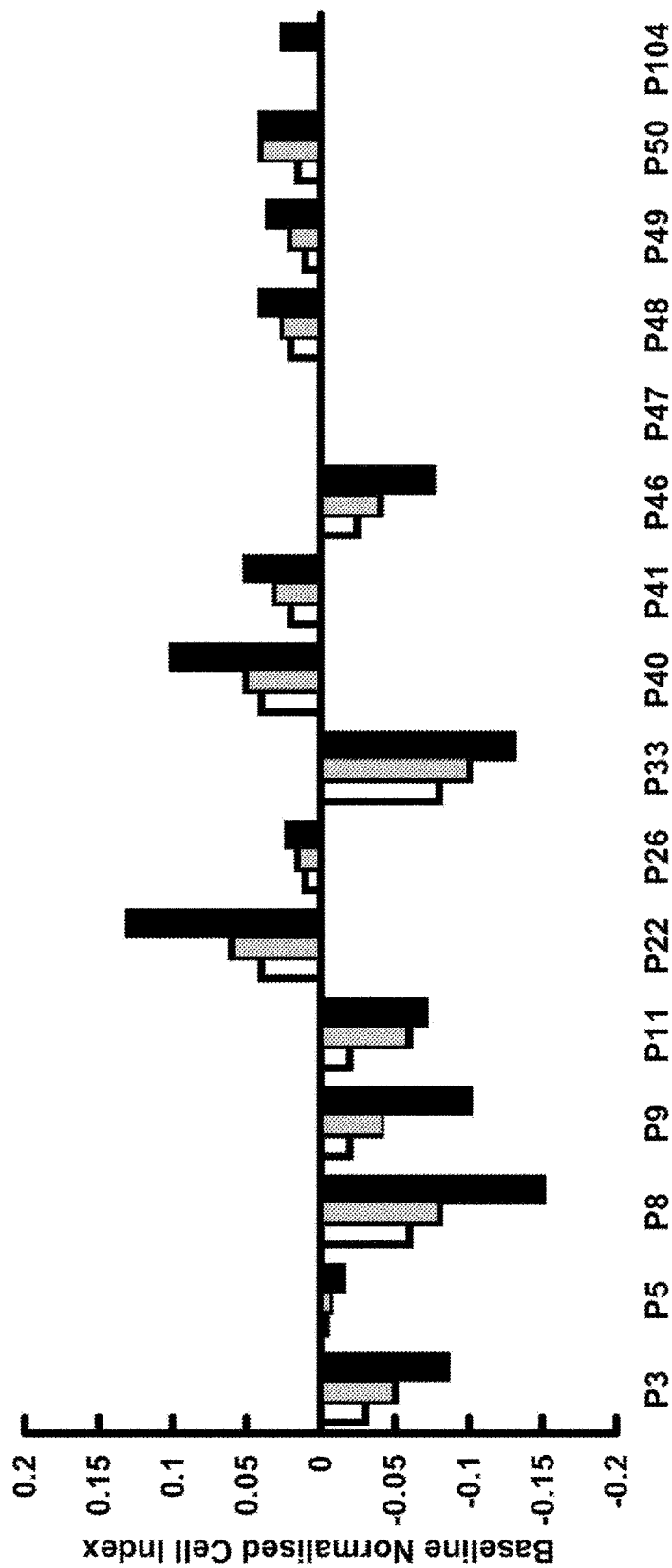
FIG. 8: Cell impedance in A10 vascular smooth muscle cells treated with test compounds at 62.5 µM (white bars), 125 µM (grey bars) or 250 µM (black bars).

Negative impedance responses for A10 vascular smooth muscle cells were observed for P3, P5, P8, P9, P11, P33 and P46 (FIG. 8), indicating that these compounds are direct vasodilators.

Figure 9:
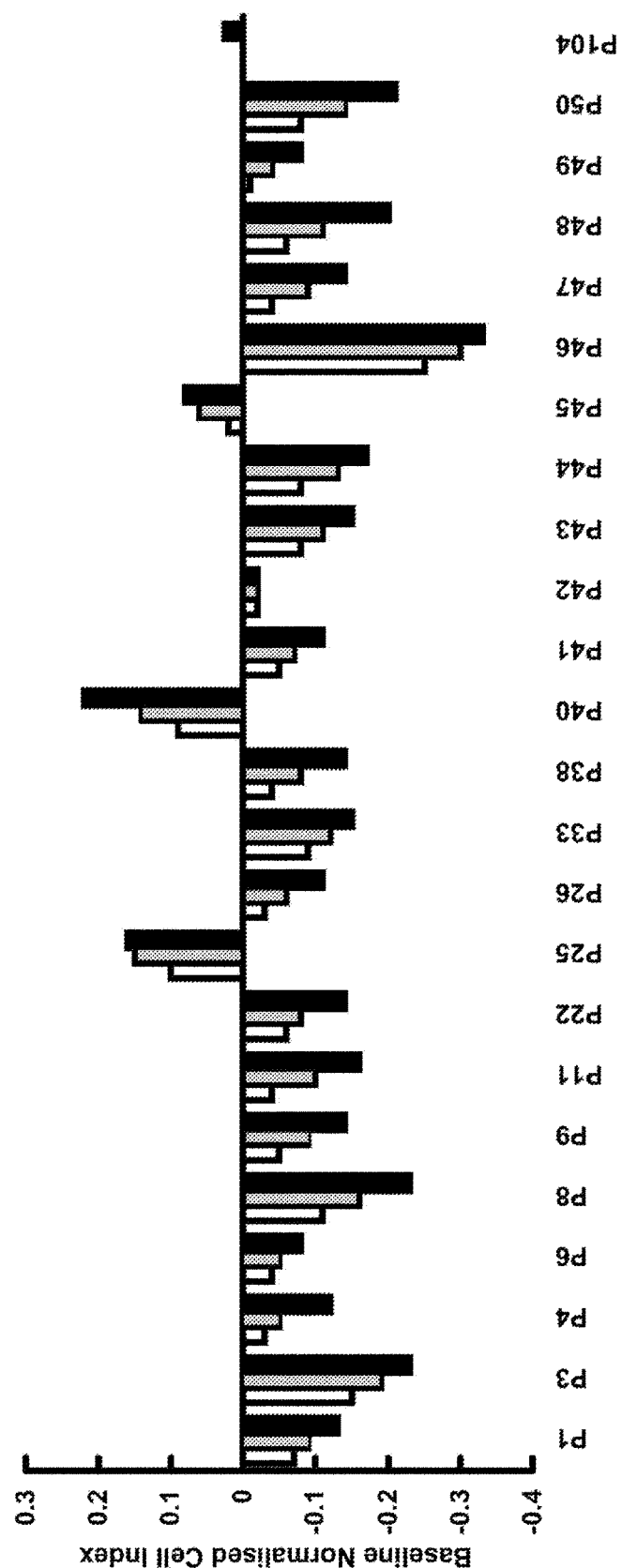
FIG. 9: Cell impedance in bovine aortic endothelial cells treated with test compounds at 62.5 µM (white bars), 125 µM (grey bars) or 250 µM (black bars).

Negative impedance responses for bovine aortic endothelial cells were observed for P1, P3, P4, P6, P8, P9, P11, P22, P26, P33, P38, P41, P42, P43, P44, P46, P47, P48, P49 and P50 (FIG. 9), indicating that these compounds are indirect vasodilators.

Rat (NRK-52E) renal proximal tubule cells grown in DMEM+10% FBS+1% NEAA+2 mM glutamine were placed in 96 well plates at 10,000 cells/well and incubated at 37° C. with 5% $CO_2$ overnight. Test compounds at a concentration of 30 µM were incubated with human or rat renal proximal tubule cells for 2 hours at 37° C. and 5% $CO_2$. Cis-diamminedichloroplatinum(III) (cisplatin) was then added at 5 µ/ml and each cell population was then incubated for 24 or 48 hours at 37° C. with 5% $CO_2$. Test compounds were maintained at their original concentrations. To assay the cytotoxic effects of cisplatin on the rat renal proximal tubule cells a highly water-soluble tetrazolium salt, WST-8, which is reduced by dehydrogenases in cells to produce formazan, a water-soluble, yellow-coloured indicator dye was used following the manufacturer's instructions (specifically the Cell Count Kit-8 (CCK-8) assay from Sigma). Plate absorbance of the WST-8 (CCK-8) reagent was then measured at 450 nm using a Thermo Scientific Multiskan EX plate reader.

Figure 10:
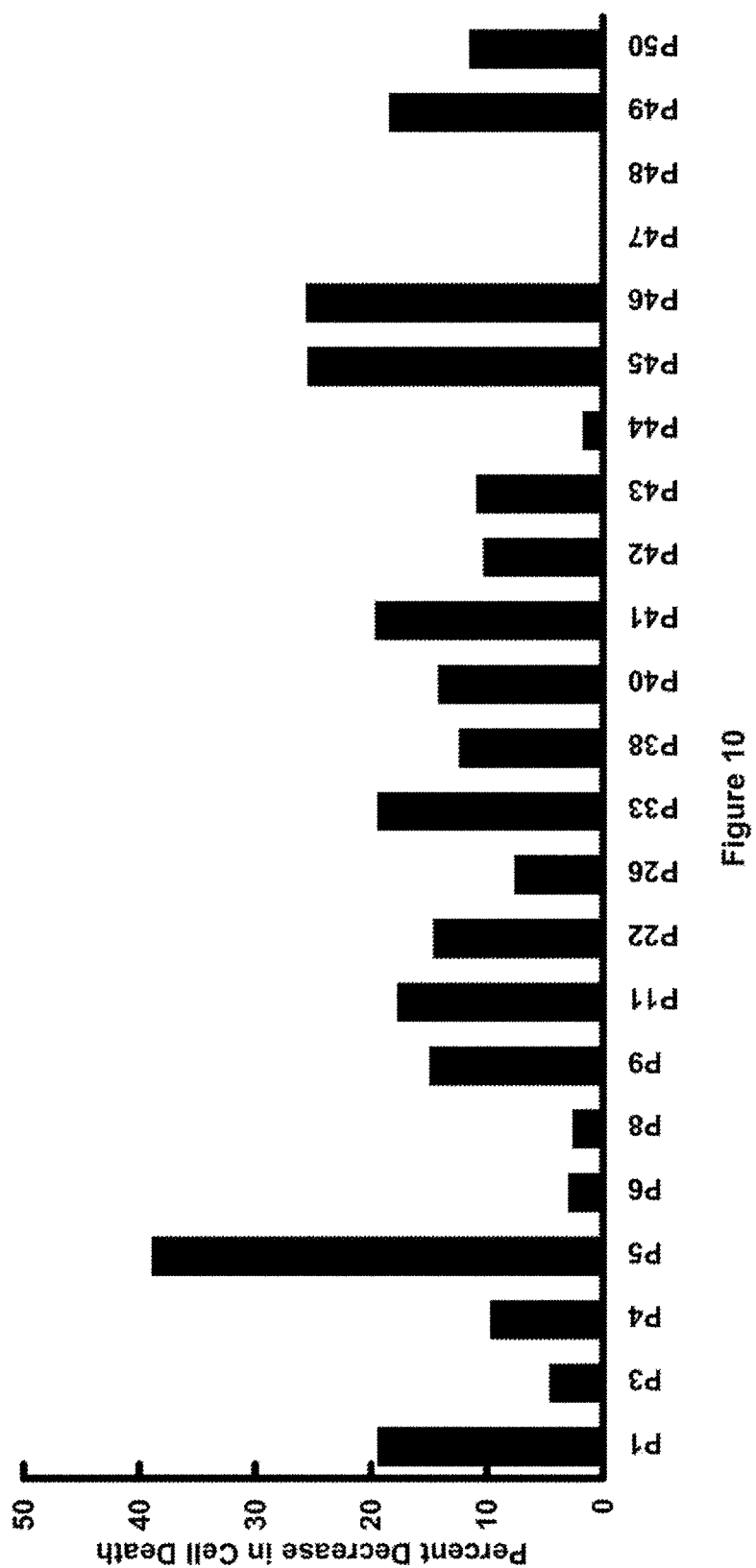
FIG. 10: Capacity of test compounds (30 µM) to rescue renal tubular cells from cytotoxicity as a consequence of treatment with cis-platin (5 µg/ml).

Cisplatin induced cell death decreased in cultures of renal proximal tubular cells treated with P1, P3, P4, P5, P6, P8, P9, P11, P22, P26, P33, P38, P40, P41, P42, P43, P44, P45, P46, P49 and P50 (FIG. 10), demonstrating that these compounds reduce renal proximal tubular cell death.

Example 11: In Vivo Screening of Compounds

Fourteen week old SHR (on a 2.2% salt diet; Glen Forrest Stockfeeders) were randomly assigned to zero time control (14 week old rats), test compound treatment drinking solution (500 pmol/kg/min in deionised distilled water) or control drinking solution (5% ethanol in deionised distilled water). The rats assigned to zero time control group (14 week old rats) were anaesthetised and had their kidneys and liver harvested while rats assigned to control and test compound treatment were weighed twice weekly and had their drinking solution intake monitored to allow adjustment of the test compound concentration in the drinking solution to maintain a constant dose over the 4-week study period. Blood pressure was measured twice weekly by tail cuff plethysmography (PowerLab, ADInstruments, Castle Hill, NSW, Australia). After 4 weeks rats were anaesthetised (18 week old rats), and their kidneys and liver harvested.

To quantitate tissue fibrosis and/or fat content, tissue slices ≤3 mm thick were fixed in 10% buffered formalin for 24 hours, processed and embedded in paraffin. Three micron transverse sections were stained using Masson's trichrome stain. A minimum of 20 random fields at magnification ×20 from transverse sections (5 at each of 2 levels) were digitized and the degree of fibrosis and fat content determined as a percent of field area of each digitized image using Image-Pro Plus V.7 (Media Cybernetics, Bethesda, Md., USA) then averaged to determine the level of fibrosis and/or fat content for each rat.

Figure 11:
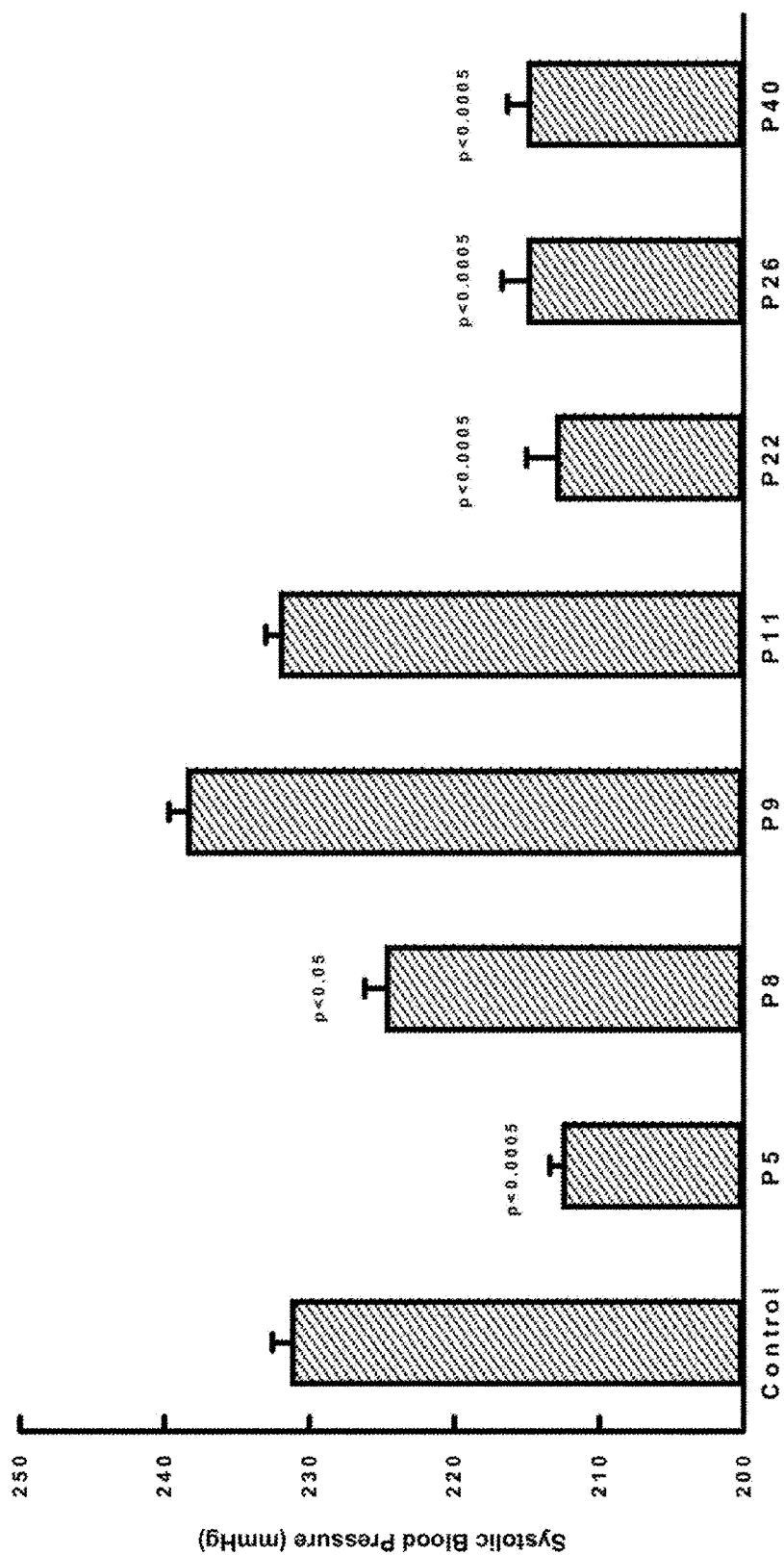
FIG. 11: Effect of test compounds on systolic blood pressure.

Blood pressure was reduced in rats treated with P5, P8, P22, P28 and P40 (FIG. 11).

Figure 12:
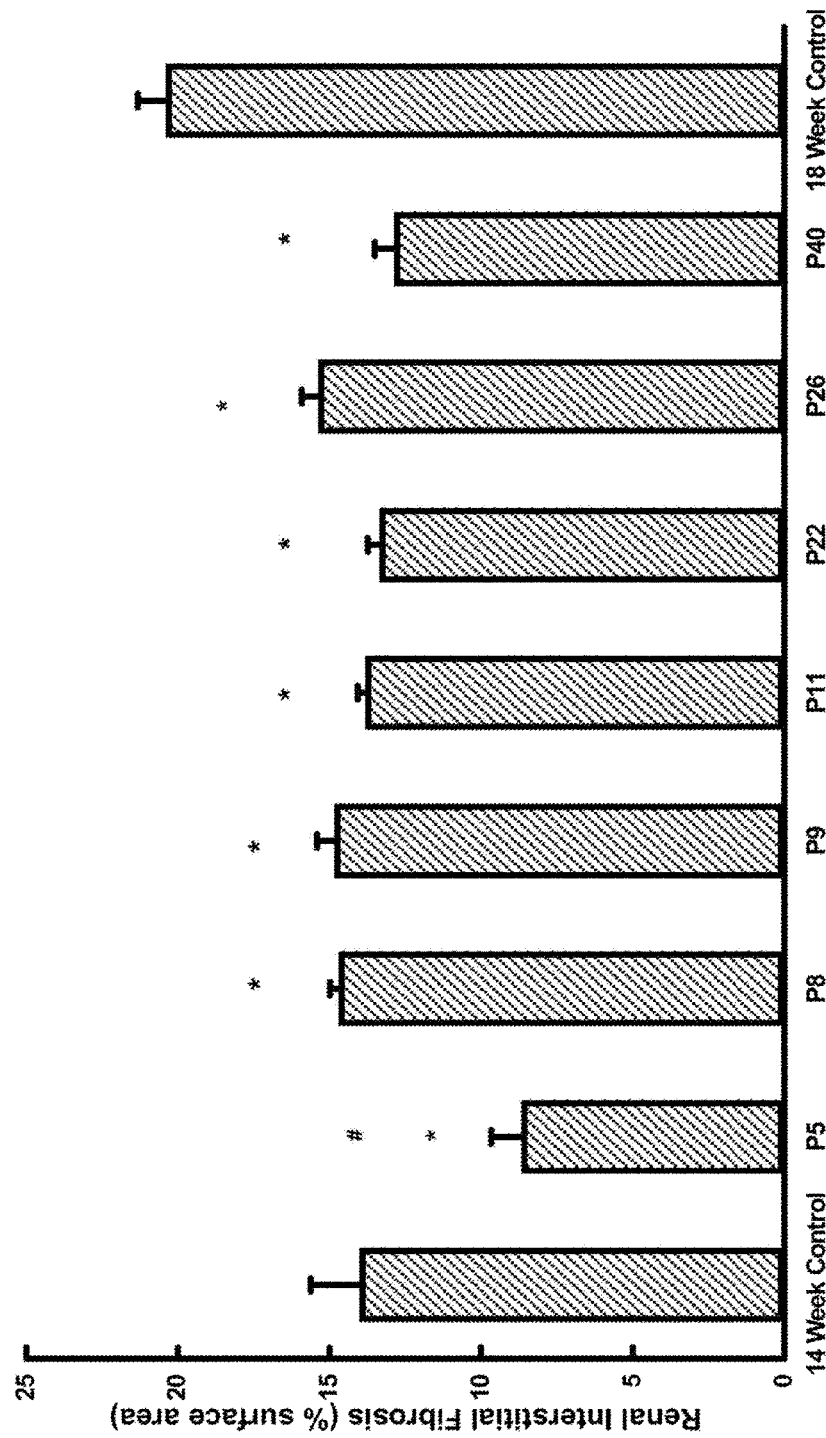
FIG. 12: Effect of test compounds on fibrosis in the kidney in SHR on 2.2% salt diet after 4 weeks treatment with test compound in 5% ethanol drinking solution or drinking solution alone.

Fibrosis in the kidney after 4 weeks treatment with 500 pmol/kg/min of P5, P8, P9, P11, P22, P26, P40 was decreased compared to 18 week controls (FIG. 12, *p<0.05), demonstrating that these compounds reduce the development of kidney fibrosis). Fibrosis in the kidney after 4 weeks treatment with 500 pmol/kg/min of P5 was also decreased compared to 14 week controls (FIG. 12, #p<0.05), demonstrating that this compound reverses established kidney fibrosis.

Figure 13:
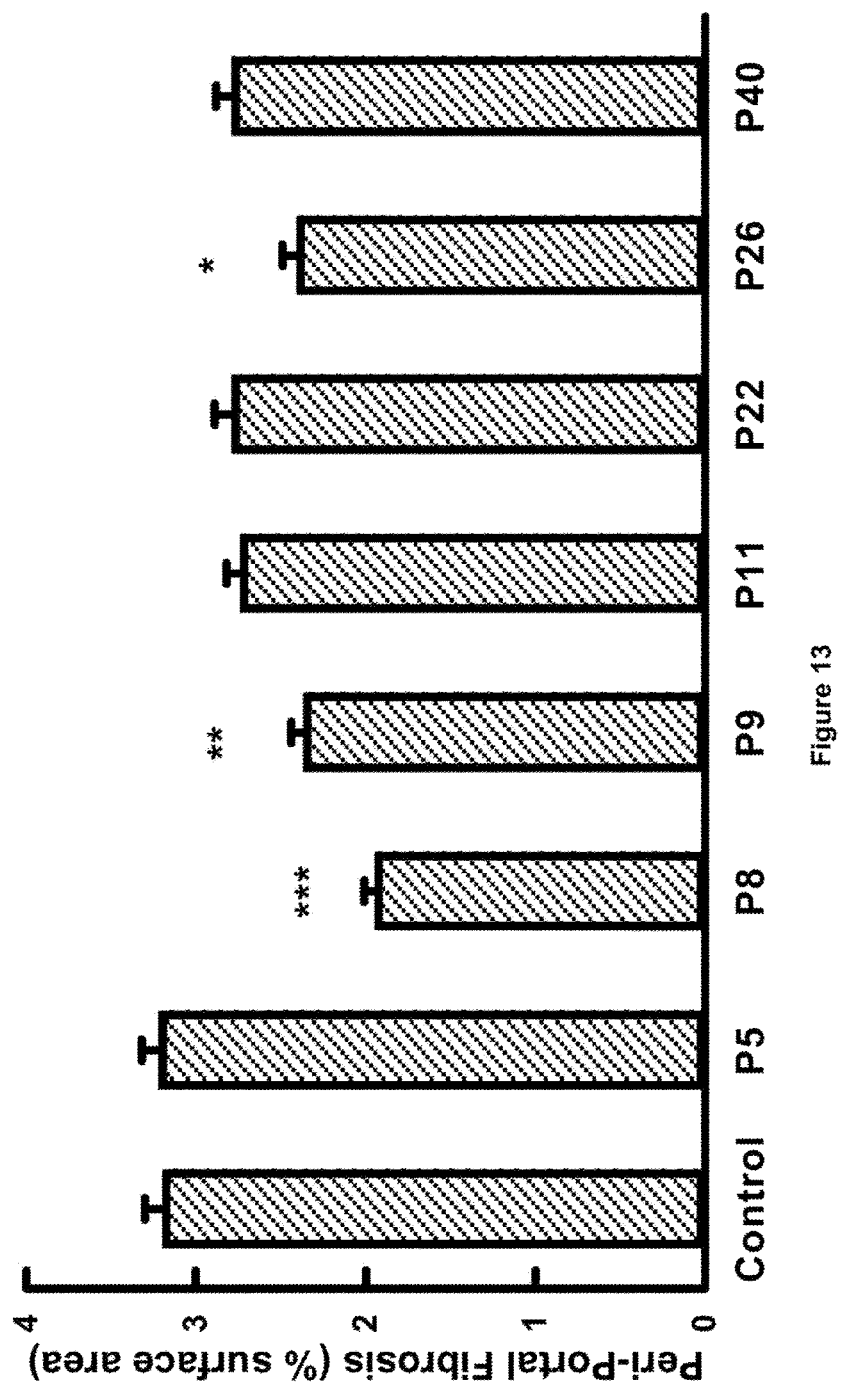
FIG. 13: Hepatic fibrosis in SHR at 18 weeks of age after 4 weeks treatment with test compounds (500 pmol/kg/min) in 5% ethanol drinking solution or drinking solution alone (18 week control).

Fibrosis in the liver after 4 weeks treatment with 500 pmol/kg/min of P8, P9, P11, P22, P26, P40 was decreased compared to 18 week controls (FIG. 13, *p<0.05, p<0.025 and *p<0.01), demonstrating that these compounds reduce the development of hepatic fibrosis.

Figure 14:
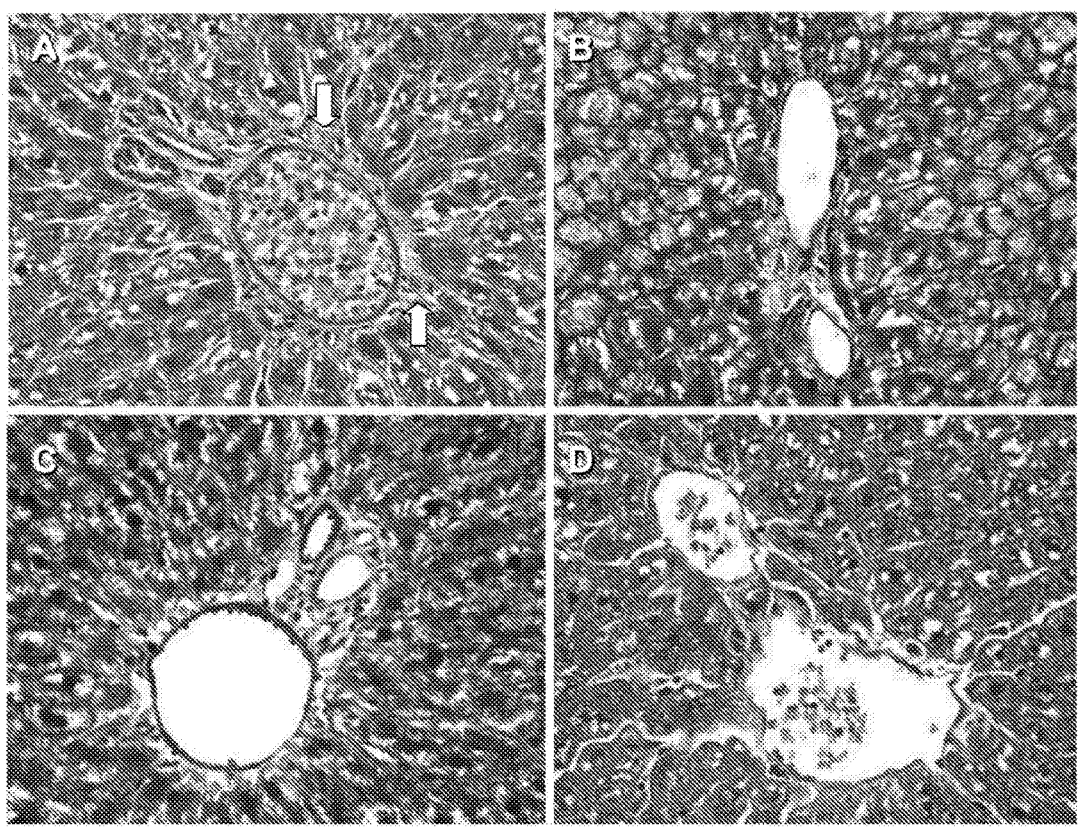
FIG. 14: Masson's tri-chrome stained tissue sections showing portal tracts from control rats (A), as well as rats treated with P8 (B), P9 (C) and P26 (D).

In Masson's tri-chrome stained sections showing portal tracts, fibrosis is clearly visible surrounding the portal tract and beginning to extend into the sinusoidal space (arrows) in the control (FIG. 14A). In sections from rats treated with P8 (FIG. 14B), P9 (FIG. 14C) and P26 (FIG. 14D), fibrous tissue is confined to the basement membrane in vessel walls and normal tissue architecture has been restored.

Figure 15:
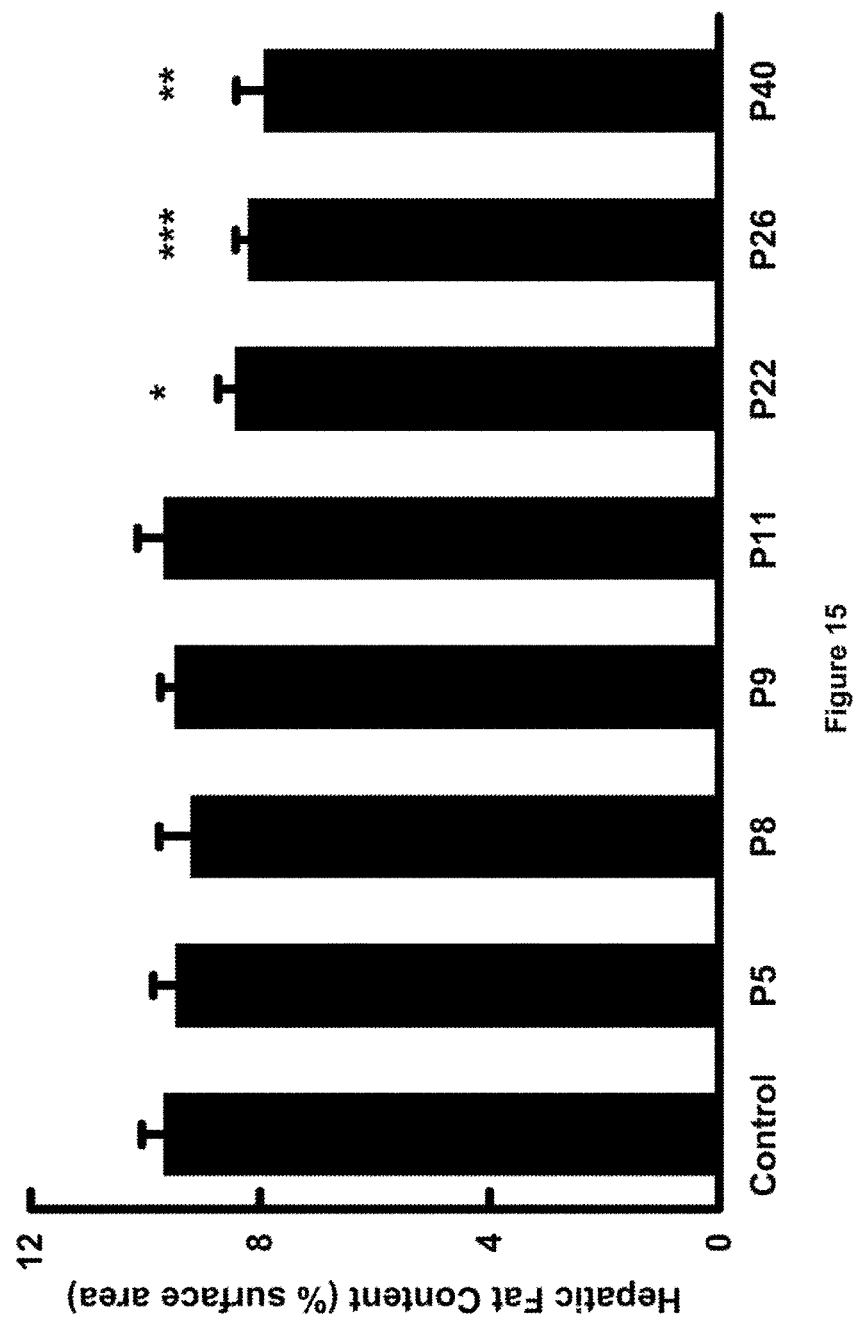
FIG. 15: Effect of test compounds on accumulation of fat in the liver in SHR on a 2.2% salt diet after 4 weeks treatment with test compound in drinking solution or drinking solution alone.

Fat in the liver after 4 weeks treatment with 500 pmol/kg/min of P22, P26 and P40 was reduced compared to 18 week controls (FIG. 15, *p<0.05, p<0.025 and *p<0.01) demonstrating that these compounds reduce accumulation of hepatic fat.

Example 12: Comparisons of In Vitro and In Vivo Screening of Compounds

Figure 16:
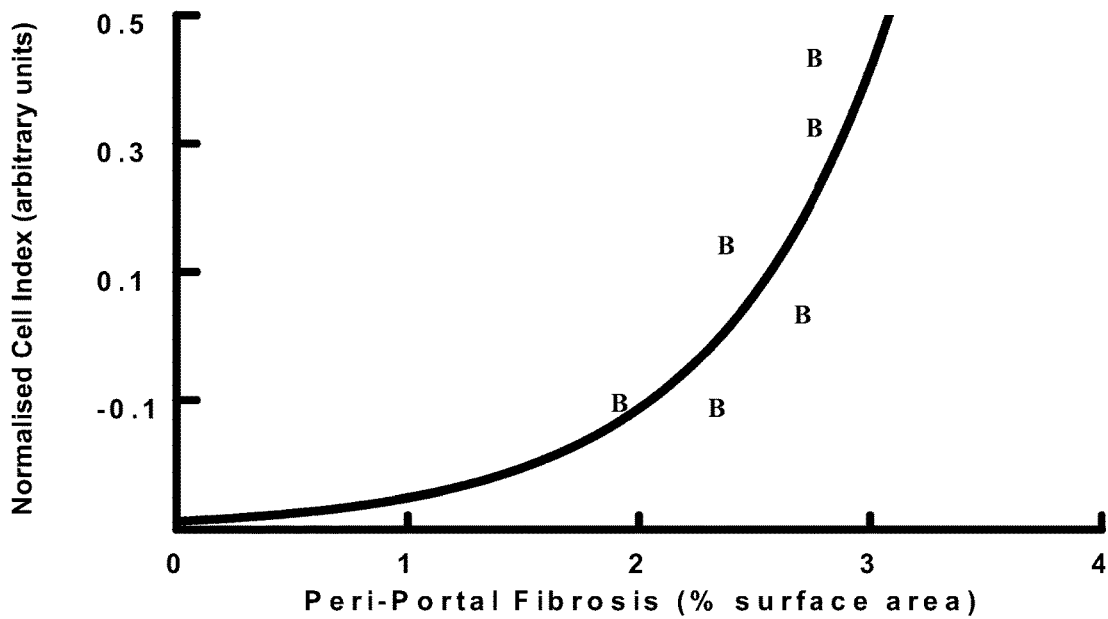
FIG. 16: Comparison of cell impedance in A10 vascular smooth muscle cells and the level of hepatic fibrosis in SHR treated with test compounds.

A comparison of cell impedance in A10 vascular smooth muscle cells and the level of hepatic fibrosis in SHR treated with various test compounds showed that the in vitro assay is predictive of the ability of the test compounds to decrease fibrosis in the liver (FIG. 16, $R^2$=0.618).

Figure 17:
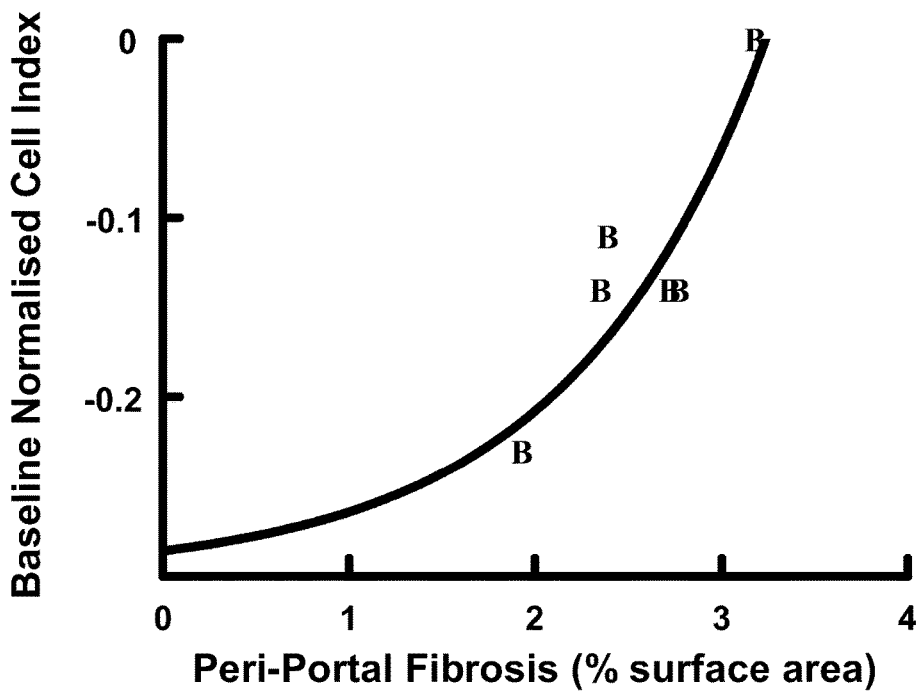
FIG. 17: Comparison of cell impedance in bovine aortic endothelial cells and the level of hepatic fibrosis in SHR treated with test compounds.

A comparison of cell impedance in bovine aortic endothelial cells and the level of hepatic fibrosis in SHR treated with various test compounds showed that the in vitro assay is predictive of the ability of the test compounds to decrease fibrosis in the liver (FIG. 17, $R^2$=0.759).

Figure 18:
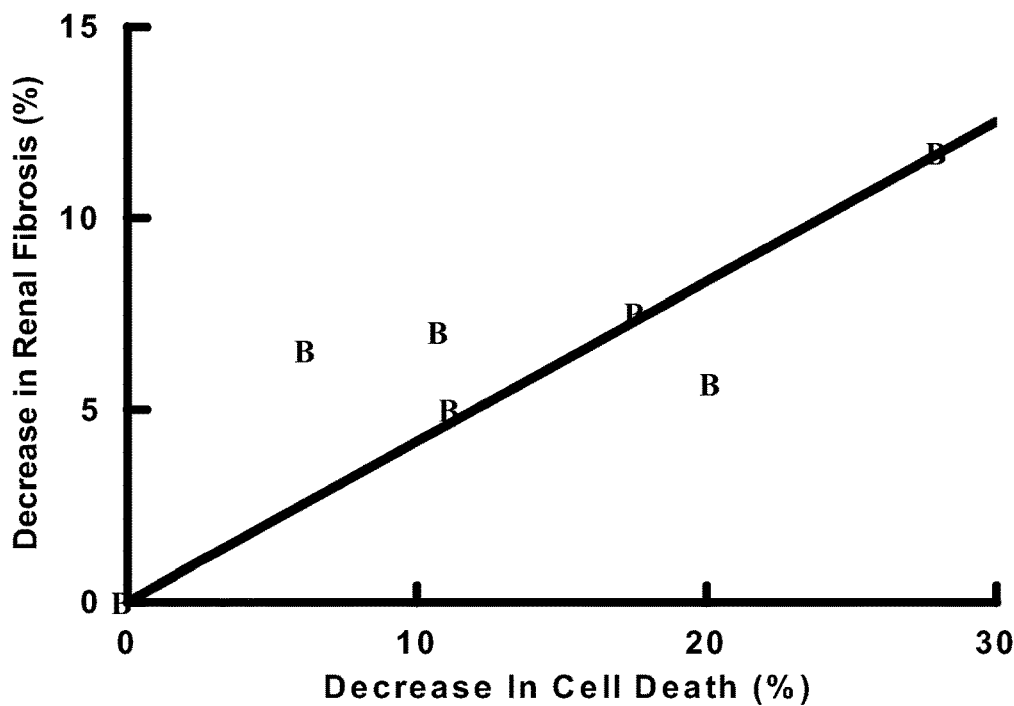
FIG. 18: Comparison of rescue of renal proximal tubule cells from cis-platin induced cytotoxicity and level of renal fibrosis in SHR treated with test compounds.

A comparison of rescue of renal proximal tubule cells from cis-platin induced cytotoxicity and the level of renal fibrosis in SHR treated with various test compounds showed that showed that the in vitro assay is predictive of a compound's ability to decrease fibrosis in the kidney (FIG. 18, $R^2$=0.914).

Figure 19:
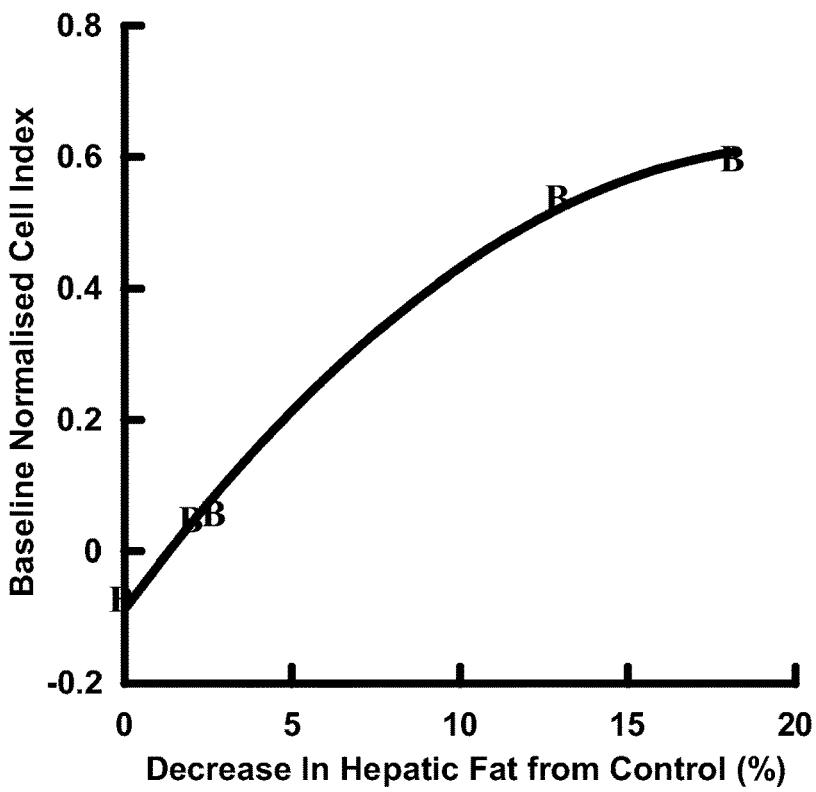
FIG. 19: Comparison of cell impedance in bovine aortic endothelial cells and the level of hepatic fat content in SHR treated with test compounds.

A comparison of cell impedance in bovine aortic endothelial cells and the level of hepatic fat in SHR treated with various test compounds showed that the in vitro assay is predictive of the ability of the test compounds to decrease fat in the liver (FIG. 19, $R^2$=0.996).

The claims defining the invention are as follows:

1. A compound of the formula:

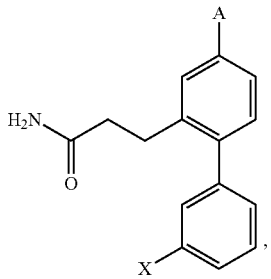

wherein:
A is:

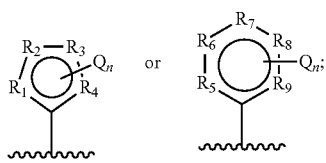

$R_1$ to $R_9$ are independently C, N, O or S;
Q is independently selected from $C_{1-6}$alkyl, halo, $C_{0-6}$alkyl carboxylic acid, amino, hydroxy and $C_{1-6}$alkoxy;
n is 0, 1, 2, 3 or 4; and
X is —OH or

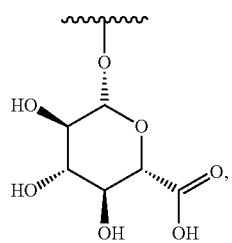

or a pharmacologically acceptable salt, stereoisomer, diastereomer, enantiomer, racemate, hydrate and/or solvate thereof,
wherein when X is —OH, A cannot be unsubstituted phenyl.

2. The compound according to claim 1, wherein Q is independently selected from —CH$_3$, —C(O)OH, —F, —NH$_2$, —OH and —OCH$_3$.

3. The compound according to claim 1, wherein $R_5$ to $R_9$ are independently C or N.

4. The compound according to claim 1, wherein n is 0, 1 or 2.

5. The compound according to claim 1, wherein the $C_{0-6}$alkyl carboxylic acid is carboxylic acid.

6. The compound according to claim 1, wherein X is —OH.

7. The compound according to claim 1, wherein X is

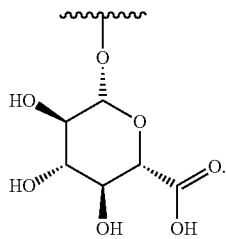

8. The compound according to claim 1, wherein the compound is selected from the group consisting of:

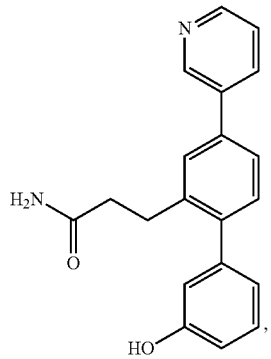

(P5)

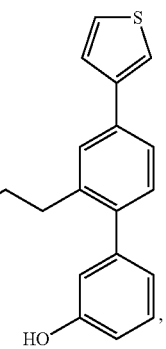

(P8)

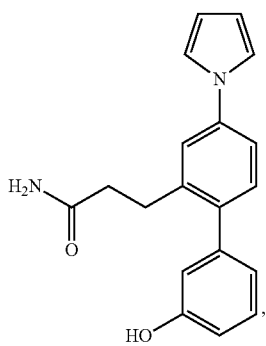
(P9)
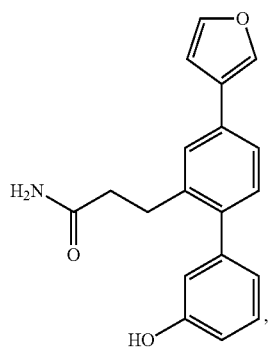
(P11)
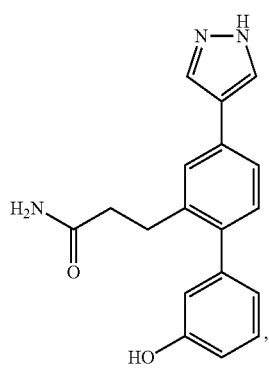
(P22)
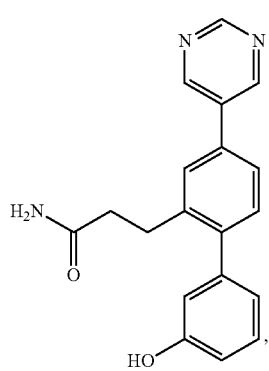
(P26)
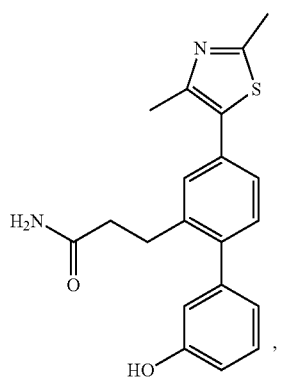
(P40)
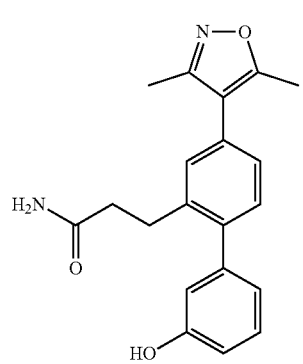
(P41)
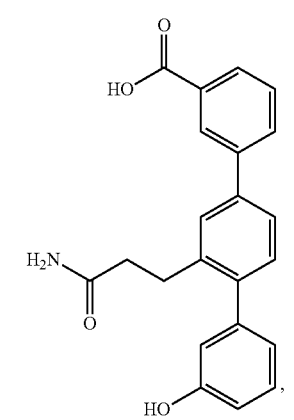
(P47)
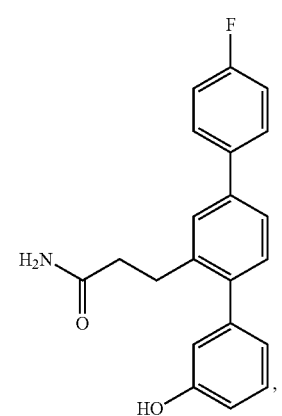
(P3)

(P49)
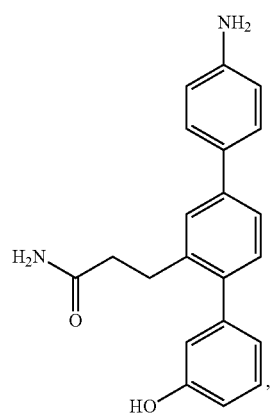
(P46)
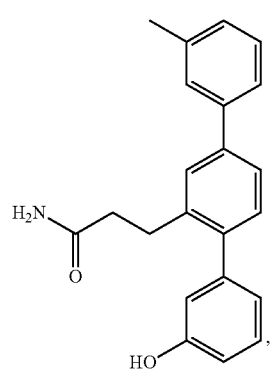
(P48)
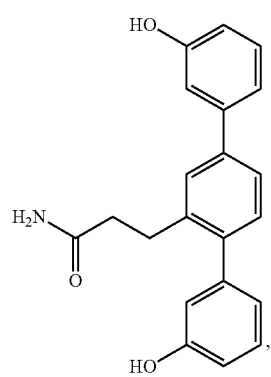
(P50)
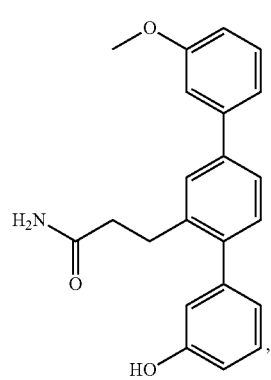
(P1)
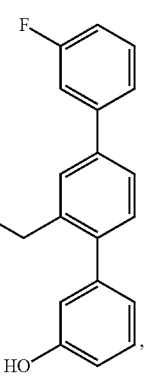
(P6)
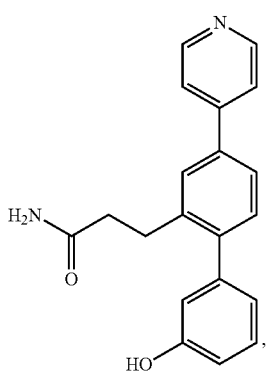
(P33)
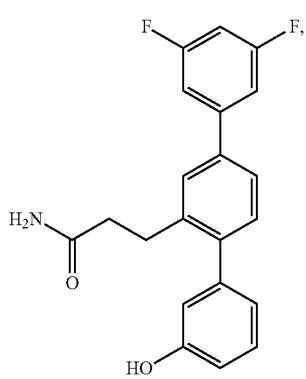
(P38)
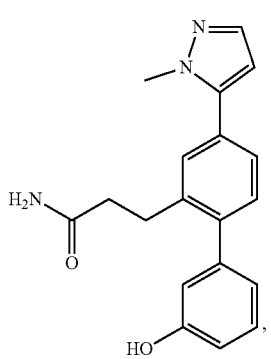

or a pharmacologically acceptable salt, glucuronide, stereoisomer, diastereomer, enantiomer, racemate, hydrate and/or solvate thereof.

9. The compound according to claim 1, wherein the compound is:

(P104)

or a pharmacologically acceptable salt, stereoisomer, diastereomer, enantiomer, racemate, hydrate and/or solvate thereof.

10. A pharmaceutical composition comprising the compound according to claim 1, and a pharmaceutically acceptable excipient.

11. A method for the therapeutic treatment of kidney and/or liver disease in a subject comprising administering to the subject a compound according to claim 1.

12. The method according to claim 11, wherein the treatment reduces or slows the progression of kidney and/or liver fibrosis.

13. The method according to claim 11, wherein the treatment reduces established kidney and/or liver fibrosis.

14. The method according to claim 11, wherein the treatment reduces or slows renal tubular cell death.

15. The method according to claim 11 wherein the treatment reduces or slows accumulation of hepatic fat.

16. The method according to claim 11 wherein the treatment restores normal tissue architecture.

17. A compound of the formula:
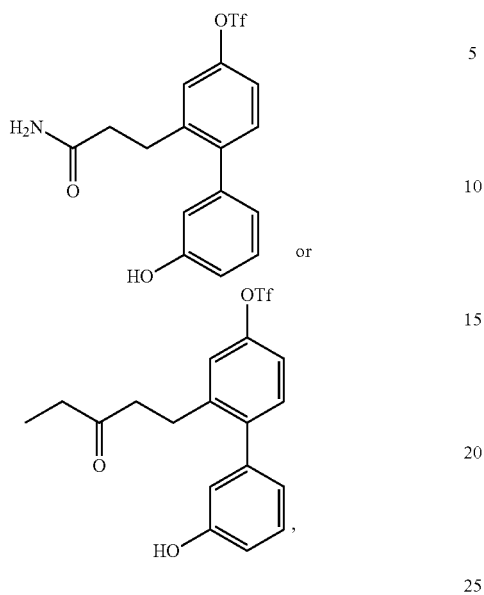
or a pharmacologically acceptable salt, glucuronide, stereoisomer, diastereomer, enantiomer, racemate, hydrate and/or solvate thereof.
* * * * *